United States Patent
Diem et al.

(10) Patent No.: US 10,597,438 B2
(45) Date of Patent: Mar. 24, 2020

(54) PD-L1 BINDING FIBRONECTIN TYPE III DOMAINS

(71) Applicant: Janssen Biotech, Inc., Horsham, PA (US)

(72) Inventors: Michael Diem, Havertown, PA (US); Rebecca Hawkins, Harleysville, PA (US); Steven Jacobs, North Wales, PA (US); Manuel Sepulveda, Princeton Junction, NJ (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 15/840,281

(22) Filed: Dec. 13, 2017

(65) Prior Publication Data

US 2018/0162928 A1 Jun. 14, 2018

Related U.S. Application Data

(60) Provisional application No. 62/434,054, filed on Dec. 14, 2016.

(51) Int. Cl.
| | | |
|---|---|---|
| C07K 14/705 | (2006.01) |
| C07K 14/71 | (2006.01) |
| C07K 14/78 | (2006.01) |
| A61P 35/00 | (2006.01) |
| C12N 15/85 | (2006.01) |
| C07K 16/28 | (2006.01) |
| A61K 38/17 | (2006.01) |

(52) U.S. Cl.
CPC ............. *C07K 14/78* (2013.01); *A61P 35/00* (2018.01); *C07K 14/705* (2013.01); *C07K 14/70596* (2013.01); *C07K 14/71* (2013.01); *C07K 16/2827* (2013.01); *C12N 15/85* (2013.01); *A61K 38/179* (2013.01); *C07K 2318/20* (2013.01)

(58) Field of Classification Search
CPC .... A61K 38/17; A61K 38/39; C07K 2317/31; C07K 2317/622; C07K 2317/92; C07K 14/78; C07K 14/47
See application file for complete search history.

(56) References Cited

U.S. PATENT DOCUMENTS

| | | | |
|---|---|---|---|
| 5,223,409 A | 6/1993 | Ladner et al. |
| 5,643,768 A | 7/1997 | Kawasaki |
| 5,856,456 A | 1/1999 | Whitlow et al. |
| 6,172,197 B1 | 1/2001 | McCafferty et al. |
| 6,472,147 B1 | 10/2002 | Janda et al. |
| 6,582,915 B1 | 6/2003 | Griffiths et al. |
| 6,673,901 B2 | 1/2004 | Koide |
| 6,969,108 B2 | 11/2005 | Fukumoto et al. |
| 7,709,214 B2 | 5/2010 | Freeman et al. |
| 7,794,710 B2 | 9/2010 | Chen et al. |
| 7,842,476 B2 | 11/2010 | McGregor et al. |
| 7,943,743 B2 | 5/2011 | Korman et al. |
| 8,217,149 B2 | 7/2012 | Irving et al. |
| 8,278,419 B2 | 10/2012 | Jacobs et al. |
| 8,552,154 B2 | 10/2013 | Freeman et al. |
| 8,569,227 B2 | 10/2013 | Jacobs |
| 8,741,295 B2 | 6/2014 | Olive |
| 8,779,108 B2 | 7/2014 | Queva et al. |
| 8,981,063 B2 | 3/2015 | Chen |
| 9,175,082 B2 | 11/2015 | Zhou et al. |
| 9,212,224 B2 | 12/2015 | Cogswell et al. |
| 2010/0216708 A1 | 8/2010 | Jacobs et al. |
| 2011/0118144 A1 | 5/2011 | Hyun et al. |
| 2013/0226834 A1 | 8/2013 | Gannalo, II |
| 2014/0341917 A1 | 11/2014 | Nastri et al. |
| 2015/0197571 A1 | 7/2015 | Freeman et al. |
| 2015/0203580 A1 | 7/2015 | Papadopoulos et al. |
| 2015/0274835 A1 | 10/2015 | Marasco et al. |
| 2015/0346208 A1 | 12/2015 | Couto et al. |
| 2015/0355184 A1 | 12/2015 | Pierce et al. |
| 2017/0258948 A1 * | 9/2017 | Morin ............... C07K 14/78 |

FOREIGN PATENT DOCUMENTS

| | | |
|---|---|---|
| EP | 1210428 A1 | 6/2002 |
| EP | 2935329 A1 | 10/2015 |
| WO | 2001014557 A1 | 3/2001 |
| WO | 2009085462 A1 | 7/2009 |
| WO | 2014100079 A1 | 6/2014 |
| WO | 2014165082 A2 | 10/2014 |
| WO | 2014209804 A1 | 12/2014 |
| WO | 2015061668 A1 | 4/2015 |
| WO | 2015092393 A2 | 6/2015 |
| WO | 2015109124 A2 | 7/2015 |
| WO | 2015195163 A1 | 12/2015 |
| WO | 2016000619 A1 | 1/2016 |
| WO | WO-2016086021 A1 * | 6/2016 |

OTHER PUBLICATIONS

Diem et al. Selection of high-affinity Centyrin FN3 domains from a simply library diversified at a combination of strand and loop positions. Protein Engineer Design Select 27(1): 419-429, 2014.*
Song et al. Cancer stem cells—an old idea that's new again: implications for the diagnosis and treatment of brease cancer. Expert Opin Biol Ther 7(4): 431-438, 2007.*
Tannock and Hill. The Basic Science of Oncology. 1998. New York: McGraw-Hill;; pp. 357-358.*
Alfthan et al., "Properties of a single-chain antibody containing different linker peptides," Protein Engineering, vol. 8, No. 7, pp. 725-731 (1995).
Binz et al., "High-affinity binders selected from designed ankyrin repeat protein libraries," Nature Biotechnology, vol. 22, No. 5, pp. 575-582 (May 2004).
Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).

(Continued)

*Primary Examiner* — Bridget E Bunner
(74) *Attorney, Agent, or Firm* — Pepper Hamilton LLP

(57) ABSTRACT

FN3 domains that specifically bind to PD-L1, their conjugates, isolated nucleotides encoding the molecules, vectors, host cells, and methods of making and using them are useful in therapeutic and diagnostic applications.

17 Claims, No Drawings

Specification includes a Sequence Listing.

(56) References Cited

OTHER PUBLICATIONS

Bork et al., "Proposed acquisition of an animal protein domain by bacteria," Proceedings of the National Academy of Science, USA, vol. 89, pp. 8990-8994 (1992).

Garon et al., "Pembrolizumab for the Treatment of Non-Small-Cell Lung Cancer," The New England Journal of Medicine, vol. 372, No. 21, pp. 2018-2028 (May 21, 2015).

Hallewell et al., "Genetically Engineered Polymers of Human CuZN Superoxide Dismutase," The Journal of Biological Chemistry, vol. 264, No. 9, pp. 5260-5268 (1989).

Hanes et al., "In vitro selection and evolution of functional proteins by using ribosome display," Proceedings of the National Academy of Sciences USA, vol. 94, pp. 4937-4942 (1997).

Jacobs et al., "Design of novel FN3 domains with high stability by a consensus sequence approach," Protein Engineering, Design & Selection, vol. 25, No. 3, pp. 107-117 (2012).

Koide et al., "High-affinity single-domain binding proteins with a binary-code interface," PNAS, vol. 104, No. 16, pp. 6632-6637 (Apr. 17, 2017).

Lepenies et al., "The Role of Negative Costimulators During Parasitic Infections," Endocrine, Metabolic & Immune Disorders—Drug Targets, vol. 8, pp. 279-288 (2008).

McLaughlin et al., "Quantitative Assessmenet of the Heterogeneity of PD-L1 Expression in Non-small Cell Lung Cancer (NSCLC)," JAMA Oncol., vol. 2, No. 1, pp. 46-54, (Jan. 2016).

Meinke et al., "Cellulose-Binding Polypeptides from Cellulomonas fimi: Endoglucanase D (CenD), a Family A b-1,4-Glucanase," Journal of Bacteriology, vol. 175, No. 7, pp. 1910-1918 (1993).

Odegrip et al., "CIS display: In vitro selection of peptides from libraries of protein-DNA complexes," Proceedings of the National Academy of Science USA, vol. 101, No. 9, pp. 2806-2810 (2004).

Olson et al., "Design, expression, and stability of a diverse protein library based on the human fibronectin type III domain," Protein Science, vol. 16, pp. 476-484 (2007).

Roberts et al., "RNA-peptide fusions for the in vitro selection of peptides and proteins," Proceedings of the National Academy of Science USA, vol. 94, pp. 12297-12302 (1997).

Robinson et al., "Covalent Attachment of Arc Repressor Subunits by a Peptide Linker Enhances Affinity for Operator DNA," Biochemistry, vol. 35, pp. 109-116 (1996).

Strohl, William R., "Optimization of Fc-mediated effector functions of monoclonal antibodies," Current Opinion in Biotechnology, vol. 20, pp. 685-691 (2009).

Tie et al., "Safety and efficacy of nivolumab in the treatment of cancers: A meta-analysis of 27 prospective clinical trials," International Journal of Cancer, vol. 140, pp. 948-958, (2017).

Wang et al., "VISTA, a novel mouse Ig superfamily ligand that negatively regulates T cell responses," Journal of Experimental Medicine, vol. 208, No. 3, pp. 577-592 (Mar. 14, 2011).

Watanabe et al., "Gene Cloning of Chitinase Al from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).

\* cited by examiner

SEQUENCE LISTING

<160> NUMBER OF SEQ ID NOS: 136

<210> SEQ ID NO 1
<211> LENGTH: 89
<212> TYPE: PRT
<213> ORGANISM: Artificial Sequence
<220> FEATURE:
<223> OTHER INFORMATION: Tencon

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly His Arg Ser
65                  70                  75                  80

Asn Pro Leu Ser Ala Glu Phe Thr Thr
                85

<210> SEQ ID NO 2
<211> LENGTH: 94
<212> TYPE: PRT
<213> ORGANISM: Artificial Sequence

```
<220> FEATURE:
<223> OTHER INFORMATION: TCL1 library
<220> FEATURE:
<221> NAME/KEY: MISC_FEATURE
<222> LOCATION: (75)..(75)
<223> OTHER INFORMATION: Xaa is any amino acid
<220> FEATURE:
<221> NAME/KEY: MISC_FEATURE
<222> LOCATION: (76)..(76)
<223> OTHER INFORMATION: Xaa is any amino acid
<220> FEATURE:
<221> NAME/KEY: MISC_FEATURE
<222> LOCATION: (77)..(77)
<223> OTHER INFORMATION: Xaa is any amino acid
<220> FEATURE:
<221> NAME/KEY: MISC_FEATURE
<222> LOCATION: (78)..(78)
<223> OTHER INFORMATION: Xaa is any amino acid
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is any amino acid
<220> FEATURE:
<221> NAME/KEY: MISC_FEATURE
<222> LOCATION: (81)..(81)
<223> OTHER INFORMATION: Xaa is any amino acid
<220> FEATURE:
<221> NAME/KEY: MISC_FEATURE
<222> LOCATION: (82)..(82)
<223> OTHER INFORMATION: Xaa is any amino acid or deleted
<220> FEATURE:
<221> NAME/KEY: MISC_FEATURE
<222> LOCATION: (83)..(83)
<223> OTHER INFORMATION: Xaa is any amino acid or deleted
<220> FEATURE:
<221> NAME/KEY: MISC_FEATURE
<222> LOCATION: (84)..(84)
<223> OTHER INFORMATION: Xaa is any amino acid or deleted
<220> FEATURE:
<221> NAME/KEY: MISC_FEATURE
<222> LOCATION: (85)..(85)
<223> OTHER INFORMATION: Xaa is any amino acid or deleted
<220> FEATURE:
<221> NAME/KEY: MISC_FEATURE
<222> LOCATION: (86)..(86)
<223> OTHER INFORMATION: Xaa is any amino acid or deleted

<400> SEQUENCE: 2

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Pro Leu Ser Ala Glu Phe Thr Thr
                85                  90

<210> SEQ ID NO 3
<211> LENGTH: 89
<212> TYPE: PRT
<213> ORGANISM: Artificial Sequence
<220> FEATURE:
<223> OTHER INFORMATION: TCL2 library
<220> FEATURE:
```

```
<221> NAME/KEY: MISC_FEATURE
<222> LOCATION: (22)..(22)
<223> OTHER INFORMATION: Xaa is is Ala, Arg, Asn, Asp, Glu, Gln, Gly,
      His, Ile, Leu, Lys, Phe, Pro, Ser, Thr, Trp, Tyr or Val
<220> FEATURE:
<221> NAME/KEY: MISC_FEATURE
<222> LOCATION: (23)..(23)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (24)..(24)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (25)..(25)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (26)..(26)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (27)..(27)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (28)..(28)
<223> OTHER INFORMATION: Xaa is Phe, Ile, Leu, Val or Tyr
<220> FEATURE:
<221> NAME/KEY: MISC_FEATURE
<222> LOCATION: (29)..(29)
<223> OTHER INFORMATION: Xaa is Asp, Glu or Thr
<220> FEATURE:
<221> NAME/KEY: MISC_FEATURE
<222> LOCATION: (75)..(75)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (76)..(76)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (77)..(77)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (78)..(78)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (79)..(79)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (81)..(81)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val
<220> FEATURE:
<221> NAME/KEY: MISC_FEATURE
<222> LOCATION: (82)..(82)
<223> OTHER INFORMATION: Xaa is Ala, Arg, Asn, Asp, Glu, Gln, Gly, His,
      Ile, Leu, Lys, Phe, Pro, Ser, Thr, Trp, Tyr or Val

<400> SEQUENCE: 3

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Xaa Ser Phe Leu
```

```
                    20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Xaa Xaa Xaa Xaa Ser
65                  70                  75                  80

Xaa Xaa Leu Ser Ala Glu Phe Thr Thr
                85

<210> SEQ ID NO 4
<211> LENGTH: 89
<212> TYPE: PRT
<213> ORGANISM: Artificial Sequence
<220> FEATURE:
<223> OTHER INFORMATION: Stabilized tencon

<400> SEQUENCE: 4

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 5
<211> LENGTH: 97
<212> TYPE: PRT
<213> ORGANISM: Artificial Sequence
<220> FEATURE:
<223> OTHER INFORMATION: TCL7
<220> FEATURE:
<221> NAME/KEY: MISC_FEATURE
<222> LOCATION: (22)..(22)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (23)..(23)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (24)..(24)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (25)..(25)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (26)..(26)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (27)..(27)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
```

```
<220> FEATURE:
<221> NAME/KEY: MISC_FEATURE
<222> LOCATION: (28)..(28)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (29)..(29)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (30)..(30)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (78)..(78)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (79)..(79)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (80)..(80)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (81)..(81)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (82)..(82)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (83)..(83)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (84)..(84)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (85)..(85)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (86)..(86)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (87)..(87)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted

<400> SEQUENCE: 5

Leu Pro Ala Pro Lys Asn Leu Val Val Ser Arg Val Thr Glu Asp Ser
1               5                   10                  15

Ala Arg Leu Ser Trp Xaa Xaa Xaa Xaa Xaa Xaa Xaa Xaa Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
    50                  55                  60
```

```
Lys Pro Gly Thr Glu Tyr Thr Val Ser Ile Tyr Gly Val Xaa Xaa Xaa
 65                  70                  75                  80

Xaa Xaa Xaa Xaa Xaa Xaa Xaa Ser Asn Pro Leu Ser Ala Ile Phe Thr
             85                  90                  95

Thr

<210> SEQ ID NO 6
<211> LENGTH: 96
<212> TYPE: PRT
<213> ORGANISM: Artificial Sequence
<220> FEATURE:
<223> OTHER INFORMATION: TCL9
<220> FEATURE:
<221> NAME/KEY: MISC_FEATURE
<222> LOCATION: (75)..(75)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (76)..(76)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (77)..(77)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (78)..(78)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (79)..(79)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (80)..(80)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (81)..(81)
<223> OTHER INFORMATION: Xaa is Ala, Asp, Glu, Phe, Gly, His, Ile, Lys,
      Leu, Asn, Pro, Qln, Arg, Ser, Thr, Val, Trp or Tyr
<220> FEATURE:
<221> NAME/KEY: MISC_FEATURE
<222> LOCATION: (82)..(82)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (83)..(83)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (84)..(84)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (85)..(85)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted
<220> FEATURE:
<221> NAME/KEY: MISC_FEATURE
<222> LOCATION: (86)..(86)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr or deleted

<400> SEQUENCE: 6
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95
```

<210> SEQ ID NO 7
<211> LENGTH: 89
<212> TYPE: PRT
<213> ORGANISM: Artificial Sequence
<220> FEATURE:
<223> OTHER INFORMATION: TCL14
<220> FEATURE:
<221> NAME/KEY: MISC_FEATURE
<222> LOCATION: (32)..(32)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (34)..(34)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (36)..(36)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (38)..(38)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (39)..(39)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (40)..(40)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (41)..(41)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (68)..(68)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (70)..(70)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (72)..(72)
<223> OTHER INFORMATION: Xaa is Ala, Asp, Glu, Phe, Gly, His, Ile, Lys,
      Leu, Asn, Pro, Qln, Arg, Ser, Thr, Val, Trp, Tyr, Cys or Met
<220> FEATURE:
<221> NAME/KEY: MISC_FEATURE
<222> LOCATION: (78)..(78)
<223> OTHER INFORMATION: Xaa is Ala, Asp, Glu, Phe, Gly, His, Ile, Lys,

```
      Leu, Asn, Pro, Gln, Arg, Ser, Thr, Val, Trp, Tyr, Cys or Met
<220> FEATURE:
<221> NAME/KEY: MISC_FEATURE
<222> LOCATION: (79)..(79)
<223> OTHER INFORMATION: Xaa is Ala, Asp, Glu, Phe, Gly, His, Ile, Lys,
      Leu, Asn, Pro, Gln, Arg, Ser, Thr, Val, Trp, Tyr, Cys or Met
<220> FEATURE:
<221> NAME/KEY: MISC_FEATURE
<222> LOCATION: (81)..(81)
<223> OTHER INFORMATION: Xaa is Ala, Asp, Glu, Phe, Gly, His, Ile, Lys,
      Leu, Asn, Pro, Gln, Arg, Ser, Thr, Val, Trp, Tyr, Cys or Met

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85

<210> SEQ ID NO 8
<211> LENGTH: 89
<212> TYPE: PRT
<213> ORGANISM: Artificial Sequence
<220> FEATURE:
<223> OTHER INFORMATION: TCL24
<220> FEATURE:
<221> NAME/KEY: MISC_FEATURE
<222> LOCATION: (32)..(32)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
<220> FEATURE:
<221> NAME/KEY: MISC_FEATURE
<222> LOCATION: (34)..(34)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
<220> FEATURE:
<221> NAME/KEY: MISC_FEATURE
<222> LOCATION: (36)..(36)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
<220> FEATURE:
<221> NAME/KEY: MISC_FEATURE
<222> LOCATION: (38)..(38)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
<220> FEATURE:
<221> NAME/KEY: MISC_FEATURE
<222> LOCATION: (39)..(39)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
<220> FEATURE:
<221> NAME/KEY: MISC_FEATURE
<222> LOCATION: (40)..(40)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
<220> FEATURE:
<221> NAME/KEY: MISC_FEATURE
<222> LOCATION: (41)..(41)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
<220> FEATURE:
<221> NAME/KEY: MISC_FEATURE
<222> LOCATION: (46)..(46)
<223> OTHER INFORMATION: Xaa is Ala, Asp, Glu, Phe, Gly, His, Ile, Lys,
      Leu, Asn, Pro, Gln, Arg, Ser, Thr, Val, Tyr or Trp
```

```
<220> FEATURE:
<221> NAME/KEY: MISC_FEATURE
<222> LOCATION: (48)..(48)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (68)..(68)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (70)..(70)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (72)..(72)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (78)..(78)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (79)..(79)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (81)..(81)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (84)..(84)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp
<220> FEATURE:
<221> NAME/KEY: MISC_FEATURE
<222> LOCATION: (86)..(86)
<223> OTHER INFORMATION: Xaa is Ala, Asp, Glu, Phe, Gly, His, Ile, Lys,
      Leu, Asn, Pro, Qln, Arg, Ser, Thr, Val, Tyr or Trp

<400> SEQUENCE: 8

Leu Pro Ala Pro Lys Asn Leu Val Val Ser Arg Val Thr Glu Asp Ser
1               5                   10                  15

Ala Arg Leu Ser Trp Thr Ala Pro Ala Ala Phe Asp Ser Phe Xaa
            20                  25                  30

Ile Xaa Tyr Xaa Glu Xaa Xaa Xaa Xaa Gly Glu Ala Ile Xaa Leu Xaa
            35                  40                  45

Val Pro Gly Ser Glu Arg Ser Tyr Asp Leu Thr Gly Leu Lys Pro Gly
            50                  55                  60

Thr Glu Tyr Xaa Val Xaa Ile Xaa Gly Val Lys Gly Gly Xaa Xaa Ser
65                  70                  75                  80

Xaa Pro Leu Xaa Ala Xaa Phe Thr Thr
                85

<210> SEQ ID NO 9
<211> LENGTH: 19
<212> TYPE: DNA
<213> ORGANISM: Artificial Sequence
<220> FEATURE:
<223> OTHER INFORMATION: Sloning-FOR

<400> SEQUENCE: 9
gtgacacggc ggttagaac                                              19
```

```
<210> SEQ ID NO 10
<211> LENGTH: 20
<212> TYPE: DNA
<213> ORGANISM: Artificial Sequence
<220> FEATURE:
<223> OTHER INFORMATION: Sloning-REV

<400> SEQUENCE: 10
gcctttggga agcttctaag                                              20

<210> SEQ ID NO 11
<211> LENGTH: 30
<212> TYPE: DNA
<213> ORGANISM: Artificial Sequence
<220> FEATURE:
<223> OTHER INFORMATION: POP2250

<400> SEQUENCE: 11
cggcggttag aacgcggcta caattaatac                                   30

<210> SEQ ID NO 12
<211> LENGTH: 22
<212> TYPE: DNA
<213> ORGANISM: Artificial Sequence
<220> FEATURE:
<223> OTHER INFORMATION: DigLigRev

<400> SEQUENCE: 12
catgattacg ccaagctcag aa                                           22

<210> SEQ ID NO 13
<211> LENGTH: 385
<212> TYPE: DNA
<213> ORGANISM: Artificial Sequence
<220> FEATURE:
<223> OTHER INFORMATION: BC9
<220> FEATURE:
<221> NAME/KEY: misc_feature
<222> LOCATION: (198)..(224)
<223> OTHER INFORMATION: n is a, c, g, or t

<400> SEQUENCE: 13
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
caggatctac catgctgccg gcgccgaaaa acctggttgt ttctgaagtt accgaagact  180
ctctgcgtct gtcttggnnn nnnnnnnnn nnnnnnnnnn nnnnttygac tctttcctga  240
tccagtacca ggaatctgaa aaagttggtg aagcgatcaa cctgaccgtt ccgggttctg  300
aacgttctta cgacctgacc ggtctgaaac cgggtaccga atacaccgtt tctatctacg  360
gtgttcttag aagcttccca aaggc                                       385

<210> SEQ ID NO 14
<211> LENGTH: 382
<212> TYPE: DNA
<213> ORGANISM: Artificial Sequence
<220> FEATURE:
<223> OTHER INFORMATION: BC8
<220> FEATURE:
<221> NAME/KEY: misc_feature
<222> LOCATION: (198)..(221)
<223> OTHER INFORMATION: n is a, c, g, or t

<400> SEQUENCE: 14
gtgacacggc ggttagaacg cggctacaat taatacataa ccccatcccc ctgttgacaa   60
```

```
ttaatcatcg gctcgtataa tgtgtggaat tgtgagcgga taacaatttc acacaggaaa      120
caggatctac catgctgccg gcgccgaaaa acctggttgt ttctgaagtt accgaagact      180
ctctgcgtct gtcttggnnn nnnnnnnnnn nnnnnnnnnn nttygactct tcctgatcc       240 agtaccagga atctgaaaaa gttggtgaag cgatcaacct gaccgttccg ggttctgaac      300
gttcttacga cctgaccggt ctgaaaccgg gtaccgaata caccgtttct atctacggtg      360
ttcttagaag cttcccaaag gc                                               382

<210> SEQ ID NO 15
<211> LENGTH: 379
<212> TYPE: DNA
<213> ORGANISM: Artificial Sequence
<220> FEATURE:
<223> OTHER INFORMATION: BC7
<220> FEATURE:
<221> NAME/KEY: misc_feature
<222> LOCATION: (198)..(218)
<223> OTHER INFORMATION: n is a, c, g, or t

<400> SEQUENCE: 15
gtgacacggc ggttagaacg cggctacaat taatacataa ccccatcccc ctgttgacaa       60
ttaatcatcg gctcgtataa tgtgtggaat tgtgagcgga taacaatttc acacaggaaa     120
caggatctac catgctgccg gcgccgaaaa acctggttgt ttctgaagtt accgaagact     180
ctctgcgtct gtcttggnnn nnnnnnnnn nnnnnnnntt ygactctttc ctgatccagt     240
accaggaatc tgaaaaagtt ggtgaagcga tcaacctgac cgttccgggt tctgaacgtt     300
cttacgacct gaccggtctg aaacggggta ccgaatacac cgtttctatc tacggtgttc     360
ttagaagctt cccaaaggc                                                  379

<210> SEQ ID NO 16
<211> LENGTH: 376
<212> TYPE: DNA
<213> ORGANISM: Artificial Sequence
<220> FEATURE:
<223> OTHER INFORMATION: BC6
<220> FEATURE:
<221> NAME/KEY: misc_feature
<222> LOCATION: (198)..(215)
<223> OTHER INFORMATION: n is a, c, g, or t

<400> SEQUENCE: 16
gtgacacggc ggttagaacg cggctacaat taatacataa ccccatcccc ctgttgacaa       60
ttaatcatcg gctcgtataa tgtgtggaat tgtgagcgga taacaatttc acacaggaaa     120
caggatctac catgctgccg gcgccgaaaa acctggttgt ttctgaagtt accgaagact     180
ctctgcgtct gtcttggnnn nnnnnnnnn nnnnttyga ctctttcctg atccagtacc     240
aggaatctga aaaagttggt gaagcgatca acctgaccgt tccgggttct gaacgttctt     300
acgacctgac cggtctgaaa ccgggtaccg aatacaccgt ttctatctac ggtgttctta     360
gaagcttccc aaaggc                                                     376

<210> SEQ ID NO 17
<211> LENGTH: 131
<212> TYPE: DNA
<213> ORGANISM: Artificial Sequence
<220> FEATURE:
<223> OTHER INFORMATION: 130mer-L17A

<400> SEQUENCE: 17
cggcggttag aacgcggcta caattaatac ataaccccat ccccctgttg acaattaatc       60
```

```
atcggctcgt ataatgtgtg aattgtgag cggataacaa tttcacacag gaaacaggat    120
ctaccatgct g                                                        131

<210> SEQ ID NO 18
<211> LENGTH: 30
<212> TYPE: DNA
<213> ORGANISM: Artificial Sequence
<220> FEATURE:
<223> OTHER INFORMATION: POP222ext

<400> SEQUENCE: 18
cggcggttag aacgcggcta caattaatac                                     30

<210> SEQ ID NO 19
<211> LENGTH: 81
<212> TYPE: DNA
<213> ORGANISM: Artificial Sequence
<220> FEATURE:
<223> OTHER INFORMATION: LS1114

<400> SEQUENCE: 19
ccaagacaga cgggcagagt cttcggtaac gcgagaaaca accaggtttt tcggcgccgg    60
cagcatggta gatcctgttt c                                              81

<210> SEQ ID NO 20
<211> LENGTH: 26
<212> TYPE: DNA
<213> ORGANISM: Artificial Sequence
<220> FEATURE:
<223> OTHER INFORMATION: LS1115

<400> SEQUENCE: 20
ccgaagactc tgcccgtctg tcttgg                                         26

<210> SEQ ID NO 21
<211> LENGTH: 45
<212> TYPE: DNA
<213> ORGANISM: Artificial Sequence
<220> FEATURE:
<223> OTHER INFORMATION: LS1117

<400> SEQUENCE: 21
cagtggtctc acggattcct ggtactggat caggaaagag tcgaa                    45

<210> SEQ ID NO 22
<211> LENGTH: 54
<212> TYPE: DNA
<213> ORGANISM: Artificial Sequence
<220> FEATURE:
<223> OTHER INFORMATION: SDG10

<400> SEQUENCE: 22
catgcggtct cttccgaaaa agttggtgaa gcgatcgtcc tgaccgttcc gggt          54

<210> SEQ ID NO 23
<211> LENGTH: 29
<212> TYPE: DNA
<213> ORGANISM: Artificial Sequence
<220> FEATURE:
<223> OTHER INFORMATION: SDG24

<400> SEQUENCE: 23
ggtggtgaag atcgcagaca gcgggttag                                      29
```

<210> SEQ ID NO 24
<211> LENGTH: 21
<212> TYPE: DNA
<213> ORGANISM: Artificial Sequence
<220> FEATURE:
<223> OTHER INFORMATION: POP2222

<400> SEQUENCE: 24
cggcggttag aacgcggcta c                                          21

<210> SEQ ID NO 25
<211> LENGTH: 61
<212> TYPE: DNA
<213> ORGANISM: Artificial Sequence
<220> FEATURE:
<223> OTHER INFORMATION: SDG28

<400> SEQUENCE: 25
aagatcagtt gcggccgcta gactagaacc gctgccaccg ccggtggtga agatcgcaga    60
c                                                                  61

<210> SEQ ID NO 26
<211> LENGTH: 485
<212> TYPE: DNA
<213> ORGANISM: Artificial Sequence
<220> FEATURE:
<223> OTHER INFORMATION: FG12
<220> FEATURE:
<221> NAME/KEY: misc_feature
<222> LOCATION: (357)..(392)
<223> OTHER INFORMATION: n is a, c, g, or t

<400> SEQUENCE: 26
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnnnnn nnnnnnnnnn nntctaaccc gctgtctgcg atcttcacca   420
ccggcggtca ccatcaccat caccatggca gcggttctag tctagcggcc gcaactgatc   480
ttggc                                                             485

<210> SEQ ID NO 27
<211> LENGTH: 482
<212> TYPE: DNA
<213> ORGANISM: Artificial Sequence
<220> FEATURE:
<223> OTHER INFORMATION: FG11
<220> FEATURE:
<221> NAME/KEY: misc_feature
<222> LOCATION: (357)..(389)
<223> OTHER INFORMATION: n is a, c, g, or t

<400> SEQUENCE: 27
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240

-continued

```
aggaatctga aaaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnnnnnn nnnnnnnnnt ctaacccgct gtctgcgatc ttcaccaccg    420
gcggtcacca tcaccatcac catggcagcg gttctagtct agcggccgca actgatcttg    480
gc                                                                   482
```

<210> SEQ ID NO 28
<211> LENGTH: 479
<212> TYPE: DNA
<213> ORGANISM: Artificial Sequence
<220> FEATURE:
<223> OTHER INFORMATION: FG10
<220> FEATURE:
<221> NAME/KEY: misc_feature
<222> LOCATION: (357)..(386)
<223> OTHER INFORMATION: n is a, c, g, or t

<400> SEQUENCE: 28

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa    120
caggatctac catgctgccg gcgccgaaaa acctggttgt ttctcgcgtt accgaagact    180
ctgcgcgtct gtcttggacc gcgccggacg cggcgttcga ctctttcctg atccagtacc    240
aggaatctga aaaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnnnnnn nnnnnntcta acccgctgtc tgcgatcttc accaccggcg    420
gtcaccatca ccatcaccat ggcagcggtt ctagtctagc ggccgcaact gatcttggc    479
```

<210> SEQ ID NO 29
<211> LENGTH: 476
<212> TYPE: DNA
<213> ORGANISM: Artificial Sequence
<220> FEATURE:
<223> OTHER INFORMATION: FG9
<220> FEATURE:
<221> NAME/KEY: misc_feature
<222> LOCATION: (357)..(383)
<223> OTHER INFORMATION: n is a, c, g, or t

<400> SEQUENCE: 29

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa    120
caggatctac catgctgccg gcgccgaaaa acctggttgt ttctcgcgtt accgaagact    180
ctgcgcgtct gtcttggacc gcgccggacg cggcgttcga ctctttcctg atccagtacc    240
aggaatctga aaaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnnnnnn nnntctaacc cgctgtctgc gatcttcacc accggcggtc    420
accatcacca tcaccatggc agcggttcta gtctagcggc cgcaactgat cttggc       476
```

<210> SEQ ID NO 30
<211> LENGTH: 473
<212> TYPE: DNA
<213> ORGANISM: Artificial Sequence
<220> FEATURE:
<223> OTHER INFORMATION: FG8
<220> FEATURE:

```
<221> NAME/KEY: misc_feature
<222> LOCATION: (357)..(380)
<223> OTHER INFORMATION: n is a, c, g, or t

<400> SEQUENCE: 30
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg cgccgaaaa acctggttgt ttctcgcgtt accgaagact     180
ctgcgcgtct gtcttggacc cgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn tctaacccgc tgtctgcgat cttcaccacc ggcggtcacc     420
atcaccatca ccatggcagc ggttctagtc tagcggccgc aactgatctt ggc             473

<210> SEQ ID NO 31
<211> LENGTH: 470
<212> TYPE: DNA
<213> ORGANISM: Artificial Sequence
<220> FEATURE:
<223> OTHER INFORMATION: FG7
<220> FEATURE:
<221> NAME/KEY: misc_feature
<222> LOCATION: (357)..(377)
<223> OTHER INFORMATION: n is a, c, g, or t

<400> SEQUENCE: 31
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg cgccgaaaa acctggttgt ttctcgcgtt accgaagact     180
ctgcgcgtct gtcttggacc cgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnntct aacccgctgt ctgcgatctt caccaccggc ggtcaccatc     420
accatcacca tggcagcggt tctagtctag cggccgcaac tgatcttggc                 470

<210> SEQ ID NO 32
<211> LENGTH: 220
<212> TYPE: PRT
<213> ORGANISM: Homo sapiens

<400> SEQUENCE: 32

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
```

```
            100                 105                 110
Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                    165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
                195                 200                 205

Pro Glu Leu Pro Leu Ala His Pro Pro Asn Glu Arg
        210                 215                 220

<210> SEQ ID NO 33
<211> LENGTH: 268
<212> TYPE: PRT
<213> ORGANISM: Homo sapiens

<400> SEQUENCE: 33

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255
```

```
Leu Arg Pro Glu Asp Gly His Cys Ser Trp Pro Leu
            260                 265
```

<210> SEQ ID NO 34
<211> LENGTH: 89
<212> TYPE: PRT
<213> ORGANISM: Artificial Sequence
<220> FEATURE:
<223> OTHER INFORMATION: ISOP121HR5P1G9

<400> SEQUENCE: 34

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
            20                  25                  30

Ile Asn Tyr Gly Glu Arg Ala Thr Lys Gly Glu Ala Ile Asn Leu Tyr
        35                  40                  45

Val Pro Gly Ser Glu Arg Ser Tyr Asp Leu Thr Gly Leu Lys Pro Gly
    50                  55                  60

Thr Glu Tyr Trp Val Leu Ile Gly Gly Val Lys Gly Leu Lys Ser
65                  70                  75                  80

Ser Pro Leu Trp Ala Trp Phe Thr Thr
                85
```

<210> SEQ ID NO 35
<211> LENGTH: 94
<212> TYPE: PRT
<213> ORGANISM: Artificial Sequence
<220> FEATURE:
<223> OTHER INFORMATION: ISOP121BR5P1F7

<400> SEQUENCE: 35

```
Leu Pro Ala Pro Lys Asn Leu Val Val Ser Arg Val Thr Glu Asp Ser
1               5                   10                  15

Ala Arg Leu Ser Trp His Asp Ala Thr Trp Gln Tyr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Phe His Arg Lys His
65                  70                  75                  80

Ile Asp Phe Val Ser Asn Pro Leu Ser Ala Ile Phe Thr Thr
                85                  90
```

<210> SEQ ID NO 36
<211> LENGTH: 94
<212> TYPE: PRT
<213> ORGANISM: Artificial Sequence
<220> FEATURE:
<223> OTHER INFORMATION: ISOP121BR5P1A6

<400> SEQUENCE: 36

```
Leu Pro Ala Pro Lys Asn Leu Val Val Ser Arg Val Thr Glu Asp Ser
1               5                   10                  15

Ala Arg Leu Ser Trp Ala Ser Trp Leu Val Ala Phe Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
```

```
                    50                  55                  60
Gly Thr Glu Tyr Thr Val Ser Ile Tyr Gly Val Tyr Gln Arg His Ala
 65                  70                  75                  80

Ser Ala Phe Val Ser Asn Pro Leu Ser Ala Ile Phe Thr Thr
                    85                  90
```

<210> SEQ ID NO 37
<211> LENGTH: 95
<212> TYPE: PRT
<213> ORGANISM: Artificial Sequence
<220> FEATURE:
<223> OTHER INFORMATION: ISOP121BR5P1C5

<400> SEQUENCE: 37

```
Leu Pro Ala Pro Lys Asn Leu Val Val Ser Arg Val Thr Glu Asp Ser
 1               5                  10                  15

Ala Arg Leu Ser Trp Phe Arg Leu Arg Ile Val Gln Thr Phe Asp Ser
                20                  25                  30

Phe Leu Ile Gln Tyr Gln Glu Ser Glu Lys Val Gly Glu Ala Ile Val
             35                  40                  45

Leu Thr Val Pro Gly Ser Glu Arg Ser Tyr Asp Leu Thr Gly Leu Lys
 50                  55                  60

Pro Gly Thr Glu Tyr Thr Val Ser Ile Tyr Gly Val Ile Thr Val Val
 65                  70                  75                  80

Glu Leu Leu Gln Gln Ser Asn Pro Leu Ser Ala Ile Phe Thr Thr
                    85                  90                  95
```

<210> SEQ ID NO 38
<211> LENGTH: 96
<212> TYPE: PRT
<213> ORGANISM: Artificial Sequence
<220> FEATURE:
<223> OTHER INFORMATION: ISOP121BR5P1D7

<400> SEQUENCE: 38

```
Leu Pro Ala Pro Lys Asn Leu Gly Cys Phe Ser Arg Tyr Arg Arg Leu
 1               5                  10                  15

Ser Arg Leu Ser Trp Glu Thr Pro Tyr Pro Ser Leu Ser Asn Phe Asp
                20                  25                  30

Ser Phe Leu Ile Gln Tyr Gln Glu Ser Glu Lys Val Gly Glu Ala Ile
             35                  40                  45

Val Leu Thr Val Pro Gly Ser Glu Arg Ser Tyr Asp Leu Thr Gly Leu
 50                  55                  60

Lys Pro Gly Thr Glu Tyr Thr Val Ser Ile Tyr Gly Val Leu Lys Leu
 65                  70                  75                  80

Ser Ala Ala Trp Trp Pro Ser Asn Pro Leu Ser Ala Ile Phe Thr Thr
                    85                  90                  95
```

<210> SEQ ID NO 39
<211> LENGTH: 93
<212> TYPE: PRT
<213> ORGANISM: Artificial Sequence
<220> FEATURE:
<223> OTHER INFORMATION: ISOP121BR5P1C6

<400> SEQUENCE: 39

```
Leu Pro Ala Pro Lys Asn Leu Val Val Ser Arg Val Thr Glu Asp Ser
 1               5                  10                  15

Ala Arg Leu Ser Trp Arg Lys Gln Glu Gln Tyr Phe Asp Ser Phe Leu
                20                  25                  30
```

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Tyr Ser Arg Pro Lys Ala
65                  70                  75                  80

Glu Phe Thr Ser Asn Pro Leu Ser Ala Ile Phe Thr Thr
                85                  90

<210> SEQ ID NO 40
<211> LENGTH: 93
<212> TYPE: PRT
<213> ORGANISM: Artificial Sequence
<220> FEATURE:
<223> OTHER INFORMATION: ISOP121AR5P1G6

<400> SEQUENCE: 40

Leu Pro Ala Pro Lys Asn Leu Val Val Ser Arg Val Thr Glu Asp Ser
1               5                   10                  15

Ala Arg Leu Ser Trp His Ala Thr Phe Gly Asp Pro Phe Asp Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
                85                  90

<210> SEQ ID NO 41
<211> LENGTH: 93
<212> TYPE: PRT
<213> ORGANISM: Artificial Sequence
<220> FEATURE:
<223> OTHER INFORMATION: ISOP121BR5P1B7

<400> SEQUENCE: 41

Leu Pro Ala Pro Lys Asn Leu Val Val Ser Arg Ile Thr Glu Asp Ser
1               5                   10                  15

Ala Arg Leu Ser Trp Lys Trp Glu Glu Gly Phe Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Tyr Gln Arg His Ala Ser
65                  70                  75                  80

Ala Phe Val Ser Asn Pro Leu Ser Ala Ile Phe Thr Thr
                85                  90

<210> SEQ ID NO 42
<211> LENGTH: 89
<212> TYPE: PRT
<213> ORGANISM: Artificial Sequence
<220> FEATURE:
<223> OTHER INFORMATION: ISOP121FR5P1G1

<400> SEQUENCE: 42

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile His Tyr Thr Glu Ala Pro Val His Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Val Ile Trp Gly Val Lys Gly Thr Trp Ser
65                  70                  75                  80

Ser Pro Leu Ser Ala Ile Phe Thr Thr
                85
```

<210> SEQ ID NO 43
<211> LENGTH: 89
<212> TYPE: PRT
<213> ORGANISM: Artificial Sequence
<220> FEATURE:
<223> OTHER INFORMATION: ISOP121GR5P1B4

<400> SEQUENCE: 43

```
Leu Pro Ala Pro Lys Asn Leu Ile Val Ser Arg Val Thr Glu Asp Ser
1               5                   10                  15

Ala Arg Leu Ser Trp Thr Ala Pro Asp Ala Ala Phe Asp Ser Phe Pro
            20                  25                  30

Ile Asn Tyr Gly Glu Arg Ala Thr Lys Gly Glu Ala Ile Asn Leu Tyr
            35                  40                  45

Val Pro Gly Ser Glu Arg Ser Tyr Asp Leu Thr Gly Leu Lys Pro Gly
    50                  55                  60

Thr Glu Tyr Trp Val Leu Ile Gly Gly Val Lys Gly Gly Leu Lys Ser
65                  70                  75                  80

Ser Pro Leu Trp Ala Trp Phe Thr Thr
                85
```

<210> SEQ ID NO 44
<211> LENGTH: 97
<212> TYPE: PRT
<213> ORGANISM: Artificial Sequence
<220> FEATURE:
<223> OTHER INFORMATION: ISOP121BR5P1G2

<400> SEQUENCE: 44

```
Leu Pro Ala Pro Lys Asn Leu Val Val Ser Arg Val Thr Glu Asp Ser
1               5                   10                  15

Ala Arg Leu Ser Trp Ala Asp Glu Leu His His Ala Asn His Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Tyr Asp Arg
65                  70                  75                  80

His Tyr Glu Ile His Phe Tyr Ser Asn Pro Leu Ser Ala Ile Phe Thr
                85                  90                  95

Thr
```

<210> SEQ ID NO 45
<211> LENGTH: 89

```
<212> TYPE: PRT
<213> ORGANISM: Artificial Sequence
<220> FEATURE:
<223> OTHER INFORMATION: ISOP121HR5P1H2

<400> SEQUENCE: 45

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Leu Glu Tyr Asp Tyr Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Asp Val Leu Ile Ile Gly Val Lys Gly Gly Ser Leu Ser
65                  70                  75                  80

Thr Pro Leu Ser Ala Ile Phe Thr Thr
                85

<210> SEQ ID NO 46
<211> LENGTH: 89
<212> TYPE: PRT
<213> ORGANISM: Artificial Sequence
<220> FEATURE:
<223> OTHER INFORMATION: ISOP121FR5P1G11

<400> SEQUENCE: 46

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Trp Tyr Leu Glu Ile Val Ala His Gly Gly Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Glu Val Ile Ile His Gly Val Lys Gly Cys Gly Pro Ser
65                  70                  75                  80

Gly Pro Leu Ser Ala Ile Phe Thr Thr
                85

<210> SEQ ID NO 47
<211> LENGTH: 94
<212> TYPE: PRT
<213> ORGANISM: Artificial Sequence
<220> FEATURE:
<223> OTHER INFORMATION: ISOP121AR5P1E7

<400> SEQUENCE: 47

Leu Pro Ala Pro Lys Asn Leu Val Val Ser Arg Val Thr Glu Asp Ser
1               5                   10                  15

Ala Arg Leu Ser Trp His Val Tyr His Glu Ile Asp Tyr Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr Gln Arg Lys
65                  70                  75                  80

Val Glu Phe Tyr Ser Asn Pro Leu Ser Ala Ile Phe Thr Thr
```

```
                        85                  90

<210> SEQ ID NO 48
<211> LENGTH: 91
<212> TYPE: PRT
<213> ORGANISM: Artificial Sequence
<220> FEATURE:
<223> OTHER INFORMATION: ISOP121GR5P1F6

<400> SEQUENCE: 48

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Arg Tyr His Glu Tyr Thr Trp Pro Gly Glu Ala Ile Val Leu Leu
        35                  40                  45

Val Pro Gly Ser Glu Arg Ser Tyr Asp Leu Thr Gly Leu Lys Pro Gly
    50                  55                  60

Thr Glu Tyr Gly Val Tyr Ile Asn Gly Val Lys Gly Gly Phe Arg Ser
65                  70                  75                  80

Lys Pro Leu Phe Ala Trp Phe Thr Thr Gly Gly
                85                  90

<210> SEQ ID NO 49
<211> LENGTH: 94
<212> TYPE: PRT
<213> ORGANISM: Artificial Sequence
<220> FEATURE:
<223> OTHER INFORMATION: ISOP121BR5P1E9

<400> SEQUENCE: 49

Leu Pro Ala Pro Lys Asn Leu Val Val Ser Arg Val Thr Glu Asp Ser
1               5                   10                  15

Ala Arg Leu Ser Trp Asp Ser Tyr Arg Asp Tyr Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Tyr Ser Arg Lys His Val
65                  70                  75                  80

Val Phe Val Gln Ser Asn Pro Leu Ser Ala Ile Phe Thr Thr
                85                  90

<210> SEQ ID NO 50
<211> LENGTH: 95
<212> TYPE: PRT
<213> ORGANISM: Artificial Sequence
<220> FEATURE:
<223> OTHER INFORMATION: ISOP121AR5P1F2

<400> SEQUENCE: 50

Leu Pro Ala Pro Lys Asn Leu Val Ile Ser Arg Val Thr Glu Asp Ser
1               5                   10                  15

Ala Arg Leu Ser Trp Gly Trp Ser Glu Leu Ile Ala Thr His Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60
```

-continued

Lys Pro Gly Thr Glu Tyr Thr Val Ser Ile Tyr Gly Val Tyr Asn Arg
65                  70                  75                  80

Lys Val Asn Phe Tyr Ser Asn Pro Leu Ser Ala Ile Phe Thr Thr
            85                  90                  95

<210> SEQ ID NO 51
<211> LENGTH: 95
<212> TYPE: PRT
<213> ORGANISM: Artificial Sequence
<220> FEATURE:
<223> OTHER INFORMATION: ISOP121AR5P1F7

<400> SEQUENCE: 51

Leu Pro Ala Pro Lys Asn Leu Val Val Ser Arg Val Thr Glu Asp Ser
1               5                   10                  15

Ala Arg Leu Ser Trp Gln Glu His Trp Asp Thr Ser Ser Asn Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Ile Ser Ile Tyr Gly Val Tyr Asn Arg
65                  70                  75                  80

Lys Val Leu Phe Tyr Ser Asn Pro Leu Ser Ala Ile Phe Thr Thr
            85                  90                  95

<210> SEQ ID NO 52
<211> LENGTH: 94
<212> TYPE: PRT
<213> ORGANISM: Artificial Sequence
<220> FEATURE:
<223> OTHER INFORMATION: ISOP121BR5P1H6

<400> SEQUENCE: 52

Leu Pro Ala Pro Lys Asn Leu Val Val Ser Arg Val Thr Glu Asp Ser
1               5                   10                  15

Ala Arg Leu Ser Trp Gly Tyr Ile Asp Val Ser Tyr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Tyr Ser Arg Pro Lys
65                  70                  75                  80

Ala Glu Phe Thr Ser Asn Pro Leu Ser Ala Ile Phe Thr Thr
            85                  90

<210> SEQ ID NO 53
<211> LENGTH: 89
<212> TYPE: PRT
<213> ORGANISM: Artificial Sequence
<220> FEATURE:
<223> OTHER INFORMATION: ISOP121GR5P1A2

<400> SEQUENCE: 53

Leu Pro Ala Pro Lys Asn Leu Val Val Ser Arg Val Thr Glu Asp Ser
1               5                   10                  15

Ala Arg Leu Ser Trp Thr Ala Pro Asp Ala Phe Asp Ser Phe Lys
            20                  25                  30

```
Ile Gln Tyr Ile Glu Arg Tyr Ile Pro Gly Glu Ala Ile Gln Leu Asn
         35                  40                  45

Val Pro Gly Ser Glu Arg Ser Tyr Asp Leu Thr Gly Leu Lys Pro Gly
 50                  55                  60

Thr Glu Tyr Ser Val Ile Ile Pro Gly Val Lys Gly Arg Asn Ser
 65                  70                  75                  80

Phe Pro Leu Trp Ala Trp Phe Thr Thr
                 85
```

<210> SEQ ID NO 54
<211> LENGTH: 94
<212> TYPE: PRT
<213> ORGANISM: Artificial Sequence
<220> FEATURE:
<223> OTHER INFORMATION: ISOP121BR5P1D3

<400> SEQUENCE: 54

```
Leu Pro Ala Pro Lys Asn Leu Val Val Ser Arg Val Thr Glu Asp Ser
 1               5                  10                  15

Ala Arg Leu Ser Trp Tyr Glu Asp Asn Thr Glu Arg Phe Asp Ser Phe
                 20                  25                  30

Leu Ile Gln Tyr Gln Glu Ser Glu Lys Val Gly Glu Ala Ile Val Leu
         35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val Tyr Ile Arg Val Gln
 65                  70                  75                  80

Val Leu Trp Phe Ser Asn Pro Leu Ser Ala Ile Phe Thr Thr
                 85                  90
```

<210> SEQ ID NO 55
<211> LENGTH: 95
<212> TYPE: PRT
<213> ORGANISM: Artificial Sequence
<220> FEATURE:
<223> OTHER INFORMATION: ISOP121AR5P1F9

<400> SEQUENCE: 55

```
Leu Pro Ala Pro Lys Asn Leu Val Val Ser Arg Val Thr Glu Asp Ser
 1               5                  10                  15

Ala Arg Leu Ser Trp Gly Trp Ser Glu Leu Ile Ala Thr His Phe Asp
                 20                  25                  30

Ser Phe Leu Ile Gln Tyr Gln Glu Ser Glu Lys Val Gly Glu Ala Ile
         35                  40                  45

Val Leu Thr Val Pro Gly Ser Glu Arg Ser Tyr Asp Leu Thr Gly Leu
 50                  55                  60

Lys Pro Gly Thr Glu Tyr Thr Val Ser Ile Tyr Gly Val Tyr Asn Arg
 65                  70                  75                  80

Lys Val Asn Phe Tyr Ser Asn Pro Leu Ser Ala Ile Phe Thr Thr
                 85                  90                  95
```

<210> SEQ ID NO 56
<211> LENGTH: 93
<212> TYPE: PRT
<213> ORGANISM: Artificial Sequence
<220> FEATURE:
<223> OTHER INFORMATION: ISOP121AR5P1H5

<400> SEQUENCE: 56

```
Leu Pro Ala Pro Lys Asn Leu Val Val Ser Arg Val Thr Glu Asp Ser
```

```
                1               5                  10                 15
Ala Arg Leu Ser Trp Glu Asp Ala Val Lys His Ile Trp Phe Asp Ser
                20                 25                 30

Phe Leu Ile Gln Tyr Gln Glu Ser Glu Lys Val Gly Glu Ala Ile Val
            35                 40                 45

Leu Thr Val Pro Gly Ser Glu Arg Ser Tyr Asp Leu Thr Gly Leu Lys
        50                 55                 60

Pro Gly Thr Glu Tyr Thr Val Ser Ile Tyr Gly Val Trp Ile Ala Ser
65                 70                 75                 80

Val Trp Arg Ser Asn Pro Leu Ser Ala Ile Phe Thr Thr
                85                 90

<210> SEQ ID NO 57
<211> LENGTH: 92
<212> TYPE: PRT
<213> ORGANISM: Artificial Sequence
<220> FEATURE:
<223> OTHER INFORMATION: ISOP121AR5P1G10

<400> SEQUENCE: 57

Leu Pro Ala Pro Lys Asn Leu Val Val Ser Arg Val Thr Glu Asp Ser
1               5                  10                 15

Ala Arg Leu Ser Trp Glu Trp Leu Glu His Phe Asp Ser Phe Leu Ile
                20                 25                 30

Gln Tyr Gln Glu Ser Glu Lys Val Gly Glu Ala Ile Val Leu Thr Val
            35                 40                 45

Pro Gly Ser Glu Arg Ser Tyr Asp Leu Thr Gly Leu Lys Pro Gly Thr
        50                 55                 60

Glu Tyr Thr Val Ser Ile Tyr Gly Val Tyr Gln Arg Lys Val Glu Phe
65                 70                 75                 80

His Ser Asn Pro Leu Ser Ala Ile Phe Thr Thr Thr
                85                 90

<210> SEQ ID NO 58
<211> LENGTH: 94
<212> TYPE: PRT
<213> ORGANISM: Artificial Sequence
<220> FEATURE:
<223> OTHER INFORMATION: ISOP121AR5P1F3

<400> SEQUENCE: 58

Leu Pro Ala Pro Lys Asn Leu Val Val Ser Arg Val Thr Glu Asp Ser
1               5                  10                 15

Ala Arg Leu Ser Trp Pro Phe Asn Asn Tyr Ser Glu His Phe Asp Ser
                20                 25                 30

Phe Leu Ile Gln Tyr Gln Glu Ser Glu Lys Val Gly Glu Ala Ile Val
            35                 40                 45

Leu Thr Val Pro Gly Ser Glu Arg Ser Tyr Asp Leu Thr Gly Leu Lys
        50                 55                 60

Pro Gly Thr Glu Tyr Thr Val Ser Ile Tyr Gly Val Tyr Glu Arg Lys
65                 70                 75                 80

Thr Ala Phe Tyr Ser Asn Pro Leu Ser Ala Ile Phe Thr Thr
                85                 90

<210> SEQ ID NO 59
<211> LENGTH: 94
<212> TYPE: PRT
<213> ORGANISM: Artificial Sequence
<220> FEATURE:
```

<223> OTHER INFORMATION: ISOP121BR5P1E2

<400> SEQUENCE: 59

Leu Pro Ala Pro Lys Asn Leu Val Val Ser Arg Val Thr Glu Asp Ser
1               5                   10                  15

Ala Arg Leu Ser Trp Trp Phe Pro Leu Glu Trp Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Tyr Thr Arg Glu His Lys
65                  70                  75                  80

Ser Val Trp Ala Ser Asn Pro Leu Ser Ala Ile Phe Thr Thr
                85                  90

<210> SEQ ID NO 60
<211> LENGTH: 93
<212> TYPE: PRT
<213> ORGANISM: Artificial Sequence
<220> FEATURE:
<223> OTHER INFORMATION: ISOP121BR5P1D1

<400> SEQUENCE: 60

Leu Pro Ala Pro Lys Asn Leu Val Val Ser Arg Val Thr Glu Asp Ser
1               5                   10                  15

Ala Arg Leu Ser Trp Lys Trp Gly Gly Glu Phe Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Tyr Gln Arg Asn Trp His
65                  70                  75                  80

His Trp Tyr Ser Asn Pro Leu Ser Ala Ile Phe Thr Thr
                85                  90

<210> SEQ ID NO 61
<211> LENGTH: 95
<212> TYPE: PRT
<213> ORGANISM: Artificial Sequence
<220> FEATURE:
<223> OTHER INFORMATION: ISOP121BR5P1C9

<400> SEQUENCE: 61

Leu Pro Ala Pro Lys Asn Leu Val Val Ser Arg Val Thr Glu Asp Ser
1               5                   10                  15

Ala Arg Leu Ser Trp Ile Trp Pro Asp Lys His Glu Phe Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr Asp Arg Lys
65                  70                  75                  80

Tyr Ala Asn Trp Ser Ser Asn Pro Leu Ser Ala Ile Phe Thr Thr
                85                  90                  95

```
<210> SEQ ID NO 62
<211> LENGTH: 89
<212> TYPE: PRT
<213> ORGANISM: Artificial Sequence
<220> FEATURE:
<223> OTHER INFORMATION: ISOP121GR5P1G11

<400> SEQUENCE: 62

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Asn Tyr His Glu Tyr Gly Gln Asn Gly Glu Ala Ile Gln Leu Ile
        35                  40                  45

Val Pro Gly Ser Glu Arg Ser Tyr Asp Leu Thr Gly Leu Lys Pro Gly
    50                  55                  60

Thr Glu Tyr Gly Val Trp Ile Trp Gly Val Lys Gly Ile Arg Ser
65                  70                  75                  80

Lys Pro Leu Trp Ala Phe Phe Thr Thr
                85

<210> SEQ ID NO 63
<211> LENGTH: 95
<212> TYPE: PRT
<213> ORGANISM: Artificial Sequence
<220> FEATURE:
<223> OTHER INFORMATION: ISOP121BR5P1A7

<400> SEQUENCE: 63

Leu Pro Ala Pro Lys Asn Leu Val Val Ser Arg Val Thr Glu Asp Ser
1               5                   10                  15

Ala Arg Leu Ser Trp Thr Thr Ala Phe His Asn Glu Tyr Phe Asp Ser
            20                  25                  30

Phe Leu Ile Gln Tyr Gln Glu Ser Gly Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr Ser Arg Pro
65                  70                  75                  80

Lys Ala Glu Phe Thr Ser Asn Pro Leu Ser Ala Ile Phe Thr Thr
                85                  90                  95

<210> SEQ ID NO 64
<211> LENGTH: 94
<212> TYPE: PRT
<213> ORGANISM: Artificial Sequence
<220> FEATURE:
<223> OTHER INFORMATION: ISOP121BR5P1C3

<400> SEQUENCE: 64

Leu Pro Ala Pro Lys Asn Leu Val Val Ser Arg Val Thr Glu Asp Ser
1               5                   10                  15

Ala Arg Leu Ser Trp Ala Ser Ala Arg Asp Tyr Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Leu Ala Ile Ala Gln Ile
65                  70                  75                  80
```

```
Thr His Trp Phe Ser Asn Pro Leu Ser Ala Ile Phe Thr Thr
            85                  90

<210> SEQ ID NO 65
<211> LENGTH: 91
<212> TYPE: PRT
<213> ORGANISM: Artificial Sequence
<220> FEATURE:
<223> OTHER INFORMATION: ISOP121AR5P1D11

<400> SEQUENCE: 65

Leu Pro Ala Pro Lys Asn Leu Val Val Ser Arg Val Thr Glu Asp Ser
1               5                   10                  15

Ala Arg Leu Ser Trp Glu Trp Leu Glu His Phe Asp Ser Phe Leu Ile
            20                  25                  30

Gln Tyr Gln Glu Ser Glu Lys Val Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Thr Val Ser Ile Tyr Gly Val Tyr Gln Arg Lys Val Glu Phe
65                  70                  75                  80

His Ser Asn Pro Leu Ser Ala Ile Phe Thr Thr
                85                  90

<210> SEQ ID NO 66
<211> LENGTH: 89
<212> TYPE: PRT
<213> ORGANISM: Artificial Sequence
<220> FEATURE:
<223> OTHER INFORMATION: ISOP121ER5P1E7

<400> SEQUENCE: 66

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Gly Tyr Thr Glu Thr Pro Pro Arg Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Lys Tyr Tyr Val Ser Ile Leu Gly Val Lys Gly Gly Leu Gly Ser
65                  70                  75                  80

Trp Pro Leu Ser Ala Ile Phe Thr Thr
                85

<210> SEQ ID NO 67
<211> LENGTH: 89
<212> TYPE: PRT
<213> ORGANISM: Artificial Sequence
<220> FEATURE:
<223> OTHER INFORMATION: ISOP121GR5P1G7

<400> SEQUENCE: 67

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Arg Tyr His Glu Tyr Asp Lys Asn Gly Glu Ala Ile Gln Leu Tyr
        35                  40                  45
```

```
Val Pro Gly Ser Glu Arg Ser Tyr Asp Leu Thr Gly Leu Lys Pro Gly
    50                  55                  60

Thr Glu Tyr Gly Val Tyr Ile His Gly Val Lys Gly Gly Gly Arg Ser
65                  70                  75                  80

Lys Pro Leu Trp Ala His Phe Thr Thr
                85

<210> SEQ ID NO 68
<211> LENGTH: 94
<212> TYPE: PRT
<213> ORGANISM: Artificial Sequence
<220> FEATURE:
<223> OTHER INFORMATION: ISOP121AR5P1A8

<400> SEQUENCE: 68

Leu Pro Ala Pro Lys Asn Leu Val Val Ser Arg Val Thr Glu Asp Ser
1               5                   10                  15

Ala Arg Leu Ser Trp Gly Leu Glu Trp Ala Tyr Gln Phe Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr Leu Arg Ala
65                  70                  75                  80

Ile Glu Phe Tyr Ser Asn Pro Leu Ser Ala Ile Phe Thr Thr
                85                  90

<210> SEQ ID NO 69
<211> LENGTH: 93
<212> TYPE: PRT
<213> ORGANISM: Artificial Sequence
<220> FEATURE:
<223> OTHER INFORMATION: ISOP121BR5P1E7

<400> SEQUENCE: 69

Leu Pro Ala Pro Lys Asn Leu Val Val Ser Arg Val Thr Glu Asp Ser
1               5                   10                  15

Ala Arg Leu Ser Trp Arg Lys Gln Glu Gln Tyr Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Lys Trp Pro Ser Thr
65                  70                  75                  80

Thr Thr Thr Ser Asn Pro Leu Ser Ala Ile Phe Thr Thr
                85                  90

<210> SEQ ID NO 70
<211> LENGTH: 89
<212> TYPE: PRT
<213> ORGANISM: Artificial Sequence
<220> FEATURE:
<223> OTHER INFORMATION: ISOP121FR5P1H8

<400> SEQUENCE: 70

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
```

```
                        20                  25                  30

Ile Tyr Tyr Ser Glu Gln His Phe Tyr Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Lys Ile Tyr Gly Val Lys Gly Gly Glu Thr Ser
65                  70                  75                  80

Lys Pro Leu Ser Ala Ile Phe Thr Thr
                85
```

<210> SEQ ID NO 71
<211> LENGTH: 89
<212> TYPE: PRT
<213> ORGANISM: Artificial Sequence
<220> FEATURE:
<223> OTHER INFORMATION: ISOP121GR5P1D2

<400> SEQUENCE: 71

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Leu Tyr Gln Glu Arg Ala Gln Ser Gly Glu Ala Ile Gly Leu Val
        35                  40                  45

Val Pro Gly Ser Glu Arg Ser Tyr Asp Leu Thr Gly Leu Lys Pro Ala
    50                  55                  60

Thr Glu Tyr Ser Val Gln Ile Phe Gly Val Lys Gly Lys Leu Ser
65                  70                  75                  80

Asn Pro Leu Trp Ala Trp Phe Thr Thr
                85
```

<210> SEQ ID NO 72
<211> LENGTH: 93
<212> TYPE: PRT
<213> ORGANISM: Artificial Sequence
<220> FEATURE:
<223> OTHER INFORMATION: ISOP121AR5P1H2

<400> SEQUENCE: 72

```
Leu Pro Ala Pro Lys Asn Leu Val Val Ser Arg Val Thr Glu Asp Ser
1               5                   10                  15

Ala Arg Leu Ser Trp Val Ile Asp Glu Phe Ile Pro Leu Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Leu Ala Lys Asn
65                  70                  75                  80

Ile Gly Ile Ser Asn Pro Leu Ser Ala Ile Phe Thr Thr
                85                  90
```

<210> SEQ ID NO 73
<211> LENGTH: 89
<212> TYPE: PRT
<213> ORGANISM: Artificial Sequence
<220> FEATURE:
<223> OTHER INFORMATION: ISOP121GR5P1F10

<400> SEQUENCE: 73

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
                20                  25                  30

Ile Asp Tyr Val Glu Arg Ala Thr Val Gly Glu Ala Ile Ala Leu Asn
            35                  40                  45

Val Pro Gly Ser Lys Arg Ser Tyr Ala Leu Thr Gly Leu Lys Pro Gly
        50                  55                  60

Thr Glu Tyr Phe Val Lys Ile Arg Gly Val Lys Gly Leu Lys Ser
65                  70                  75                  80

Lys Pro Leu Trp Ala Trp Phe Thr Thr
                85

<210> SEQ ID NO 74
<211> LENGTH: 93
<212> TYPE: PRT
<213> ORGANISM: Artificial Sequence
<220> FEATURE:
<223> OTHER INFORMATION: ISOP121BR5P1A2

<400> SEQUENCE: 74

Leu Pro Ala Pro Lys Asn Leu Val Val Ser Arg Val Thr Glu Asp Ser
1               5                   10                  15

Ala Arg Leu Ser Trp Arg Phe Ser Gln Glu Trp Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Tyr Ala Arg Gly Ile His
65                  70                  75                  80

Lys Trp Leu Ser Asn Pro Leu Ser Ala Ile Phe Thr Thr
                85                  90

<210> SEQ ID NO 75
<211> LENGTH: 89
<212> TYPE: PRT
<213> ORGANISM: Artificial Sequence
<220> FEATURE:
<223> OTHER INFORMATION: ISOP121GR5P1F7

<400> SEQUENCE: 75

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Asn Tyr Val Glu Arg Ala Ser Glu Gly Glu Ala Ile Asp Leu Gly
            35                  40                  45

Val Pro Gly Ser Glu Arg Ser Tyr Asp Leu Thr Gly Leu Lys Pro Gly
        50                  55                  60

Thr Glu Tyr Phe Val Lys Ile Phe Gly Val Lys Gly Ile Pro Ser
65                  70                  75                  80

Val Pro Leu Trp Ala Trp Phe Thr Thr
                85

<210> SEQ ID NO 76
<211> LENGTH: 93
<212> TYPE: PRT

```
<213> ORGANISM: Artificial Sequence
<220> FEATURE:
<223> OTHER INFORMATION: ISOP121AR5P1B8

<400> SEQUENCE: 76

Leu Pro Ala Pro Lys Asn Leu Val Ile Ser Arg Val Thr Glu Asp Ser
1               5                   10                  15

Ala Arg Leu Ser Trp Asp Lys Arg Thr Gln Phe Ala Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Pro Thr Trp Ser Gly
65                  70                  75                  80

Arg Thr Gln Ser Asn Pro Leu Ser Ala Ile Phe Thr Thr
                85                  90

<210> SEQ ID NO 77
<211> LENGTH: 89
<212> TYPE: PRT
<213> ORGANISM: Artificial Sequence
<220> FEATURE:
<223> OTHER INFORMATION: ISOP121GR5P1D7

<400> SEQUENCE: 77

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Lys
                20                  25                  30

Ile Trp Tyr Gln Glu Arg Ser Ile Val Gly Glu Ala Ile Phe Leu Leu
            35                  40                  45

Val Pro Gly Ser Glu Arg Ser Tyr Asp Leu Thr Gly Leu Lys Pro Gly
        50                  55                  60

Thr Glu Tyr Ile Val Gln Ile Phe Gly Val Lys Gly Pro Tyr Ser
65                  70                  75                  80

Asn Pro Leu Trp Ala Pro Phe Thr Thr
                85

<210> SEQ ID NO 78
<211> LENGTH: 94
<212> TYPE: PRT
<213> ORGANISM: Artificial Sequence
<220> FEATURE:
<223> OTHER INFORMATION: ISOP121BR5P1G3

<400> SEQUENCE: 78

Leu Pro Ala Pro Lys Asn Leu Val Val Ser Arg Val Thr Glu Asp Ser
1               5                   10                  15

Ala Arg Leu Ser Trp Lys Gln Arg Thr Ser Phe His Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Pro Phe Trp Gln Gln
65                  70                  75                  80

Trp Gln Pro Glu Ser Asn Pro Leu Ser Ala Ile Phe Thr Thr
                85                  90
```

```
<210> SEQ ID NO 79
<211> LENGTH: 93
<212> TYPE: PRT
<213> ORGANISM: Artificial Sequence
<220> FEATURE:
<223> OTHER INFORMATION: ISOP121AR5P1C5

<400> SEQUENCE: 79

Leu Pro Ala Pro Lys Asn Leu Val Val Ser Arg Val Thr Glu Asp Ser
1               5                   10                  15

Ala Arg Leu Ser Trp Lys Arg Ser Asp Asp Glu Trp Phe Asp Ser Phe
            20                  25                  30

Leu Ile Gln Tyr Gln Glu Ser Glu Lys Val Gly Glu Ala Ile Ile Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Tyr Gln Arg Ala Ala
65                  70                  75                  80

Leu Trp Phe Ser Asn Pro Leu Ser Ala Ile Phe Thr Thr
                85                  90

<210> SEQ ID NO 80
<211> LENGTH: 89
<212> TYPE: PRT
<213> ORGANISM: Artificial Sequence
<220> FEATURE:
<223> OTHER INFORMATION: ISOP121FR5P1H9

<400> SEQUENCE: 80

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Leu Tyr Gly Glu Thr Ala Pro Ile Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Tyr Ile Gln Gly Val Lys Gly Asn Tyr Ser
65                  70                  75                  80

Gln Pro Leu Ser Ala Ile Phe Thr Thr
                85

<210> SEQ ID NO 81
<211> LENGTH: 94
<212> TYPE: PRT
<213> ORGANISM: Artificial Sequence
<220> FEATURE:
<223> OTHER INFORMATION: ISOP121AR5P1A10

<400> SEQUENCE: 81

Leu Pro Ala Pro Lys Asn Leu Val Val Ser Arg Val Thr Glu Asp Ser
1               5                   10                  15

Ala Arg Leu Ser Trp Pro Asp Trp Ser Asn Ser Glu Tyr Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60
```

Pro Gly Thr Glu Tyr Thr Val Ser Ile Tyr Gly Val Tyr Ala Arg His
65                  70                  75                  80

Arg Leu Phe Val Ser Asn Pro Leu Ser Ala Ile Phe Thr Thr
                85                  90

<210> SEQ ID NO 82
<211> LENGTH: 89
<212> TYPE: PRT
<213> ORGANISM: Artificial Sequence
<220> FEATURE:
<223> OTHER INFORMATION: ISOP121HR5P1F2

<400> SEQUENCE: 82

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
                20                  25                  30

Ile Leu Tyr Gly Glu Thr Tyr Ser Gly Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Val Val Tyr Ile Phe Gly Val Lys Gly Lys Trp Ser
65                  70                  75                  80

Arg Pro Leu Ser Ala Ile Phe Thr Thr
                85

<210> SEQ ID NO 83
<211> LENGTH: 92
<212> TYPE: PRT
<213> ORGANISM: Artificial Sequence
<220> FEATURE:
<223> OTHER INFORMATION: ISOP121AR5P1H1

<400> SEQUENCE: 83

Leu Pro Ala Pro Lys Asn Leu Val Val Ser Arg Val Thr Glu Asp Ser
1               5                   10                  15

Ala Arg Leu Ser Trp Lys Gln Ala Thr Lys Phe Val Phe Asp Ser Phe
                20                  25                  30

Leu Ile Gln Tyr Gln Glu Ser Glu Lys Val Gly Glu Ala Ile Val Leu
                35                  40                  45

Thr Val Pro Gly Ser Glu Arg Ser Tyr Asp Leu Thr Gly Leu Lys Pro
            50                  55                  60

Gly Thr Glu Tyr Thr Val Ser Ile Tyr Gly Val Pro Asp Trp Phe Val
65                  70                  75                  80

Leu Glu Ser Asn Pro Leu Ser Ala Ile Phe Thr Thr
                85                  90

<210> SEQ ID NO 84
<211> LENGTH: 94
<212> TYPE: PRT
<213> ORGANISM: Artificial Sequence
<220> FEATURE:
<223> OTHER INFORMATION: ISOP121BR5P1D10

<400> SEQUENCE: 84

Leu Pro Ala Pro Lys Asn Leu Val Val Ser Arg Val Thr Glu Asp Ser
1               5                   10                  15

Ala Arg Leu Ser Trp Gly Lys Lys Ser His Phe Phe Asp Ser Phe Leu
                20                  25                  30

Ile Gln Tyr Gln Glu Ser Glu Lys Val Gly Glu Ala Ile Val Leu Thr

```
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Tyr Thr Arg Gly Gln Cys
65                  70                  75                  80

Glu Trp Glu Ser Asn Gln Leu Ser Ala Ile Phe Phe Thr Thr
                85                  90

<210> SEQ ID NO 85
<211> LENGTH: 93
<212> TYPE: PRT
<213> ORGANISM: Artificial Sequence
<220> FEATURE:
<223> OTHER INFORMATION: ISOP121BR5P1F10

<400> SEQUENCE: 85

Leu Pro Ala Pro Lys Asn Leu Val Val Ser Arg Val Thr Glu Asp Ser
1               5                   10                  15

Ala Arg Leu Ser Trp Pro Leu Asn Leu Glu Tyr Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Tyr Gly Arg Tyr Gly Gly
65                  70                  75                  80

Pro Phe Val Ser Asn Pro Leu Ser Ala Ile Phe Thr Thr
                85                  90

<210> SEQ ID NO 86
<211> LENGTH: 94
<212> TYPE: PRT
<213> ORGANISM: Artificial Sequence
<220> FEATURE:
<223> OTHER INFORMATION: ISOP121BR5P1D11

<400> SEQUENCE: 86

Leu Pro Ala Pro Lys Asn Leu Val Val Ser Arg Val Thr Glu Asp Ser
1               5                   10                  15

Ala Arg Leu Ser Trp Phe Asn Ala Asp Glu Glu Tyr Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val Tyr Val Arg Ala Val
65                  70                  75                  80

Arg Phe Val Ser Ser Asn Pro Leu Ser Ala Ile Phe Thr Thr
                85                  90

<210> SEQ ID NO 87
<211> LENGTH: 92
<212> TYPE: PRT
<213> ORGANISM: Artificial Sequence
<220> FEATURE:
<223> OTHER INFORMATION: ISOP121AR5P1E11

<400> SEQUENCE: 87

Leu Pro Ala Pro Lys Asn Leu Val Val Ser Arg Val Thr Glu Asp Ser
1               5                   10                  15
```

Ala Arg Leu Ser Trp Ser Val Gln Thr Ser Phe Val Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Pro Leu Trp His Gly
65                  70                  75                  80

Phe Asp Ser Asn Pro Leu Ser Ala Ile Phe Thr Thr
                85                  90

<210> SEQ ID NO 88
<211> LENGTH: 94
<212> TYPE: PRT
<213> ORGANISM: Artificial Sequence
<220> FEATURE:
<223> OTHER INFORMATION: ISOP121BR5P1D6

<400> SEQUENCE: 88

Leu Pro Ala Pro Lys Asn Leu Val Val Ser Arg Val Thr Glu Asp Ser
1               5                   10                  15

Ala Arg Leu Ser Trp Lys Gln Gly Thr Ser Phe His Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Gln Leu Leu Ala Asn
65                  70                  75                  80

Asp Ile Ile Ser Ser Asn Pro Leu Ser Ala Ile Phe Thr Thr
                85                  90

<210> SEQ ID NO 89
<211> LENGTH: 93
<212> TYPE: PRT
<213> ORGANISM: Artificial Sequence
<220> FEATURE:
<223> OTHER INFORMATION: ISOP121BR5P1B5

<400> SEQUENCE: 89

Leu Pro Ala Pro Lys Asn Leu Val Val Ser Arg Val Thr Glu Asp Ser
1               5                   10                  15

Ala Arg Leu Ser Trp Arg Lys Gln Glu Gln Tyr Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Tyr Gln Arg Gly Tyr His
65                  70                  75                  80

Asn Trp Phe Ser Asn Pro Leu Ser Ala Ile Phe Thr Thr
                85                  90

<210> SEQ ID NO 90
<211> LENGTH: 89
<212> TYPE: PRT
<213> ORGANISM: Artificial Sequence
<220> FEATURE:
<223> OTHER INFORMATION: ISOP194ER9P1G3

<400> SEQUENCE: 90

```
Leu Pro Ala Pro Lys Asn Leu Ile Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ala Tyr Tyr Glu Thr Met Val Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Ile Ile Lys Gly Val Lys Gly Lys Pro Ser
65                  70                  75                  80

Trp Pro Leu Ser Ala Ile Phe Thr Thr
                85
```

<210> SEQ ID NO 91
<211> LENGTH: 91
<212> TYPE: PRT
<213> ORGANISM: Artificial Sequence
<220> FEATURE:
<223> OTHER INFORMATION: ISOP194AR9P1F2

<400> SEQUENCE: 91

```
Leu Pro Ala Pro Lys Asn Leu Val Ile Ser Arg Val Thr Glu Asp Ser
1               5                   10                  15

Ala Arg Leu Ser Trp Glu Trp Leu Glu His Phe Asp Ser Phe Leu Ile
            20                  25                  30

Gln Tyr Gln Glu Ser Glu Lys Val Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Thr Val Ser Ile Tyr Gly Val Tyr Asn Arg Lys Val Asn Phe
65                  70                  75                  80

Tyr Ser Asn Pro Leu Ser Ala Ile Phe Thr Thr
                85                  90
```

<210> SEQ ID NO 92
<211> LENGTH: 94
<212> TYPE: PRT
<213> ORGANISM: Artificial Sequence
<220> FEATURE:
<223> OTHER INFORMATION: ISOP194AR9P1H10

<400> SEQUENCE: 92

```
Leu Pro Ala Pro Lys Asn Leu Val Ile Ser Arg Val Thr Glu Asp Ser
1               5                   10                  15

Ala Arg Leu Ser Trp Pro Ala His Tyr His Ser Ala Phe Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr Gln Arg Lys
65                  70                  75                  80

Val Glu Phe His Ser Asn Pro Leu Ser Ala Ile Phe Thr Thr
                85                  90
```

<210> SEQ ID NO 93

```
<211> LENGTH: 95
<212> TYPE: PRT
<213> ORGANISM: Artificial Sequence
<220> FEATURE:
<223> OTHER INFORMATION: ISOP194BR9P1H4

<400> SEQUENCE: 93

Leu Pro Ala Pro Lys Asn Leu Val Val Ser Arg Val Thr Glu Asp Ser
1               5                   10                  15

Ala Cys Leu Ser Trp Thr Thr Ala Phe His Asn Glu Tyr Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr Ser Arg Pro
65                  70                  75                  80

Lys Ala Glu Phe Thr Ser Asn Pro Leu Ser Ala Ile Phe Thr Thr
                85                  90                  95

<210> SEQ ID NO 94
<211> LENGTH: 92
<212> TYPE: PRT
<213> ORGANISM: Artificial Sequence
<220> FEATURE:
<223> OTHER INFORMATION: ISOP194AR9P1D8

<400> SEQUENCE: 94

Leu Pro Ala Pro Lys Asn Leu Val Val Ser Arg Val Thr Glu Asp Ser
1               5                   10                  15

Ala Arg Leu Ser Trp Asp Thr Trp Asn Asp Phe Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Tyr Gln Arg Lys Val Ile
65                  70                  75                  80

Trp Leu Ser Asn Pro Leu Ser Ala Ile Phe Thr Thr
                85                  90

<210> SEQ ID NO 95
<211> LENGTH: 96
<212> TYPE: PRT
<213> ORGANISM: Artificial Sequence
<220> FEATURE:
<223> OTHER INFORMATION: ISOP194BR9P1D1

<400> SEQUENCE: 95

Leu Pro Ala Pro Lys Asn Leu Val Val Ser Arg Val Thr Glu Asp Ser
1               5                   10                  15

Ala Arg Leu Ser Trp Glu His Ser Leu Asn Asp Gln Trp Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Tyr Gln Arg
65                  70                  75                  80
```

```
Gly Arg Ala Leu Trp Tyr Ser Asn Pro Leu Ser Ala Ile Phe Thr Thr
                85                  90                  95
```

<210> SEQ ID NO 96
<211> LENGTH: 91
<212> TYPE: PRT
<213> ORGANISM: Artificial Sequence
<220> FEATURE:
<223> OTHER INFORMATION: ISOP194AR9P1E8

<400> SEQUENCE: 96

```
Leu Pro Ala Pro Lys Asn Leu Val Val Ser Arg Val Thr Glu Asp Ser
1               5                   10                  15

Ala Arg Leu Ser Trp Glu Trp Leu Glu His Phe Asp Ser Phe Leu Ile
            20                  25                  30

Gln Tyr Gln Glu Ser Glu Lys Val Gly Glu Ala Ile Val Leu Thr Ile
        35                  40                  45

Pro Gly Ser Glu Arg Ser Tyr Asp Leu Thr Gly Leu Lys Pro Gly Thr
    50                  55                  60

Glu Tyr Thr Val Ser Ile Tyr Gly Val Tyr Gln Arg Lys Val Glu Phe
65                  70                  75                  80

His Ser Asn Pro Leu Ser Ala Ile Phe Thr Thr
                85                  90
```

<210> SEQ ID NO 97
<211> LENGTH: 91
<212> TYPE: PRT
<213> ORGANISM: Artificial Sequence
<220> FEATURE:
<223> OTHER INFORMATION: ISOP194AR9P1E9

<400> SEQUENCE: 97

```
Leu Pro Ala Pro Lys Asn Leu Val Val Ser Arg Val Thr Glu Asp Ser
1               5                   10                  15

Ala Arg Leu Ser Trp Glu Trp Leu Glu His Phe Asp Ser Phe Leu Ile
            20                  25                  30

Gln Tyr Gln Glu Ser Glu Lys Val Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Thr Val Ser Ile Tyr Gly Val Tyr Gln Arg Lys Val Asn Phe
65                  70                  75                  80

Tyr Ser Asn Pro Leu Ser Ala Ile Phe Thr Thr
                85                  90
```

<210> SEQ ID NO 98
<211> LENGTH: 91
<212> TYPE: PRT
<213> ORGANISM: Artificial Sequence
<220> FEATURE:
<223> OTHER INFORMATION: ISOP194AR9P1H9

<400> SEQUENCE: 98

```
Leu Pro Ala Pro Lys Asn Leu Val Val Ser Arg Val Thr Glu Asp Ser
1               5                   10                  15

Ala Arg Leu Ser Trp Glu Trp Leu Glu His Phe Asp Ser Phe Gln Ile
            20                  25                  30

Gln Tyr Gln Glu Ser Glu Lys Val Gly Glu Ala Ile Val Leu Thr Val
        35                  40                  45

Pro Gly Ser Glu Arg Ser Tyr Asp Leu Thr Gly Leu Lys Pro Gly Thr
```

Glu Tyr Thr Val Ser Ile Tyr Gly Val Tyr Gln Arg Lys Val Glu Phe
65                  70                  75                  80

His Ser Asn Pro Leu Ser Ala Ile Phe Thr Thr
                85                  90

<210> SEQ ID NO 99
<211> LENGTH: 94
<212> TYPE: PRT
<213> ORGANISM: Artificial Sequence
<220> FEATURE:
<223> OTHER INFORMATION: ISOP194BR9P1A9

<400> SEQUENCE: 99

Leu Pro Ala Pro Lys Asn Leu Val Val Ser Arg Val Thr Glu Asp Ser
1               5                   10                  15

Ala Arg Leu Ser Trp Phe Asn Ala Asp Glu Glu Tyr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Tyr Asp Arg Lys Val
65                  70                  75                  80

Lys Phe Val Gln Ser Asn Pro Leu Ser Ala Ile Phe Thr Thr
                85                  90

<210> SEQ ID NO 100
<211> LENGTH: 94
<212> TYPE: PRT
<213> ORGANISM: Artificial Sequence
<220> FEATURE:
<223> OTHER INFORMATION: ISOP194BR9P1A5

<400> SEQUENCE: 100

Leu Pro Ala Pro Lys Asn Leu Val Val Ser Arg Val Thr Glu Asp Ser
1               5                   10                  15

Ala Arg Leu Ser Trp Phe Asn Ala Asp Glu Glu Tyr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Tyr Gln Arg Gly Tyr
65                  70                  75                  80

His Asn Trp Phe Ser Asn Pro Leu Ser Ala Ile Phe Thr Thr
                85                  90

<210> SEQ ID NO 101
<211> LENGTH: 95
<212> TYPE: PRT
<213> ORGANISM: Artificial Sequence
<220> FEATURE:
<223> OTHER INFORMATION: ISOP194BR9P1F7

<400> SEQUENCE: 101

Leu Pro Ala Pro Lys Asn Leu Val Val Ser Arg Val Thr Glu Asp Ser
1               5                   10                  15

Ala Arg Leu Ser Trp Phe Asn Ala Asp Glu Glu Tyr Phe Asp Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val Tyr Thr Arg Gly Arg
 65                  70                  75                  80

Tyr Glu Trp Arg Glu Ser Asn Pro Leu Ser Ala Ile Phe Thr Thr
             85                  90                  95

<210> SEQ ID NO 102
<211> LENGTH: 94
<212> TYPE: PRT
<213> ORGANISM: Artificial Sequence
<220> FEATURE:
<223> OTHER INFORMATION: ISOP194AR9P1G7

<400> SEQUENCE: 102

Leu Pro Ala Pro Lys Asn Leu Val Val Ser Arg Val Thr Glu Asp Ser
 1               5                  10                  15

Ala Arg Leu Ser Trp Gly Asp Asp Phe Asn Ser Glu Tyr Phe Asp Ser
             20                  25                  30

Phe Leu Ile Gln Tyr Gln Glu Ser Glu Lys Val Gly Glu Ala Ile Val
         35                  40                  45

Leu Thr Val Pro Gly Ser Glu Arg Ser Tyr Asp Leu Thr Gly Leu Lys
     50                  55                  60

Pro Gly Thr Glu Tyr Thr Val Ser Ile Tyr Gly Val Tyr Thr Arg Ala
 65                  70                  75                  80

Val Val Phe Thr Ser Asn Pro Leu Ser Ala Ile Phe Thr Thr
             85                  90

<210> SEQ ID NO 103
<211> LENGTH: 93
<212> TYPE: PRT
<213> ORGANISM: Artificial Sequence
<220> FEATURE:
<223> OTHER INFORMATION: ISOP194AR9P1E3

<400> SEQUENCE: 103

Leu Pro Ala Pro Lys Asn Leu Val Val Ser Arg Val Thr Glu Asp Ser
 1               5                  10                  15

Ala Arg Leu Ser Trp Lys Arg Ser Asp Asp Glu Trp Phe Asp Ser Phe
             20                  25                  30

Leu Ile Gln Tyr Gln Glu Ser Glu Lys Val Gly Glu Ala Ile Val Leu
         35                  40                  45

Thr Val Pro Gly Ser Glu Arg Ser Tyr Asp Leu Thr Gly Leu Lys Pro
     50                  55                  60

Gly Thr Glu Tyr Thr Val Ser Ile Tyr Gly Val Tyr Gln Arg Ala Ala
 65                  70                  75                  80

Leu Trp Phe Ser Asn Pro Leu Ser Ala Ile Phe Thr Thr
             85                  90

<210> SEQ ID NO 104
<211> LENGTH: 95
<212> TYPE: PRT
<213> ORGANISM: Artificial Sequence
<220> FEATURE:
<223> OTHER INFORMATION: ISOP194AR9P1C5

<400> SEQUENCE: 104

-continued

Leu Pro Ala Pro Lys Asn Leu Val Val Ser Arg Val Thr Glu Asp Ser
1               5                   10                  15

Ala Arg Leu Ser Trp Leu Arg Asp Phe Asn Gly Arg Ala Phe Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Pro Thr Gly Leu
    50                  55                  60

Lys Pro Gly Thr Glu Tyr Thr Val Ser Ile Tyr Gly Val Phe Ile Thr
65                  70                  75                  80

Trp Ile His Val Arg Ser Asn Pro Leu Ser Ala Ile Phe Thr Thr
                85                  90                  95

<210> SEQ ID NO 105
<211> LENGTH: 95
<212> TYPE: PRT
<213> ORGANISM: Artificial Sequence
<220> FEATURE:
<223> OTHER INFORMATION: ISOP194AR9P1H3

<400> SEQUENCE: 105

Leu Pro Ala Pro Lys Asn Leu Val Val Ser Arg Val Thr Glu Asp Ser
1               5                   10                  15

Ala Arg Leu Ser Trp Asn Ala Ser Trp Ile Ser His Asn Phe Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Tyr Glu Arg
65                  70                  75                  80

Lys Thr Ala Phe Tyr Ser Asn Pro Leu Ser Ala Ile Phe Thr Thr
                85                  90                  95

<210> SEQ ID NO 106
<211> LENGTH: 89
<212> TYPE: PRT
<213> ORGANISM: Artificial Sequence
<220> FEATURE:
<223> OTHER INFORMATION: ISOP194GR9P1E9

<400> SEQUENCE: 106

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Arg Tyr His Glu Tyr Asp Lys Asn Gly Glu Ala Ile Gln Leu Tyr
            35                  40                  45

Val Pro Gly Ser Glu Arg Ser Tyr Asp Leu Thr Gly Leu Lys Pro Gly
    50                  55                  60

Thr Glu Tyr Gly Val Phe Ile Trp Gly Val Lys Gly Leu Lys Ser
65                  70                  75                  80

Lys Pro Leu Trp Ala Trp Phe Thr Thr
                85

<210> SEQ ID NO 107
<211> LENGTH: 88
<212> TYPE: PRT
<213> ORGANISM: Artificial Sequence

<220> FEATURE:
<223> OTHER INFORMATION: ISOP194HR9P1B10

<400> SEQUENCE: 107

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
            20                  25                  30

Ile Arg Tyr Tyr Glu Arg Ala Asn Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Ile Val Trp Ile Tyr Gly Val Lys Gly Gly Arg Ser Gly
65                  70                  75                  80

Pro Leu Ser Ala Ile Phe Thr Thr
                85

<210> SEQ ID NO 108
<211> LENGTH: 89
<212> TYPE: PRT
<213> ORGANISM: Artificial Sequence
<220> FEATURE:
<223> OTHER INFORMATION: ISOP194ER9P1A11

<400> SEQUENCE: 108

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ala Tyr Tyr Glu Thr Met Val Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Ile Ile Lys Gly Val Lys Gly Gly Lys Pro Ser
65                  70                  75                  80

Trp Pro Leu Ser Ala Ile Phe Thr Thr
                85

<210> SEQ ID NO 109
<211> LENGTH: 89
<212> TYPE: PRT
<213> ORGANISM: Artificial Sequence
<220> FEATURE:
<223> OTHER INFORMATION: ISOP194ER9P1A3

<400> SEQUENCE: 109

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ala Tyr Tyr Glu Thr Met Val Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Ile Ile Lys Gly Val Lys Gly Gly Met Val Ser
65                  70                  75                  80

Trp Pro Leu Ser Ala Ile Phe Thr Thr
                85

```
<210> SEQ ID NO 110
<211> LENGTH: 89
<212> TYPE: PRT
<213> ORGANISM: Artificial Sequence
<220> FEATURE:
<223> OTHER INFORMATION: ISOP194ER9P1H9

<400> SEQUENCE: 110

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ala Tyr Tyr Glu Thr Met Val Ser Gly Ala Ile Val Leu Thr
        35                  40                  45

Val Pro Gly Ser Glu Arg Ser Tyr Asp Leu Thr Gly Pro Lys Pro Gly
    50                  55                  60

Thr Glu Tyr Ala Val Ile Ile Lys Gly Val Lys Gly Lys Pro Ser
65                  70                  75                  80

Trp Pro Leu Ser Ala Ile Phe Thr Thr
                85

<210> SEQ ID NO 111
<211> LENGTH: 89
<212> TYPE: PRT
<213> ORGANISM: Artificial Sequence
<220> FEATURE:
<223> OTHER INFORMATION: ISOP194HR9P1B2

<400> SEQUENCE: 111

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Leu Tyr Gly Glu Leu Ile Gly Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Ser Glu Tyr Thr Val Tyr Ile Phe Gly Val Lys Gly Gly Arg Tyr Ser
65                  70                  75                  80

Arg Pro Leu Ser Ala Ile Phe Thr Thr
                85

<210> SEQ ID NO 112
<211> LENGTH: 89
<212> TYPE: PRT
<213> ORGANISM: Artificial Sequence
<220> FEATURE:
<223> OTHER INFORMATION: ISOP194HR9P1D11

<400> SEQUENCE: 112

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Leu Tyr Gly Glu Leu Ile Gly Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Tyr Ile Phe Gly Val Lys Gly Gly Arg Tyr Ser
```

65                  70                  75                  80

Arg Pro Leu Ser Ala Ile Phe Thr Thr
                85

<210> SEQ ID NO 113
<211> LENGTH: 89
<212> TYPE: PRT
<213> ORGANISM: Artificial Sequence
<220> FEATURE:
<223> OTHER INFORMATION: ISOP194GR9P1F6

<400> SEQUENCE: 113

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Asp Tyr Trp Glu Arg Leu Ser Glu Gly Glu Ala Ile Ala Leu Arg
        35                  40                  45

Val Pro Gly Ser Glu Arg Ser Tyr Asp Leu Thr Gly Leu Lys Pro Gly
    50                  55                  60

Thr Glu Tyr Tyr Val Trp Ile Val Gly Val Lys Gly Lys Phe Ser
65                  70                  75                  80

Gln Pro Leu Arg Ala Trp Phe Thr Thr
                85

<210> SEQ ID NO 114
<211> LENGTH: 89
<212> TYPE: PRT
<213> ORGANISM: Artificial Sequence
<220> FEATURE:
<223> OTHER INFORMATION: ISOP194GR9P1F9

<400> SEQUENCE: 114

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Phe Tyr Asn Glu Arg Trp Gln Asn Gly Glu Ala Ile Arg Leu Ile
        35                  40                  45

Val Pro Gly Ser Glu Arg Ser Tyr Asp Leu Thr Gly Leu Lys Pro Gly
    50                  55                  60

Thr Glu Tyr Ser Val Ile Ile Pro Gly Val Lys Gly Gly Arg Asn Ser
65                  70                  75                  80

Phe Pro Leu Trp Ala Trp Phe Thr Thr
                85

<210> SEQ ID NO 115
<211> LENGTH: 89
<212> TYPE: PRT
<213> ORGANISM: Artificial Sequence
<220> FEATURE:
<223> OTHER INFORMATION: ISOP194GR9P1C11

<400> SEQUENCE: 115

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Phe Tyr Asn Glu Arg Trp Gln Asn Gly Glu Ala Ile Arg Leu Thr
        35                  40                  45

Val Pro Gly Ser Glu Arg Ser Tyr Asp Leu Thr Gly Leu Lys Pro Gly
            50                  55                  60

Thr Glu Tyr Trp Val Leu Ile Gly Gly Val Lys Gly Gly Leu Lys Ser
 65                  70                  75                  80

Ser Pro Leu Trp Ala Trp Phe Thr Thr
                85

<210> SEQ ID NO 116
<211> LENGTH: 89
<212> TYPE: PRT
<213> ORGANISM: Artificial Sequence
<220> FEATURE:
<223> OTHER INFORMATION: ISOP194ER9P1E6

<400> SEQUENCE: 116

Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Trp
                 20                  25                  30

Ile Lys Tyr Tyr Glu Lys Arg Asn Pro Gly Glu Ala Ile Val Leu Thr
             35                  40                  45

Val Pro Gly Ser Glu Arg Ser Tyr Asp Leu Thr Gly Leu Lys Pro Gly
          50                  55                  60

Thr Glu Tyr Leu Val Ile Ile Ser Gly Val Lys Gly Ser Arg Ser
 65                  70                  75                  80

Val Pro Leu Ser Ala Ile Phe Thr Thr
                85

<210> SEQ ID NO 117
<211> LENGTH: 95
<212> TYPE: PRT
<213> ORGANISM: Artificial Sequence
<220> FEATURE:
<223> OTHER INFORMATION: ISOP194BR9P1G9

<400> SEQUENCE: 117

Leu Pro Ala Pro Lys Asn Leu Val Val Ser Arg Val Thr Glu Asp Ser
  1               5                  10                  15

Ala Arg Leu Ser Trp Thr Thr Ala Phe His Asn Glu Tyr Phe Asp Ser
                 20                  25                  30

Phe Leu Ile Gln Tyr Gln Glu Ser Glu Lys Val Gly Glu Ala Ile Val
             35                  40                  45

Leu Thr Val Pro Gly Ser Glu Arg Ser Tyr Asp Leu Thr Gly Leu Lys
          50                  55                  60

Pro Gly Thr Glu Tyr Thr Val Ser Ile Tyr Gly Val Tyr Ile Arg Val
 65                  70                  75                  80

Gln Val Leu Trp Phe Ser Asn Pro Leu Ser Ala Ile Phe Thr Thr
                85                  90                  95

<210> SEQ ID NO 118
<211> LENGTH: 95
<212> TYPE: PRT
<213> ORGANISM: Artificial Sequence
<220> FEATURE:
<223> OTHER INFORMATION: ISOP194BR9P1E4

<400> SEQUENCE: 118

Leu Pro Ala Pro Lys Asn Leu Val Val Ser Arg Val Thr Glu Asp Ser
  1               5                  10                  15

Ala Arg Leu Ser Trp Thr Thr Ala Phe His Asn Glu Tyr Phe Asp Ser
        20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr Gln Arg Gly
65                  70                  75                  80

Tyr His Asn Trp Phe Ser Asn Pro Leu Ser Ala Ile Phe Thr Thr
                85                  90                  95

<210> SEQ ID NO 119
<211> LENGTH: 95
<212> TYPE: PRT
<213> ORGANISM: Artificial Sequence
<220> FEATURE:
<223> OTHER INFORMATION: ISOP194AR9P1H1

<400> SEQUENCE: 119

Leu Pro Ala Pro Lys Asn Leu Val Val Ser Arg Val Thr Glu Asp Ser
1               5                   10                  15

Ala Arg Leu Ser Trp Trp Arg Val Leu Gly His Ser His Phe Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Tyr Asn Arg
65                  70                  75                  80

Lys Val Asn Phe Tyr Ser Asn Pro Leu Ser Ala Ile Phe Thr Thr
                85                  90                  95

<210> SEQ ID NO 120
<211> LENGTH: 94
<212> TYPE: PRT
<213> ORGANISM: Artificial Sequence
<220> FEATURE:
<223> OTHER INFORMATION: ISOP194BR9P1D10

<400> SEQUENCE: 120

Leu Pro Ala Pro Lys Asn Leu Val Val Ser Arg Val Thr Glu Asp Ser
1               5                   10                  15

Ala Arg Leu Ser Trp Tyr Glu Asp Asn Thr Glu Arg Phe Asp Ser Phe
            20                  25                  30

Leu Ile Gln Tyr Gln Glu Ser Glu Lys Val Val Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Tyr Ile Arg Val Gln
65                  70                  75                  80

Val Leu Trp Phe Ser Asn Pro Leu Ser Ala Ile Phe Thr Thr
                85                  90

<210> SEQ ID NO 121
<211> LENGTH: 94
<212> TYPE: PRT
<213> ORGANISM: Artificial Sequence
<220> FEATURE:
<223> OTHER INFORMATION: ISOP194BR9P1C8

-continued

```
<400> SEQUENCE: 121

Leu Pro Ala Pro Lys Asn Leu Val Val Ser Arg Val Thr Glu Asp Ser
1               5                   10                  15

Ala Arg Leu Ser Trp Tyr Phe Ala Gly Glu Leu Trp Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Tyr Gln Arg Gly Tyr
65                  70                  75                  80

His Asn Trp Phe Ser Asn Pro Leu Ser Ala Ile Phe Thr Thr
                85                  90

<210> SEQ ID NO 122
<211> LENGTH: 91
<212> TYPE: PRT
<213> ORGANISM: Artificial Sequence
<220> FEATURE:
<223> OTHER INFORMATION: ISOP194AR9P1C10

<400> SEQUENCE: 122

Leu Pro Ala Pro Lys Asn Leu Val Val Ser Arg Val Thr Glu Asp Ser
1               5                   10                  15

Ala Arg Pro Ser Trp Glu Trp Leu Glu His Phe Asp Ser Phe Leu Ile
            20                  25                  30

Gln Tyr Gln Glu Ser Glu Lys Val Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Thr Val Ser Ile Tyr Gly Val Tyr Asn Arg Lys Val Asn Phe
65                  70                  75                  80

Tyr Ser Asn Pro Leu Ser Ala Ile Phe Thr Thr
                85                  90

<210> SEQ ID NO 123
<211> LENGTH: 92
<212> TYPE: PRT
<213> ORGANISM: Artificial Sequence
<220> FEATURE:
<223> OTHER INFORMATION: ISOP194AR9P1D11

<400> SEQUENCE: 123

Leu Pro Ala Pro Lys Asn Leu Val Val Ser Arg Val Thr Glu Asp Ser
1               5                   10                  15

Gly Arg Leu Ser Trp Gln His His Ile Ser Phe Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Tyr Asn Arg Lys Val Asn
65                  70                  75                  80

Phe Tyr Ser Asn Pro Leu Ser Ala Ile Phe Thr Thr
                85                  90

<210> SEQ ID NO 124
<211> LENGTH: 91
```

```
<212> TYPE: PRT
<213> ORGANISM: Artificial Sequence
<220> FEATURE:
<223> OTHER INFORMATION: ISOP194AR9P1C3

<400> SEQUENCE: 124

Leu Pro Ala Pro Lys Asn Leu Val Val Ser Arg Val Thr Gln Asn Ser
1               5                   10                  15

Ala Arg Leu Ser Trp Glu Trp Leu Glu His Phe Asp Ser Phe Leu Ile
            20                  25                  30

His Tyr Gln Glu Ser Glu Lys Val Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Thr Val Ser Ile Tyr Gly Val Tyr Gln Arg Lys Val Glu Phe
65                  70                  75                  80

His Ser Asn Pro Leu Ser Ala Ile Phe Thr Thr
                85                  90

<210> SEQ ID NO 125
<211> LENGTH: 88
<212> TYPE: PRT
<213> ORGANISM: Homo sapiens

<400> SEQUENCE: 125

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
    50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85

<210> SEQ ID NO 126
<211> LENGTH: 89
<212> TYPE: PRT
<213> ORGANISM: Artificial Sequence
<220> FEATURE:
<223> OTHER INFORMATION: Fibcon

<400> SEQUENCE: 126

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85
```

```
<210> SEQ ID NO 127
<211> LENGTH: 94
<212> TYPE: PRT
<213> ORGANISM: Homo sapiens

<400> SEQUENCE: 127

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 128
<211> LENGTH: 4
<212> TYPE: PRT
<213> ORGANISM: Artificial Sequence
<220> FEATURE:
<223> OTHER INFORMATION: Linker

<400> SEQUENCE: 128

Gly Ser Gly Ser
1

<210> SEQ ID NO 129
<211> LENGTH: 8
<212> TYPE: PRT
<213> ORGANISM: Artificial Sequence
<220> FEATURE:
<223> OTHER INFORMATION: Linker

<400> SEQUENCE: 129

Gly Gly Gly Ser Gly Gly Gly Ser
1               5

<210> SEQ ID NO 130
<211> LENGTH: 25
<212> TYPE: PRT
<213> ORGANISM: Artificial Sequence
<220> FEATURE:
<223> OTHER INFORMATION: linker

<400> SEQUENCE: 130

Gly Gly Gly Gly Ser Gly Gly Gly Ser Gly Gly Gly Ser Gly
1               5                   10                  15

Gly Gly Ser Gly Gly Gly Gly Ser
            20                  25

<210> SEQ ID NO 131
<211> LENGTH: 4
<212> TYPE: PRT
<213> ORGANISM: Artificial Sequence
<220> FEATURE:
<223> OTHER INFORMATION: Linker

<400> SEQUENCE: 131

Ala Pro Ala Pro
1
```

-continued

```
<210> SEQ ID NO 132
<211> LENGTH: 10
<212> TYPE: PRT
<213> ORGANISM: Artificial Sequence
<220> FEATURE:
<223> OTHER INFORMATION: Linker

<400> SEQUENCE: 132

Ala Pro Ala Pro Ala Pro Ala Pro Ala Pro
1               5                   10

<210> SEQ ID NO 133
<211> LENGTH: 20
<212> TYPE: PRT
<213> ORGANISM: Artificial Sequence
<220> FEATURE:
<223> OTHER INFORMATION: Linker

<400> SEQUENCE: 133

Ala Pro Ala Pro Ala Pro Ala Pro Ala Pro Ala Pro Ala Pro Ala Pro
1               5                   10                  15

Ala Pro Ala Pro
            20

<210> SEQ ID NO 134
<211> LENGTH: 40
<212> TYPE: PRT
<213> ORGANISM: Artificial Sequence
<220> FEATURE:
<223> OTHER INFORMATION: Linker

<400> SEQUENCE: 134

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 135
<211> LENGTH: 28
<212> TYPE: PRT
<213> ORGANISM: Artificial Sequence
<220> FEATURE:
<223> OTHER INFORMATION: Linker

<400> SEQUENCE: 135

Glu Ala Ala Ala Lys Glu Ala Ala Lys Glu Ala Ala Ala Lys Glu
1               5                   10                  15

Ala Ala Ala Lys Glu Ala Ala Ala Lys Ala Ala Ala
            20                  25

<210> SEQ ID NO 136
<211> LENGTH: 585
<212> TYPE: PRT
<213> ORGANISM: Artificial Sequence
<220> FEATURE:
<223> OTHER INFORMATION: Albumin variant

<400> SEQUENCE: 136

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30
```

```
Gln Ser Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445
```

-continued

```
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
            485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
            565                 570                 575
Ala Ala Ser Gln Ala Ala Leu Gly Leu
            580                 585
```

PD-L1 BINDING FIBRONECTIN TYPE III DOMAINS

CROSS-REFERENCE TO RELATED APPLICATIONS

This application claims the benefit of U.S. Provisional Application Ser. No. 62/434,054, filed 14 Dec. 2016, the entire contents of which are incorporated herein by reference.

SEQUENCE LISTING

This application contains a Sequence Listing submitted via EFS-Web, the entire content of which is incorporated herein by reference. The ASCII text file, created on 11 Dec. 2017, is named JBI5113USNP_ST25.txt and is 124 kilobytes in size.

FIELD OF THE INVENTION

The present invention relates to fibronectin type III domains that specifically bind to PD-L1 and methods of making and using the molecules.

BACKGROUND OF THE INVENTION

The immune system is tightly controlled by a network of costimulatory and co-inhibitory ligands and receptors. These molecules provide secondary signals for T cell activation and provide a balanced network of positive and negative signals to maximize immune responses against infection and tumors, while limiting immunity to self (Wang et al., (Epub Mar. 7, 2011) *J Exp Med* 208(3):577-92; Lepenies et al., (2008) *Endocr Metab Immune Disord Drug Targets* 8:279-288).

Programmed Death-1 (PD-1) is a key immune checkpoint receptor expressed by activated T and B cells and mediates immunosuppression. The ligand for PD-1, PD-L1, is expressed by antigen-presenting cells and many cancers such as lung, ovarian and colon carcinoma and various myelomas. Binding of PD-L1 to PD-1 on T cells downregulates T cell proliferation and activation and drives T cell anergy and exhaustion in the tumor microenvironment, facilitating tumor cell escape from T-cell mediated immune surveillance.

Therapeutic efficacy of PD-1 and PD-L1 antagonists has been validated in clinical trials. However, response rates remain low. For example, Opdivo® (Nivolumab) treatment achieved a 26% objective response rate (ORR) across the 27 clinical trials analyzed (Tie et al., *Int J Cancer* 2016 Nov. 4 doi: 10.1002/ijc.30501. [Epub ahead of print])

Measuring the expression of PD-L1 protein in the tumor tissue may aid in the early detection of cancer pathologies and may help assess the efficacy and durability of PD-L1 and PD-1 antagonists. For example, PD-L1 expression in at least 50% of tumor cells correlated with improved efficacy of Keytruda® (pembrolizumab) (Garon et al., N Engl J Med 2015; 372:2018-2028), and PD-L1 expression has been correlated with poor prognosis (see for example Wang et al., Eur J Surg oncol 2015 April; 41(4):450-6).

However, the use of PD-L1 protein expression as an accurate predictor for cancer and/or the efficacy of anti-PD-1 and anti-PD-L1 directed therapies remain challenging partially due to observed variability in results depending on the detection reagent used. For example, the evaluation of PD-L1 expression in non-small cell lung cancer samples using commercially available assays such as PD-L1 (E1L3N®) XP® Rabbit mAb (Cell Signaling) and Ventana PD-L1 (SP142) Assay yielded discordant results (McLaughlin et al., JAMA Oncol 2016 January; 2(1):46-54)

Therefore, there is a need for reagents to accurately detect PD-L1 in tumor tissues and other samples and new therapeutics that modulate the interaction between PD-L1 and PD-1.

SUMMARY OF THE INVENTION

The invention provides an isolated FN3 domain that specifically binds to PD-L1.

The invention also provides an isolated FN3 domain that specifically binds to PD-L1 comprising the sequence of SEQ ID NOs: 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123 or 124.

The invention also provides an isolated polynucleotide encoding the FN3 domain that specifically binds to PD-L1 of the invention.

The invention also provides a vector comprising the polynucleotide of the invention.

The invention also provides a host cell comprising the vector of the invention.

The invention also provides a method of producing the FN3 domain that specifically binds to PD-L1 of the invention, comprising culturing the isolated host cell of the invention under conditions that the FN3 domain that specifically binds to PD-L1 is expressed, and purifying the FN3 domain that specifically binds to PD-L1.

The invention also provides a pharmaceutical composition comprising the FN3 domain that specifically binds to PD-L1 of the invention and a pharmaceutically acceptable carrier.

The invention also provides an anti-idiotypic antibody that specifically binds the FN3 domain that specifically binds to PD-L1 of the invention.

The invention also provides a kit comprising the FN3 domain of the invention.

The invention also provides a method of detecting PD-L1-expressing cancer cells in a tumor tissue, comprising
  obtaining a sample of the tumor tissue from a subject; and
  detecting whether PD-L1 is expressed in the tumor tissue by contacting the sample of the tumor tissue with the FN3 domain that specifically binds to PD-L1 comprising the sequence of any one of SEQ ID NOs: 34-124 and detecting the binding between PD-L1 and the FN3 domain.

The invention also provides a method of isolating or detecting PD-L1 expressing cells, comprising obtaining a sample from a subject;
  contacting the sample with the FN3 domain that specifically binds to PD-L1 comprising the sequence of any one of SEQ ID NOs: 34-124, and
  isolating or detecting the cells bound to the FN3 domains.

The invention also provides a method of detecting PD-L1-expressing cancer cells in a tumor tissue, comprising
  conjugating the FN3 domain that specifically binds to PD-L1 comprising the sequence of any one of SEQ ID NOs: 34-124 to a detectable label to form a conjugate;
  administering the conjugate to a subject; and visualizing the PD-L1 expressing cancer cells to which the conjugate is bound.

DETAILED DESCRIPTION OF THE INVENTION

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10).

"Centyrin" refers to a FN3 domain that is based on the consensus sequence of the 15 different FN3 domains present in human tenascin C.

The term "capture agent" refers to substances that bind to a particular type of cells and enable the isolation of that cell from other cells. Exemplary capture agents are magnetic beads, ferrofluids, encapsulating reagents, molecules that bind the particular cell type and the like.

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Substituting" or "substituted" or 'mutating" or "mutated" refers to altering, deleting of inserting one or more amino acids or nucleotides in a polypeptide or polynucleotide sequence to generate a variant of that sequence.

"Variant" refers to a polypeptide or a polynucleotide that differs from a reference polypeptide or a reference polynucleotide by one or more modifications for example, substitutions, insertions or deletions.

"Specifically binds" or "specific binding" refers to the ability of the FN3 domain of the invention to bind PD-L1 with a dissociation constant ($K_D$) of about $1\times10^{-6}$ M or less, for example about $1\times10^{-7}$ M or less, about $1\times10^{-8}$ M or less, about $1\times10^{-13}$ M or less, about $1\times10^{-10}$ M or less, about $1\times10^{-11}$ M or less, about $1\times10^{-12}$ M or less, or about $1\times10^{-13}$ M or less. Alternatively, "specific binding" refers to the ability of the FN3 domain of the invention to bind PD-L1 at least 5-fold above the negative control in standard ELISA assay. The isolated FN3 domain of the invention that specifically binds PD-L1 may, however, have cross-reactivity to other related antigens, for example to the same predetermined antigen from other species (homologs), such as *Macaca Fascicularis* (cynomolgous monkey, cyno) or Pan troglodytes (chimpanzee).

"Library" refers to a collection of variants. The library may be composed of polypeptide or polynucleotide variants.

"Stability" refers to the ability of a molecule to maintain a folded state under physiological conditions such that it retains at least one of its normal functional activities, for example, binding to a predetermined antigen such as PD-L1.

"PD-L1" refers to human PD-L1 protein having the amino acid sequence of SEQ ID NO: 32. The extracellular domain of PD-L1 spans residues 1-220, the transmembrane domain spans residues 221-241 and the cytoplasmic domain spans residues 242-272.

"PD-1" refers to human PD-1 protein having the amino acid sequence of SEQ ID NO: 33. The extracellular domain of PD-1 spans residues 1-150, the transmembrane domain spans residues 151-171 and the cytoplasmic domain spans residues 172-268 of SEQ ID NO: 33.

"Tencon" refers to the synthetic fibronectin type III (FN3) domain having the sequence shown in SEQ ID NO: 1 and described in U.S. Pat. Publ. No. 2010/0216708.

A "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than about 50 amino acids may be referred to as "peptides".

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Subject" includes any human or nonhuman animal "Nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

Compositions of Matter

The present invention provides fibronectin type III (FN3) domains that specifically bind PD-L1. These molecules can be used in therapeutic and diagnostic applications and in imaging. The present invention provides polynucleotides encoding the FN3 domains of the invention or complementary nucleic acids thereof, vectors, host cells, and methods of making and using them.

The invention provides an isolated FN3 domain that specifically binds PD-L1. The FN3 domain of the invention may bind PD-L1 with a dissociation constant ($K_D$) of less than about $1 \times 10^{-7}$ M, for example less than about $1 \times 10^{-8}$ M, less than about $1 \times 10^{-9}$ M, less than about $1 \times 10^{-10}$ M, less than about $1 \times 10^{-11}$ M, less than about $1 \times 10^{-12}$ M, or less than about $1 \times 10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffer described herein.

The FN3 domain of the invention may bind PD-L1 at least 5-fold above the signal obtained for a negative control in standard ELISA assay.

In some embodiments, the FN3 domain that specifically binds PD-L1 comprises an initiator methionine (Met) linked to the N-terminus of the molecule.

In some embodiments, the FN3 domain that specifically binds PD-L1 comprises a cysteine (Cys) linked to a C-terminus of the FN3 domain.

The addition of the N-terminal Met and/or the C-terminal Cys may facilitate expression and/or conjugation of half-life extending molecules.

In some embodiments, the FN3 domain that specifically binds PD-L1 is internalized into a cell.

Internalization of the FN3 domain may facilitate delivery of a cytotoxic agent into tumor cells.

In some embodiments, the FN3 domain that specifically binds PD-L1 inhibits binding of PD-L1 to PD-1.

Inhibition of binding of PD-L1 to PD-1 by the FN3 domains of the invention may be assessed using competition ELISA. In an exemplary assay, 1 µg/ml recombinant human PD-L1 extracellular domain is bound on wells of microtiter plates, the wells are washed and blocked, and 10 µg/ml of the test FN3 domain is added. Without washing, 7.5 µg/ml PD-1 extracellular domain is added into the wells and incubated for 30 min, after which 0.5 µg/ml anti-PD-1 antibody is added and incubated for 30 min. The plates are washed and 0.5 µg/mL neutravidin-HRP conjugate polyclonal antibody is added and incubated for 30 minutes. The plates are washed and POD Chemiluminescence substrate added immediately prior to reading the luminescence signal. The FN3 domains of the invention inhibit binding of PD-L1 to PD-1 when the binding of PD-1 is reduced by at least about 80%, 85%, 90%, 95% or 100%.

In some embodiments, the FN3 domain that specifically binds PD-L1 is a PD-L1 antagonist.

In some embodiments, the FN3 domain that specifically binds PD-L1 is a PD-L1 agonist.

"Antagonist" refers to a FN3 domain that specifically binds PD-L1 that suppresses at least one reaction or activity that is induced by PD-L1 binding PD-1. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. A typical reaction or activity that is induced by PD-L1 binding PD-1 is reduced antigen-specific CD4$^+$ or CD8$^+$ cell proliferation or reduced interferon-γ (IFN-γ) production by T cells.

The antagonistic FN3 domains that specifically bind PD-L1 may be used in the treatment of cancer or viral infections and in general in treatment of diseases in which activation of immune responses is desirable.

"Agonist" refers to a FN3 domain that specifically binds PD-L1 that induces at least one reaction or activity that is induced by PD-L1 binding PD-1. The FN3 domain is an agonist when the at least one reaction or activity is induced by at least about 30%, 40%, 45%, 50%, 55%, 60%, 65%, 70%, 75%, 80%, 85%, 90%, 95%, or 100% greater than the at least one reaction or activity induced in the absence of the agonist (e.g., negative control), or when the induction is statistically significant when compared to the induction in the absence of the agonist. A typical reaction or activity that is induced by PD-L1 binding PD-1 is reduced antigen-specific CD4$^+$ or CD8$^+$ cell proliferation or reduced interferon-γ (IFN-γ) production by T cells.

The agonistic FN3 domains that specifically bind PD-L1 may be used in the treatment of autoimmune or inflammatory diseases and in general diseases in which suppression of immune responses is desirable.

In some embodiments, the FN3 domain that specifically binds PD-L1 does not inhibit binding of PD-L1 to PD-1.

In some embodiments, the FN3 domain that specifically binds PD-L1 does not activate signaling downstream of PD-1.

In some embodiments, the FN3 domain that specifically binds PD-L1 is based on Tencon sequence of SEQ ID NO: 1 or Tencon 27 sequence of SEQ ID NO: 4, optionally having substitutions at residues positions 11, 14, 17, 37, 46, 73, and/or 86 (residue numbering corresponding to SEQ ID NO: 4).

The invention also provides an isolated FN3 domain that specifically binds PD-L1 comprising the amino acid sequence of SEQ ID NOs: 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123 and/or 124.

The invention also provides an isolated FN3 domain that specifically binds PD-L1 comprising the amino acid sequence of SEQ ID NO: 34.

The invention also provides an isolated FN3 domain that specifically binds PD-L1 comprising the amino acid sequence of SEQ ID NO: 35.

The invention also provides an isolated FN3 domain that specifically binds PD-L1 comprising the amino acid sequence of SEQ ID NO: 36.

The invention also provides an isolated FN3 domain that specifically binds PD-L1 comprising the amino acid sequence of SEQ ID NO: 37.

The invention also provides an isolated FN3 domain that specifically binds PD-L1 comprising the amino acid sequence of SEQ ID NO: 38.

The invention also provides an isolated FN3 domain that specifically binds PD-L1 comprising the amino acid sequence of SEQ ID NO: 39.

The invention also provides an isolated FN3 domain that specifically binds PD-L1 comprising the amino acid sequence of SEQ ID NO: 40.

The invention also provides an isolated FN3 domain that specifically binds PD-L1 comprising the amino acid sequence of SEQ ID NO: 41.

The invention also provides an isolated FN3 domain that specifically binds PD-L1 comprising the amino acid sequence of SEQ ID NO: 42.

The invention also provides an isolated FN3 domain that specifically binds PD-L1 comprising the amino acid sequence of SEQ ID NO: 43.

The invention also provides an isolated FN3 domain that specifically binds PD-L1 comprising the amino acid sequence of SEQ ID NO: 44.

The invention also provides an isolated FN3 domain that specifically binds PD-L1 comprising the amino acid sequence of SEQ ID NO: 45.

The invention also provides an isolated FN3 domain that specifically binds PD-L1 comprising the amino acid sequence of SEQ ID NO: 46.

The invention also provides an isolated FN3 domain that specifically binds PD-L1 comprising the amino acid sequence of SEQ ID NO: 47.

The invention also provides an isolated FN3 domain that specifically binds PD-L1 comprising the amino acid sequence of SEQ ID NO: 48.

The invention also provides an isolated FN3 domain that specifically binds PD-L1 comprising the amino acid sequence of SEQ ID NO: 49.

The invention also provides an isolated FN3 domain that specifically binds PD-L1 comprising the amino acid sequence of SEQ ID NO: 50.

The invention also provides an isolated FN3 domain that specifically binds PD-L1 comprising the amino acid sequence of SEQ ID NO: 51.

The invention also provides an isolated FN3 domain that specifically binds PD-L1 comprising the amino acid sequence of SEQ ID NO: 52.

The invention also provides an isolated FN3 domain that specifically binds PD-L1 comprising the amino acid sequence of SEQ ID NO: 53.

The invention also provides an isolated FN3 domain that specifically binds PD-L1 comprising the amino acid sequence of SEQ ID NO: 54.

The invention also provides an isolated FN3 domain that specifically binds PD-L1 comprising the amino acid sequence of SEQ ID NO: 55.

The invention also provides an isolated FN3 domain that specifically binds PD-L1 comprising the amino acid sequence of SEQ ID NO: 56.

The invention also provides an isolated FN3 domain that specifically binds PD-L1 comprising the amino acid sequence of SEQ ID NO: 57.

The invention also provides an isolated FN3 domain that specifically binds PD-L1 comprising the amino acid sequence of SEQ ID NO: 58.

The invention also provides an isolated FN3 domain that specifically binds PD-L1 comprising the amino acid sequence of SEQ ID NO: 59.

The invention also provides an isolated FN3 domain that specifically binds PD-L1 comprising the amino acid sequence of SEQ ID NO: 60.

The invention also provides an isolated FN3 domain that specifically binds PD-L1 comprising the amino acid sequence of SEQ ID NO: 61.

The invention also provides an isolated FN3 domain that specifically binds PD-L1 comprising the amino acid sequence of SEQ ID NO: 62.

The invention also provides an isolated FN3 domain that specifically binds PD-L1 comprising the amino acid sequence of SEQ ID NO: 63.

The invention also provides an isolated FN3 domain that specifically binds PD-L1 comprising the amino acid sequence of SEQ ID NO: 64.

The invention also provides an isolated FN3 domain that specifically binds PD-L1 comprising the amino acid sequence of SEQ ID NO: 65.

The invention also provides an isolated FN3 domain that specifically binds PD-L1 comprising the amino acid sequence of SEQ ID NO: 66.

The invention also provides an isolated FN3 domain that specifically binds PD-L1 comprising the amino acid sequence of SEQ ID NO: 67.

The invention also provides an isolated FN3 domain that specifically binds PD-L1 comprising the amino acid sequence of SEQ ID NO: 68.

The invention also provides an isolated FN3 domain that specifically binds PD-L1 comprising the amino acid sequence of SEQ ID NO: 69.

The invention also provides an isolated FN3 domain that specifically binds PD-L1 comprising the amino acid sequence of SEQ ID NO: 70.

The invention also provides an isolated FN3 domain that specifically binds PD-L1 comprising the amino acid sequence of SEQ ID NO: 71.

The invention also provides an isolated FN3 domain that specifically binds PD-L1 comprising the amino acid sequence of SEQ ID NO: 72.

The invention also provides an isolated FN3 domain that specifically binds PD-L1 comprising the amino acid sequence of SEQ ID NO: 73.

The invention also provides an isolated FN3 domain that specifically binds PD-L1 comprising the amino acid sequence of SEQ ID NO: 74.

The invention also provides an isolated FN3 domain that specifically binds PD-L1 comprising the amino acid sequence of SEQ ID NO: 75.

The invention also provides an isolated FN3 domain that specifically binds PD-L1 comprising the amino acid sequence of SEQ ID NO: 76.

The invention also provides an isolated FN3 domain that specifically binds PD-L1 comprising the amino acid sequence of SEQ ID NO: 77.

The invention also provides an isolated FN3 domain that specifically binds PD-L1 comprising the amino acid sequence of SEQ ID NO: 78.

The invention also provides an isolated FN3 domain that specifically binds PD-L1 comprising the amino acid sequence of SEQ ID NO: 79.

The invention also provides an isolated FN3 domain that specifically binds PD-L1 comprising the amino acid sequence of SEQ ID NO: 80.

The invention also provides an isolated FN3 domain that specifically binds PD-L1 comprising the amino acid sequence of SEQ ID NO: 81.

The invention also provides an isolated FN3 domain that specifically binds PD-L1 comprising the amino acid sequence of SEQ ID NO: 82.

The invention also provides an isolated FN3 domain that specifically binds PD-L1 comprising the amino acid sequence of SEQ ID NO: 83.

The invention also provides an isolated FN3 domain that specifically binds PD-L1 comprising the amino acid sequence of SEQ ID NO: 84.

The invention also provides an isolated FN3 domain that specifically binds PD-L1 comprising the amino acid sequence of SEQ ID NO: 85.

The invention also provides an isolated FN3 domain that specifically binds PD-L1 comprising the amino acid sequence of SEQ ID NO: 86.

The invention also provides an isolated FN3 domain that specifically binds PD-L1 comprising the amino acid sequence of SEQ ID NO: 87.

The invention also provides an isolated FN3 domain that specifically binds PD-L1 comprising the amino acid sequence of SEQ ID NO: 88.

The invention also provides an isolated FN3 domain that specifically binds PD-L1 comprising the amino acid sequence of SEQ ID NO: 89.

The invention also provides an isolated FN3 domain that specifically binds PD-L1 comprising the amino acid sequence of SEQ ID NO: 90.

The invention also provides an isolated FN3 domain that specifically binds PD-L1 comprising the amino acid sequence of SEQ ID NO: 91.

The invention also provides an isolated FN3 domain that specifically binds PD-L1 comprising the amino acid sequence of SEQ ID NO: 92.

The invention also provides an isolated FN3 domain that specifically binds PD-L1 comprising the amino acid sequence of SEQ ID NO: 93.

The invention also provides an isolated FN3 domain that specifically binds PD-L1 comprising the amino acid sequence of SEQ ID NO: 94.

The invention also provides an isolated FN3 domain that specifically binds PD-L1 comprising the amino acid sequence of SEQ ID NO: 95.

The invention also provides an isolated FN3 domain that specifically binds PD-L1 comprising the amino acid sequence of SEQ ID NO: 96.

The invention also provides an isolated FN3 domain that specifically binds PD-L1 comprising the amino acid sequence of SEQ ID NO: 97.

The invention also provides an isolated FN3 domain that specifically binds PD-L1 comprising the amino acid sequence of SEQ ID NO: 98.

The invention also provides an isolated FN3 domain that specifically binds PD-L1 comprising the amino acid sequence of SEQ ID NO: 99.

The invention also provides an isolated FN3 domain that specifically binds PD-L1 comprising the amino acid sequence of SEQ ID NO: 100.

The invention also provides an isolated FN3 domain that specifically binds PD-L1 comprising the amino acid sequence of SEQ ID NO: 101.

The invention also provides an isolated FN3 domain that specifically binds PD-L1 comprising the amino acid sequence of SEQ ID NO: 102.

The invention also provides an isolated FN3 domain that specifically binds PD-L1 comprising the amino acid sequence of SEQ ID NO: 103.

The invention also provides an isolated FN3 domain that specifically binds PD-L1 comprising the amino acid sequence of SEQ ID NO: 104.

The invention also provides an isolated FN3 domain that specifically binds PD-L1 comprising the amino acid sequence of SEQ ID NO: 105.

The invention also provides an isolated FN3 domain that specifically binds PD-L1 comprising the amino acid sequence of SEQ ID NO: 106.

The invention also provides an isolated FN3 domain that specifically binds PD-L1 comprising the amino acid sequence of SEQ ID NO: 107.

The invention also provides an isolated FN3 domain that specifically binds PD-L1 comprising the amino acid sequence of SEQ ID NO: 108.

The invention also provides an isolated FN3 domain that specifically binds PD-L1 comprising the amino acid sequence of SEQ ID NO: 109.

The invention also provides an isolated FN3 domain that specifically binds PD-L1 comprising the amino acid sequence of SEQ ID NO: 110.

The invention also provides an isolated FN3 domain that specifically binds PD-L1 comprising the amino acid sequence of SEQ ID NO: 111.

The invention also provides an isolated FN3 domain that specifically binds PD-L1 comprising the amino acid sequence of SEQ ID NO: 112.

The invention also provides an isolated FN3 domain that specifically binds PD-L1 comprising the amino acid sequence of SEQ ID NO: 113.

The invention also provides an isolated FN3 domain that specifically binds PD-L1 comprising the amino acid sequence of SEQ ID NO: 114.

The invention also provides an isolated FN3 domain that specifically binds PD-L1 comprising the amino acid sequence of SEQ ID NO: 115.

The invention also provides an isolated FN3 domain that specifically binds PD-L1 comprising the amino acid sequence of SEQ ID NO: 116.

The invention also provides an isolated FN3 domain that specifically binds PD-L1 comprising the amino acid sequence of SEQ ID NO: 117.

The invention also provides an isolated FN3 domain that specifically binds PD-L1 comprising the amino acid sequence of SEQ ID NO: 118.

The invention also provides an isolated FN3 domain that specifically binds PD-L1 comprising the amino acid sequence of SEQ ID NO: 119.

The invention also provides an isolated FN3 domain that specifically binds PD-L1 comprising the amino acid sequence of SEQ ID NO: 120.

The invention also provides an isolated FN3 domain that specifically binds PD-L1 comprising the amino acid sequence of SEQ ID NO: 121.

The invention also provides an isolated FN3 domain that specifically binds PD-L1 comprising the amino acid sequence of SEQ ID NO: 122.

The invention also provides an isolated FN3 domain that specifically binds PD-L1 comprising the amino acid sequence of SEQ ID NO: 123.

The invention also provides an isolated FN3 domain that specifically binds PD-L1 comprising the amino acid sequence of SEQ ID NO: 124.

In some embodiments, the isolated FN3 domain that specifically binds PD-L1 comprises an initiator methionine (Met) linked to the N-terminus of the molecule.

in some embodiments, the isolated FN3 domain that specifically binds PD-L1 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 74.

In some embodiments, the isolated FN3 domain that specifically binds PD-L1 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of any one of SEQ ID NOs: 34-124.

Conjugates of the FN3 Domains that Specifically Bind PD-L1 of the Invention

The invention also provides an isolated FN3 domain that specifically binds PD-L1 conjugated to a heterologous molecule(s).

In some embodiments, the heterologous molecule is a detectable label or a cytotoxic agent.

The invention also provides an FN3 domain that specifically binds PD-L1 conjugated to a detectable label.

The invention also provides an FN3 domain that specifically binds PD-L1 conjugated to a cytotoxic agent.

In some embodiments, the detectable label is also a cytotoxic agent.

The FN3 domains that specifically bind PD-L1 of the invention conjugated to a detectable label can be used to evaluate expression of PD-L1 on samples such as tumor tissue in vivo or in vitro.

Detectable label includes compositions that when conjugated to the FN3 domains that specifically bind PD-L1 of the invention renders the latter detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemilumine scent molecules, fluorochromes, fluorophores, fluorescent quenching agents, colored molecules, radioactive isotopes, cintillants, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases the detectable label emits a signal as a result of being stimulated by an external field.

Exemplary radioactive isotopes may be γ-emitting, Auger-emitting, β-emitting, an alpha-emitting or positron-emitting radioactive isotope. Exemplary radioactive isotopes include $^{3}H$, $^{11}C$, $^{13}C$, $^{15}N$, $^{18}F$, $^{19}F$, $^{55}Co$, $^{57}Co$, $^{60}Co$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{90}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, *neptunium* atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e. iodine) to 83 (i.e. bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^{+}$, $Ca^{2+}$, $Cr^{2+}$, $Cr^{3+}$, $Cr^{4+}$, $Co^{2+}$, $Co^{3+}$, $Cu^{+}$, $Cu^{2+}$, $Cu^{3+}$, $Ga^{3+}$, $Gd^{3+}$, $Au^{+}$, $Au^{+}$, $Pe^{+}$, $Fe^{+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^{+}$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The FN3 domains that specifically bind PD-L1 conjugated to a detectable label may be used as an imaging agent to evaluate tumor distribution, diagnosis for the presence of tumor cells and/or, recurrence of tumor.

In some embodiments, the FN3 domains that specifically bind PD-L1 of the invention are conjugated to a cytotoxic agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The FN3 domains that specifically bind PD-L1 conjugated to a cytotoxic agent of the invention may be used in the targeted delivery of the cytotoxic agent to PD-L1 expressing tumor cell, and intracellular accumulation therein, wherein systemic administration of these unconjugated cytotoxic agents may result in unacceptable levels of toxicity to normal cells.

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxins such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}$Bi, $^{131}$I, $^{131}$In, $^{90}$Y, and $^{186}$Re.

In some embodiments, the cytotoxic agent is dolastatins or dolostatin peptidic analogs and derivatives, auristatin or monomethyl auristatin phenylalanine Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancerand antifungal activity. The dolastatin or auristatin drug moiety may be attached to the FN3 domain of the invention through the N (amino) terminus or the C (carboxyl) terminus of the peptidic drug moiety (WO 02/088172), or via any cysteine engineered into the FN3 domain.

The FN3 domains that specifically bind PD-L1 of the invention may be conjugated to a detectable label using known methods.

In some embodiments, the detectable label is complexed with a chelating agent.

In some embodiments, the detectable label is conjugated to the FN3 domain that specifically binds PD-L1 of the invention via a linker.

The detectable label or the cytotoxic moiety may be linked directly, or indirectly, to the FN3 domain that specifically binds PD-L1 of the invention using known methods. Suitable linkers are known in the art and include, for example, prosthetic groups, non-phenolic linkers (derivatives of N-succinimidyl-benzoates; dodecaborate), chelating moieties of both macrocyclics and acyclic chelators, such as derivatives of 1,4,7,10-tetraazacyclododecane-1,4,7,10, tetraacetic acid (DOTA), derivatives of diethylenetriaminepentaacetic avid (DTPA), derivatives of S-2-(4-Isothiocyanato-benzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

In some embodiment, the FN3 domain that specifically binds PD-L1 is removed from the blood via renal clearance.

Isolation of PD-L1 Binding FN3 Domains from a Library Based on Tencon Sequence

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind Pd-L1. Table 1 shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in U.S. Pat. Publ. No. US2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 4) having substitutions E11R, L17A, N46V and E86I when compared to Tencon of SEQ ID NO: 1.

TABLE 1

| FN3 domain | Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_//www_s-loning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well-known IUB code.

The FN3 domains that specifically bind PD-L1 of the invention may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to PSMA by any method known in the art and described in the Example.

Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains that specifically bind PD-L1 are further characterized for their binding to PD-L1, modulation of PD-L1 activity, internalization, stability, and other desired characteristics.

The FN3 domains that specifically bind PD-L1 of the invention may be generated using any FN3 domain as a template to generate a library and screening the library for molecules specifically binding PD-L1 using methods provided within. Exemplar FN3 domains that may be used are the 3rd FN3 domain of tenascin C (TN3) (SEQ ID NO: 125), Fibcon (SEQ ID NO: 126), and the $10^{th}$ FN3 domain of fibronectin (FN10) (SEQ ID NO: 127). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U. S. Pat. Publ. No. 2011/0118144; Int. Pat. Publ. No. WO2009/085462; U.S. Pat. Nos. 6,969,108; 6,172,197; 5,223,409; 6,582,915; 6,472,147).

In some embodiments, the FN3 domain that specifically binds PD-L1 is based on Tencon sequence of SEQ ID NO: 1 or Tencon27 sequence of SEQ ID NO: 4, the SEQ ID NO: 1 or the SEQ ID NO: 4, optionally having substitutions at residues positions 11, 14, 17, 37, 46, 73, and/or 86.

The FN3 domains that specifically bind PD-L1 of the invention may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues may be incorporated to the FN3 domain containing molecules of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In one embodiment, the FN3 domain that specifically binds PD-L1 of the invention may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the $T_m$.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain that specifically binds PD-L1 of the invention may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing polyglycine, glycine and serine, or alanine and proline. Exemplary linker include $(GS)_2$, (SEQ ID NO: 128), $(GGGS)_2$ (SEQ ID NO: 129), $(GGGGS)_5$ (SEQ ID NO: 130), $(AP)_2$ (SEQ ID NO: 131), $(AP)_5$ (SEQ ID NO: 132), $(AP)_{10}$ (SEQ ID NO: 133), $(AP)_{20}$ (SEQ ID NO: 134) and $A(EAAAK)_5$ AAA (SEQ ID NO: 135). The dimers and multimers may be linked to each other in a N-to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Half-Life Extending Moieties

The FN3 domains that specifically bind PD-L1 of the invention may incorporate other subunits for example via covalent interaction. In one aspect of the invention, the FN3 domains that specifically bind PD-L1 of the invention further comprise a half-life extending moiety. Exemplary half-life extending moieties are albumin, albumin variants, albumin-binding proteins and/or domains, transferrin and fragments and analogues thereof, and Fc regions. An exemplary albumin variant is shown in SEQ ID NO: 136. Amino acid sequences of the human Fc regions are well known, and include IgG1, IgG2, IgG3, IgG4, IgM, IgA and IgE Fc regions.

All or a portion of an antibody constant region may be attached to the FN3 domain that specifically binds PD-L1 of the invention to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see Strohl, *Curr Opin Biotechnol.* 20, 685-691, 2009).

Additional moieties may be incorporated into the FN3 domains that specifically bind PD-L1 of the invention such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the FN3 domain that specifically binds PD-L1 of the invention by incorporating a cysteine residue to the C-terminus of the molecule, or engineering cysteines into residue positions that face away from the PD-L1 binding face of the molecule, and attaching a pegyl group to the cysteine using well known methods.

FN3 domains that specifically bind PD-L1 of the invention incorporating additional moieties may be compared for functionality by several well-known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention also provides nucleic acids encoding the FN3 domains specifically binding PD-L1 of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the FN3 domains of the invention are also within the scope of the invention.

The invention also provides an isolated polynucleotide encoding the FN3 domain specifically binding PD-L1 comprising the amino acid sequence of SEQ ID NOs: 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123 or 124.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such as PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

The invention also provides a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

The invention also provides a host cell comprising the vector of the invention. The FN3 domain that specifically bind PD-L1 of the invention may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, 3$^{rd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The invention also provides a method of producing the isolated FN3 domain that specifically binds PD-L1 of the invention, comprising culturing the isolated host cell of the invention under conditions such that the isolated FN3 domain that specifically binds PD-L1 is expressed, and purifying the FN3 domain.

The FN3 domains that specifically bind PD-L1 may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Anti-Idiotypic Antibodies

The present invention also provides an anti-idiotypic antibody binding to the FN3 domain of the invention.

The invention also provides an anti-idiotypic antibody that specifically binds the FN3 domain comprising any one of SEQ ID NOs: 34-124.

Kits

The invention also provides a kit comprising the FN3 domain that specifically binds PD-L1 of the invention.

The kit may be used for therapeutic uses and as a diagnostic kit.

In some embodiments, the kit comprises the FN3 domain that specifically binds PD-L1 of the invention and reagents for detecting the FN3 domain. The kit can include one or more other elements including: instructions for use; other reagents, e.g., a label, an agent useful for chelating, or otherwise coupling, a radioprotective composition; devices or other materials for preparing the FN3 domain that specifically binds PD-L1 of the invention for administration for imaging, diagnostic or therapeutic purpose; pharmaceutically acceptable carriers; and devices or other materials for administration to a subject.

In some embodiments, the kit comprises the FN3 domain that specifically binds PD-L1 comprising any one of SEQ ID NOs: 34-124.

Uses of PD-L1 Binding FN3 Domains of the Invention

The FN3 domains that specifically bind PD-L1 of the invention may be used to diagnose, monitor, modulate, treat, alleviate, help prevent the incidence of, or reduce the symptoms of human disease or specific pathologies in cells, tissues, organs, fluid, or, generally, a host. The FN3 domains that specifically bind PD-L1 of the invention may also be used in imaging PD-L1 positive tumor tissue in a subject. The methods of the invention may be used with an animal patient belonging to any classification. Examples of such animals include mammals such as humans, rodents, dogs, cats and farm animals.

The invention provides a method of diagnosing a subject having, or who is likely to develop cancer of a tissue based on the expression of PD-L1 by cells of the cancer tissue, methods of predicting success of immunotherapy, methods of prognosis, and methods of treatment.

The invention also provides a method of detecting PD-L1-expressing cancer cells in a tumor tissue, comprising
obtaining a sample of the tumor tissue from a subject;
detecting whether PD-L1 is expressed in the tumor tissue by contacting toe sample of the tumor tissues with the FN3 domain that specifically binds PD-L1 comprising the sequence of any one of SEQ ID NOs: 34-124 and detecting the binding between PD-L1 and the FN3 domain.

The tissue can be tissue of any organ or anatomical system, for example lung, epithelial, connective, vascular, muscle, neural, skeletal, lymphatic, prostate, cervical, breast, spleen, gastric, intestinal, oral, esophageal, uterine, ovarian, renal or testicular tissue.

PD-L1 expression may be evaluated using known methods such as immunohistochemistry or ELISA.

The invention also provides a method of isolating PD-L1 expressing cells, comprising
obtaining a sample from a subject;
contacting the sample with the FN3 domain that specifically binds PD-L1 comprising the sequence of any one of SEQ ID NOs: 34-124, and
isolating the cells bound to the FN3 domains.

The invention also provides a method of detecting PD-L1-expressing cancer cells in a tumor tissue, comprising
conjugating the FN3 domain that specifically binds PD-L1 comprising the sequence of any one of SEQ ID NOs: 34-124 to a detectable label to form a conjugate;
administering the conjugate to a subject; and
visualizing the PD-L1 expressing cancer cells to which the conjugate is bound.

The invention also provides a method of treating a subject having cancer, comprising administering to the subject a FN3 domain that specifically binds PD-L1 of the invention.

In some embodiments, the subject has a solid tumor.

In some embodiments, the subject has a hematological malignancy.

In some embodiments, the solid tumor is a melanoma.

In some embodiments, the solid tumor is a lung cancer.

In some embodiments, the solid tumor is a non-small cell lung cancer (NSCLC).

In some embodiments, the solid tumor is a squamous non-small cell lung cancer (NSCLC).

In some embodiments, the solid tumor is a non-squamous NSCLC.

In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer.

In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the hematological malignancy is a lymphoma, a myeloma or a leukemia.

In some embodiments, the hematological malignancy is a B cell lymphoma.

In some embodiments, the hematological malignancy is Burkitt's lymphoma.

In some embodiments, the hematological malignancy is Hodgkin's lymphoma.

In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML).

In some embodiments, the hematological malignancy is a chronic myeloid leukemia (CML).

In some embodiments, the hematological malignancy is a chronic myelomoncytic leukemia (CMML).

In some embodiments, the hematological malignancy is a multiple myeloma (MM).

In some embodiments, the hematological malignancy is a plasmacytoma. In some embodiments, the cancer is kidney cancer.

"Treat" or "treatment" refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the FN3 domains that specifically bind PD-L1 of the invention may vary according to factors such as the disease state, age, sex, and weight of the individual. Exemplary indicators of an effective FN3 domain that specifically binds PD-L1 is improved well-being of the patient, decrease or shrinkage of the size of a tumor, arrested or slowed growth of a tumor, and/or absence of metastasis of cancer cells to other locations in the body.

Administration/Pharmaceutical Compositions

The invention provides for pharmaceutical compositions of the FN3 domains that specifically bind PD-L1, optionally conjugated to a detectable label or a cytotoxic drug of the invention and a pharmaceutically acceptable carrier. For therapeutic use, the FN3 domains that specifically bind PD-L1 of the invention may be prepared as pharmaceutical compositions containing an effective amount of the domain or molecule as an active ingredient in a pharmaceutically acceptable carrier. "Carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules of the invention in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the FN3 domains of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

While having described the invention in general terms, the embodiments of the invention will be further disclosed in the following examples that should not be construed as limiting the scope of the claims.

Example 1. Construction of Tencon Libraries with Randomized Loops

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, *Design, and Selection,* 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:
(SEQ ID NO 1):
LPAPKNLVVSEVTEDSLRLSWTAPDAAFDSFLIQYQESEKVGEAINLTVP

GSERSYDLTGLKPGTEYTVSIYGVKGGHRSNPLSAEFTT

Various libraries were generated using the tencon scaffold and various design strategies. In general, libraries TCL1 and TCL2 produced good binders. Generation of TCL1 and TCL2 libraries are described in detail in Int. Pat. Publ. No. WO/2014081944A2.

Construction of TCL1 Library

A library designed to randomize only the FG loop of Tencon (SEQ ID NO: 1), TCL1, was constructed for use with the cis-display system (Jacobs et al., Protein Engineering, *Design, and Selection,* 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon, KGGHRSN (SEQ ID NO: 55). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

TCL1 Library (SEQ ID NO: 2)
LPAPKNLVVSEVTEDSLRLSWTAPDAAFDSFLIQY-QESEKVGEAINLTVPGSERSY
DLTGLKPGTEYTVSIYGVX$_1$X$_2$X$_3$X$_4$X$_5$X$_6$X$_7$X$_8$X$_9$-X$_{10}$X$_{11}$X$_{12}$ PLSAEFTT; wherein X$_1$, X$_2$, X$_3$, X$_4$, X$_5$, X$_6$, X$_7$ is any amino acid; and
X$_8$, X$_9$, X$_{10}$, X$_{11}$ and X$_{12}$ are any amino acid or deleted Construction of TCL2 Library TCL2 library was constructed in which both the BC and the FG loops of Tencon were randomized and the distribution of amino acids at each position was strictly controlled. Table 3 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 2 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TCL2 library
(SEQ ID NO: 3)
LPAPKNLVVSEVTEDSLRLSWX$_1$X$_2$X$_3$X$_4$X$_5$X$_6$X$_7$X$_8$SFLIQYQESEKVG

EAINLTVPGSERSYDLTGLKPGTEYTVSIYGVX$_9$X$_{10}$X$_{11}$X$_{12}$X$_{13}$SX$_{14}$

X$_{15}$LSAEFTT; wherein

X$_1$ is Ala, Arg, Asn, Asp, Glu, Gln, Gly, His, Ile,

Leu, Lys, Phe, Pro, Ser, Thr, Trp, Tyr or Val;

X$_2$ is Ala, Arg, Asn, Asp, Glu, Gln, Gly, His, Ile,

Leu, Lys, Phe, Pro, Ser, Thr, Trp, Tyr or Val;

X$_3$ Ala, Arg, Asn, Asp, Glu, Gln, Gly, His, Ile,

Leu, Lys, Phe, Pro, Ser, Thr, Trp, Tyr or Val;

X$_4$ is Ala, Arg, Asn, Asp, Glu, Gln, Gly, His, Ile,

Leu, Lys, Phe, Pro, Ser, Thr, Trp, Tyr or Val;

X$_5$ is Ala, Arg, Asn, Asp, Glu, Gln, Gly, His, Ile,

Leu, Lys, Phe, Pro, Ser, Thr, Trp, Tyr or Val;

X$_6$ is Ala, Arg, Asn, Asp, Glu, Gln, Gly, His, Ile,

Leu, Lys, Phe, Pro, Ser, Thr, Trp, Tyr or Val;

X$_7$ is Phe, Ile, Leu, Val or Tyr;

X$_8$ is Asp, Glu or Thr;

X$_9$ is Ala, Arg, Asn, Asp, Glu, Gln, Gly, His, Ile,

Leu, Lys, Phe, Pro, Ser, Thr, Trp, Tyr or Val;

X$_{10}$ is Ala, Arg, Asn, Asp, Glu, Gln, Gly, His,

Ile, Leu, Lys, Phe, Pro, Ser, Thr, Trp, Tyr or

Val;

X$_{11}$ is Ala, Arg, Asn, Asp, Glu, Gln, Gly, His,

Ile, Leu, Lys, Phe, Pro, Ser, Thr, Trp, Tyr or

Val;

X$_{12}$ is Ala, Arg, Asn, Asp, Glu, Gln, Gly, His,

Ile, Leu, Lys, Phe, Pro, Ser, Thr, Trp, Tyr or

Val;

X$_{13}$ is Ala, Arg, Asn, Asp, Glu, Gln, Gly, His,

Ile, Leu, Lys, Phe, Pro, Ser, Thr, Trp, Tyr or

Val;

X$_{14}$ is Ala, Arg, Asn, Asp, Glu, Gln, Gly, His,

Ile, Leu, Lys, Phe, Pro, Ser, Thr, Trp, Tyr or

Val;
and

X$_{15}$ is Ala, Arg, Asn, Asp, Glu, Gln, Gly, His,

Ile, Leu, Lys, Phe, Pro, Ser, Thr, Trp, Tyr or

Val.

TABLE 2

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO: 4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

Stabilized Tencon (Tencon27)
(SEQ ID NO: 4)
LPAPKNLVVSRVTEDSARLSWTAPDAAFDSFLIQYQESEKVGEAIVLTVP

GSERSYDLTGLKPGTEYTVSIYGVKGGHRSNPLSAIFTT

TCL7 (randomized FG and BC loops)
(SEQ ID NO: 5)
LPAPKNLVVSRVTEDSARLSWX$_1$X$_2$X$_3$X$_4$X$_5$X$_6$X$_7$X8X$_9$FDSFLIQYQES

EKVGEAIVLTVPGSERSYDLTGLKPGTEYTVSIYGVX$_{10}$X$_{11}$X$_{12}$X$_{13}$

X$_{14}$X$_{15}$X$_{16}$X$_{17}$X$_{18}$X$_{19}$SNPLSAIFTT;
wherein

X$_1$, X$_2$, X$_3$, X$_4$, X$_5$, X$_6$, X$_{10}$, X$_{11}$, X$_{12}$, X$_{13}$, X$_{14}$,

X$_{15}$ and X$_{16}$ is A, D, E, F, G, H, I, K, L, N, P,

Q, R, S, T, V, W or Y; and

X$_7$, X$_8$, X$_9$, X$_{17}$, X$_{18}$ and X$_{19}$, is A, D, E, F, G, H,

I, K, L, N, P, Q, R, S, T, V, W, Y or deleted.

TCL9 (randomized FG loop)
(SEQ ID NO: 6)
LPAPKNLVVSRVTEDSARLSWTAPDAAFDSFLIQYQESEKVGEAIVLTVP

GSERSYDLTGLKPGTEYTVSIYGV X$_1$X$_2$X$_3$X$_4$X$_5$X$_6$X$_7$X$_8$X$_9$

X$_{10}$X$_{11}$X$_{12}$SNPLSAIFTT;

X$_1$, X$_2$, X$_3$, X$_4$, X$_5$, X$_6$ and X$_7$, is A, D, E, F, G,

H, I, K, L, N, P, Q, R, S, T, V, W or Y; and

X$_8$, X$_9$, X$_{10}$, X$_{11}$ and X$_{12}$ is A, D, E, F, G, H, I,

K, L, N, P, Q, R, S, T, V, W, Y or deleted.

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 µg) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by Qiagen spin column. The yield for each sub-library of TCL9 ranged from 32-34 µg.

Construction of FG/BC Loop Libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID NOs: 13-16, respectively) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide encoding for amino acid A17 (130mer-L17A, SEQ ID NO: 17) was produced by PCR using oligos POP2222ext (SEQ ID NO: 18) and LS1114 (SEQ ID NO: 19). This was done to include the L17A mutation in the library (CEN5243). Next, DNA fragments encoding for Tencon residues R18-V75 including randomized BC loops were amplified by PCR using BC6, BC7, BC8, or BC9 as templates and oligos LS1115 (SEQ ID NO: 20) and LS1117 (SEQ ID NO: 21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7, FG8, FG9, FG10, FG11, and FG12 as templates with oligonucleotides SDG10 (SEQ ID NO: 22) and SDG24 (SEQ ID NO: 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID NO: 24) and SDG28 SEQ ID N: 25). 7.5 µg of each reaction product were then digested with NotI and cleaned up with a Qiagen PCR purification column. 5.2 µg of this DNA, was ligated to an equal molar amount of RepA DNA fragment (~14 µg) digested with PspOMI and the product amplified by PCR using oligos POP2222.

Example 2: Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4).

A full description of the methods used to construct this library is described in US. Pat. Publ. No. US2013/0226834.

TCL14 library (SEQ ID NO: 7):
LPAPKNLVVSRVTEDSARLSWTAPDAAFDSFX$_1$IX$_2$YX$_3$EX$_4$X$_5$X$_6$X$_7$GE

AIVLTVPGSERSYDLTGLKPGTEYX$_8$VX$_9$IX$_{10}$GVKGGX$_{11}$X$_{12}$SX$_{13}$PL

SAIFTT;
wherein

X$_1$, X$_2$, X$_3$, X$_4$, X$_5$, X$_6$, X$_7$, X$_8$, X$_9$, X$_{10}$, X$_{11}$, X$_{12}$ and X$_{13}$ are A, D, E, F, G, H, I, K, L, N, P, Q, R, S, T, V, W, Y, C or M.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 3). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 2008) as described in Table 3. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 3.

TCL24 Library
(SEQ ID NO: 8)
LPAPKNLVVSRVTEDSARLSWTAPDAAFDSFX$_1$IX$_2$YX$_3$EX$_4$X$_5$X$_6$X$_7$GE

AIX$_8$LX$_9$VPGSERSYDLTGLKPGTEYX$_{10}$VX$_{11}$IX$_{12}$GVKGGX$_{13}$X$_{14}$

SX$_{15}$PLX$_{16}$AX$_{17}$FTT;
wherein

X$_1$, X$_2$, X$_3$, X$_4$, X$_5$, X$_6$, X$_{10}$, X$_{11}$, X$_{12}$, X$_{13}$, X$_{14}$,

X$_{15}$, X$_{16}$ and X$_{17}$ are A, D, E, F, G, H, I, K, L,

N, P, Q, R, S, T, V, Y or W.

TABLE 3

Amino acid frequency (%) at each randomized position for TCL21, TCL23, and TCL24.

| Amino Acid | TCL19 | TCL21 | TCL23 | TCL24 |
| --- | --- | --- | --- | --- |
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., *Proc Natl Acad Sci USA* 101: 2806-2810, 2004) as described above for the loop libraries.

Example 3: Selection of Fibronectin Type III (FN3) Domains that Bind PD-L1

Panning

FN3 domains specific for human PD-L1 were selected via CIS-Display (Odegrip et al 2004) using recombinant biotinylated PD-L1 (rhPD-L1/Fc Chimera, R&D Systems 156-B7). For in vitro transcription and translation (ITT), 3 μg of DNA from libraries TCL18, TCL19, TCL21, TCL23, and TCL24 were incubated at 30° C. with 0.1 mM complete amino acids, 1×S30 premix components, and 15 µL of S30 extract (Isogenica) in a total volume of 50 µL. After 1 hour, 375 µL of blocking solution (2% BSA in PBS, Invitrogen) was added and reactions were incubated on a cold block for 15 minutes. Unbound library members were removed by successive washes with TBST and TBS. After washing, DNA was eluted from the target protein by heating to 75° C. for 10 minutes and amplified by PCR using KOD polymerase for further rounds of panning High affinity binders were isolated by successively lowering the concentration of target PD-L1 during each round from 400 nM to 100 nM and increasing the washing stringency.

Outputs from the fifth round panning were subjected to four additional rounds of off-rate selection. Library transcription and translation was performed as described above after which the ITT reactions were incubated with biotinylated recombinant PD-L1 proteins and captured on neutravidin or streptavidin coated magnetic beads, before being washed in TBST extensively then subsequently washed in 5 µM cold recombinant PD-L1 protein for 1 hour. The biotinylated target antigen concentration was reduced from 25 nM in rounds 6 and 7 to 2.5 nM in rounds 8 and 9.

Following panning, genes encoding the selected FN3 domains were amplified by PCR, subcloned into a pET vector modified to include a ligase independent cloning site, and transformed into BL21 (DE3) (Stratagene) cells for soluble expression in E. coli using standard molecular biology techniques. A gene sequence encoding a C-terminal poly-histidine tag was added to each FN3 domain to enable purification and detection. Cultures were grown to an optical density of 0.6-0.8 in TB medium supplemented with 100 µg/mL carbenicillin in 1 mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen EMD Biosciences) supplemented with 0.2 mg/mL lysozyme with shaking at room temperature for 30 minutes.

Biochemical Screening for FN3 Domains that Bind Recombinant PD-L1

Streptavidin-coated Maxisorp plates (Nunc catalog 436110) were blocked for 1 h in Starting Block T20 (Pierce) and then coated with biotinylated PD-L1 (using same antigen as in panning) or negative controls (an unrelated Fc-fused recombinant protein and human serum albumin) for 1 h. Plates were rinsed with TBST and diluted lysate was applied to plates for 1 h. Following additional rinses, wells were treated with HRP-conjugated anti-FN3 domain antibody (PAB25) for 1 h and then assayed with POD (Roche catalog 11582950001). The DNA from FN3 domain lysates with ELISA binding signals to PD-L1 at least 5-fold above both Fc and HSA controls were sequenced resulting in 57 (Table 4) and 37 (Table 5) unique, readable FN3 domain sequences isolated from Round 5 and Round 9 screening respectively.

High-Throughput Expression of Anti-PD-L1 FN3 Domains 40 isolated clones from unique hits identified by biochemical binding ELISA from Round 9 were combined for growth into 96-well block plate; clones grew in 1 mL cultures (LB media supplemented with kanamycin for selection) at 37° C. overnight with shaking. For protein expression in 96-block plates, 1 mL TB media supplemented with kanamycin was inoculated with 50 µL of the overnight culture and grown at 37° C. with continual shaking at 300 rpm until $OD_{600}$=0.6-1. Once the target OD was reached, protein expression was induced with addition of IPTG to 1 mM; plates were transferred to 30° C. (300 rpm) for overnight growth. Overnight cultures were centrifuged to harvest the cells; bacterial pellets were stored at −80° C. until ready for use. Pellets were lysed with BugBuster® HT lysis buffer (Novagen EMD Biosciences) and His-tagged Centyrins purified from the clarified lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of anti-PD-L1 FN3 domains Aliquots (10)(L) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. Tencon protein was included in each run as a control. Agilent ChemStation software was used to analyse the elution profiles. 20 anti-PD-L1 FN3 domains demonstrated a retention time between 5.2 and 6.4 minutes and only a single SEC peak indicative of monomeric protein (Table 6).

TABLE 4

| Clone | ELISA PD-L1 Fc (RSU) | ELISA Fc Control (RSU) | ELISA HSA (RSU) | SEQ ID NO: |
| --- | --- | --- | --- | --- |
| ISOP121HR5P1G9 | 17760 | 880 | 1760 | 34 |
| ISOP121BR5P1F7 | 12880 | 720 | 880 | 35 |
| ISOP121BR5P1A6 | 10960 | 720 | 720 | 36 |
| ISOP121BR5P1C5 | 11680 | 400 | 720 | 37 |
| ISOP121BR5P1D7 | 12800 | 800 | 720 | 38 |
| ISOP121BR5P1C6 | 13360 | 720 | 720 | 39 |
| ISOP121AR5P1G6 | 16960 | 1200 | 880 | 40 |
| ISOP121BR5P1B7 | 11360 | 640 | 480 | 41 |
| ISOP121FR5P1G1 | 10000 | 640 | 400 | 42 |
| ISOP121GR5P1B4 | 16160 | 800 | 560 | 43 |
| ISOP121BR5P1G2 | 16720 | 800 | 560 | 44 |
| ISOP121HR5P1H2 | 20960 | 720 | 560 | 45 |
| ISOP121FR5P1G11 | 18560 | 880 | 480 | 46 |
| ISOP121AR5P1E7 | 327200 | 4240 | 6560 | 47 |
| ISOP121BR5P1F6 | 32080 | 640 | 640 | 48 |
| ISOP121BR5P1E9 | 42000 | 960 | 800 | 49 |
| ISOP121AR5P1F2 | 51040 | 880 | 960 | 50 |
| ISOP121AR5P1F7 | 64000 | 720 | 1040 | 51 |
| ISOP121BR5P1H6 | 74640 | 1440 | 1040 | 52 |
| ISOP121GR5P1A2 | 61680 | 720 | 720 | 53 |
| ISOP121BR5P1D3 | 75760 | 800 | 800 | 54 |
| ISOP121AR5P1F9 | 136080 | 1120 | 1040 | 55 |
| ISOP121AR5P1H5 | 170800 | 960 | 1120 | 56 |
| ISOP121AR5P1G10 | 231920 | 1360 | 1280 | 57 |
| ISOP121AR5P1F3 | 180160 | 800 | 960 | 58 |
| ISOP121BR5P1E2 | 137280 | 800 | 720 | 59 |
| ISOP121BR5P1D1 | 186240 | 1040 | 960 | 60 |
| ISOP121BR5P1C9 | 226400 | 1120 | 1040 | 61 |
| ISOP121GR5P1G11 | 239600 | 960 | 1040 | 62 |
| ISOP121BR5P1A7 | 388640 | 800 | 1120 | 63 |
| ISOP121BR5P1C3 | 177040 | 640 | 480 | 64 |
| ISOP121AR5P1D11 | 392800 | 640 | 1040 | 65 |
| ISOP121ER5P1E7 | 251120 | 480 | 560 | 66 |
| ISOP121GR5P1G7 | 367760 | 800 | 800 | 67 |
| ISOP121AR5P1A8 | 515920 | 560 | 1040 | 68 |
| ISOP121BR5P1E7 | 411760 | 800 | 640 | 69 |
| ISOP121FR5P1H8 | 430640 | 560 | 640 | 70 |
| ISOP121GR5P1D2 | 513280 | 720 | 640 | 71 |
| ISOP121AR5P1H2 | 926720 | 880 | 1120 | 72 |
| ISOP121GR5P1F10 | 577120 | 640 | 640 | 73 |
| ISOP121BR5P1A2 | 742800 | 720 | 800 | 74 |
| ISOP121GR5P1F7 | 697200 | 640 | 720 | 75 |
| ISOP121AR5P1B8 | 591600 | 640 | 560 | 76 |
| ISOP121GR5P1D7 | 791920 | 720 | 720 | 77 |
| ISOP121BR5P1G3 | 770800 | 560 | 640 | 78 |

TABLE 4-continued

| Clone | ELISA PD-L1 Fc (RSU) | ELISA Fc Control (RSU) | ELISA HSA (RSU) | SEQ ID NO: |
|---|---|---|---|---|
| ISOP121AR5P1C5 | 732480 | 640 | 560 | 79 |
| ISOP121FR5P1H9 | 1195520 | 720 | 880 | 80 |
| ISOP121AR5P1A10 | 788560 | 1120 | 560 | 81 |
| ISOP121HR5P1F2 | 906960 | 480 | 640 | 82 |
| ISOP121AR5P1H1 | 1475280 | 880 | 880 | 83 |
| ISOP121BR5P1D10 | 1538800 | 480 | 880 | 84 |
| ISOP121BR5P1F10 | 1422880 | 560 | 720 | 85 |
| ISOP121BR5P1D11 | 2442960 | 800 | 1120 | 86 |
| ISOP121AR5P1E11 | 1842000 | 720 | 720 | 87 |
| ISOP121BR5P1D6 | 2435760 | 560 | 880 | 88 |
| ISOP121BR5P1B5 | 1483520 | 720 | 400 | 89 |

TABLE 5

| Clone | ELISA PD-L1 Fc (RSU) | ELISA Fc Control (RSU) | ELISA HSA (RSU) | SEQ ID NO: |
|---|---|---|---|---|
| ISOP194ER9P1G3 | 4288320 | 560 | 720 | 90 |
| ISOP194AR9P1F2 | 16271040 | 1920 | 7520 | 91 |
| ISOP194AR9P1H10 | 5212800 | 4400 | 2400 | 92 |
| ISOP194BR9P1H4 | 4064960 | 3040 | 3840 | 93 |
| ISOP194AR9P1D8 | 923200 | 12000 | 6560 | 94 |
| ISOP194BR9P1D1 | 2152080 | 1360 | 1280 | 95 |
| ISOP194AR9P1E8 | 3404480 | 6960 | 67680 | 96 |
| ISOP194AR9P1E9 | 19719920 | 5520 | 1600 | 97 |
| ISOP194AR9P1H9 | 2592720 | 21280 | 11360 | 98 |
| ISOP194BR9P1A9 | 19046640 | 2320 | 3200 | 99 |
| ISOP194BR9P1A5 | 3182000 | 800 | 1280 | 100 |
| ISOP194BR9P1F7 | 15151120 | 1920 | 1760 | 101 |
| ISOP194AR9P1G7 | 15914000 | 1280 | 560 | 102 |
| ISOP194AR9P1E3 | 4566880 | 1120 | 800 | 103 |
| ISOP194AR9P1C5 | 4371120 | 3440 | 1040 | 104 |
| ISOP194AR9P1H3 | 17746800 | 9200 | 4880 | 105 |
| ISOP194GR9P1E9 | 2821920 | 720 | 1200 | 106 |
| ISOP194HR9P1B10 | 385360 | 560 | 1840 | 107 |
| ISOP194ER9P1A11 | 4352240 | 800 | 880 | 108 |
| ISOP194ER9P1A3 | 2360160 | 560 | 800 | 109 |
| ISOP194ER9P1H9 | 3042800 | 720 | 880 | 110 |
| ISOP194HR9P1B2 | 5656400 | 400 | 1840 | 111 |
| ISOP194HR9P1D11 | 6620160 | 480 | 1680 | 112 |
| ISOP194GR9P1F6 | 319200 | 400 | 1200 | 113 |
| ISOP194GR9P1F9 | 105280 | 320 | 800 | 114 |
| ISOP194GR9P1C11 | 164320 | 1040 | 1440 | 115 |
| ISOP194ER9P1E6 | 8982160 | 240 | 720 | 116 |
| ISOP194BR9P1G9 | 14376560 | 640 | 960 | 117 |
| ISOP194BR9P1E4 | 9791680 | 640 | 1440 | 118 |
| ISOP194AR9P1H1 | 21445040 | 15680 | 6800 | 119 |
| ISOP194BR9P1D10 | 1666880 | 720 | 1120 | 120 |
| ISOP194BR9P1C8 | 6110640 | 640 | 1280 | 121 |
| ISOP194AR9P1C10 | 13863040 | 38240 | 14960 | 122 |
| ISOP194AR9P1D11 | 1043280 | 28160 | 12720 | 123 |
| ISOP194AR9P1C3 | 3548240 | 56400 | 5920 | 124 |

TABLE 6

| Clone | SEC Retention Time (min) | SEC Peak Height (mAU) | Monomeric? | SEQ ID NO: |
|---|---|---|---|---|
| ISOP194ER9P1G3 | 5.951 | 167.47 | FALSE | 90 |
| ISOP194AR9P1F2 | 5.901 | 552.30 | TRUE | 91 |
| ISOP194AR9P1H10 | 5.976 | 12.80 | FALSE | 92 |
| ISOP194BR9P1H4 | 5.688 | 394.40 | TRUE | 93 |
| ISOP194AR9P1D8 | 5.711 | 162.07 | FALSE | 94 |
| ISOP194BR9P1D1 | 6.696 | 88.56 | TRUE | 95 |
| ISOP194AR9P1E8 | 5.549 | 570.07 | TRUE | 96 |
| ISOP194AR9P1E9 | 5.79 | 493.72 | TRUE | 97 |
| ISOP194AR9P1H9 | 5.694 | 511.99 | TRUE | 98 |
| ISOP194BR9P1A9 | 5.662 | 225.76 | FALSE | 99 |
| ISOP194BR9P1A5 | 7.82 | 15.28 | FALSE | 100 |
| ISOP194BR9P1F7 | 5.982 | 94.57 | TRUE | 101 |
| ISOP194AR9P1G7 | 5.845 | 50.19 | TRUE | 102 |
| ISOP194AR9P1E3 | 6.939 | 15.65 | FALSE | 103 |
| ISOP194AR9P1C5 | No peak | | FALSE | 104 |
| ISOP194AR9P1H3 | 6.238 | 155.66 | TRUE | 105 |
| ISOP194GR9P1E9 | 6.343 | 20.59 | TRUE | 106 |
| ISOP194HR9P1B10 | 5.911 | 398.72 | TRUE | 107 |
| ISOP194ER9P1A11 | 5.957 | 154.65 | TRUE | 108 |
| ISOP194ER9P1A3 | 5.976 | 341.20 | TRUE | 109 |
| ISOP194ER9P1H9 | No peak | | FALSE | 110 |
| ISOP194HR9P1B2 | 6.274 | 2.33 | FALSE | 111 |
| ISOP194HR9P1D11 | 6.002 | 433.98 | FALSE | 112 |
| ISOP194GR9P1F6 | 6.12 | 29.42 | TRUE | 113 |
| ISOP194GR9P1F9 | No peak | | FALSE | 114 |
| ISOP194GR9P1C11 | 12.458 | 2.90 | FALSE | 115 |
| ISOP194ER9P1E6 | 6.125 | 149.28 | TRUE | 116 |
| ISOP194BR9P1G9 | 6.622 | 84.28 | FALSE | 117 |
| ISOP194BR9P1E4 | 5.714 | 456.33 | TRUE | 118 |
| ISOP194AR9P1H1 | 6.247 | 12.76 | FALSE | 119 |
| ISOP194BR9P1D10 | 6.059 | 10.60 | FALSE | 120 |
| ISOP194BR9P1C8 | No peak | | FALSE | 121 |
| ISOP194AR9P1C10 | 5.715 | 98.64 | TRUE | 122 |
| ISOP194AR9P1D11 | No peak | | FALSE | 123 |
| ISOP194AR9P1C3 | 5.588 | 700.26 | TRUE | 124 |

```
Sequences

SEQ ID No. 1 = Original Tencon Sequence

LPAPKNLVVSEVTEDSLRLSWTAPDAAFDSFLIQYQESEKVGEAINLTVPGSERSY
DLTGLKPGTEYTVSIYGVKGGHRSNPLSAEFTT

SEQ ID No. 2 = TCL1 library

LPAPKNLVVSEVTEDSLRLSWTAPDAAFDSFLIQYQESEKVGEAINLTVPGSERSY
DLTGLKPGTEYTVSIYGVX₁X₂X₃X₄X₅X₆X₇X₈X₉X₁₀X₁₁X₁₂ PLSAEFTT;
wherein
X₁, X₂, X₃, X₄, X₅, X₆, X₇ is any amino acid; and
X₈, X₉, X₁₀, X₁₁ and X₁₂ are any amino acid or deleted SEQ ID No. 3 = TCL2 library LPAPKNLVVSEVTEDSLRLSWX₁X₂X₃X₄X₅X₆X₇X₈SFLIQYQESEKVGEAINLTVPGS
ERSYDLTGLKPGTEYTVSIYGVX₉X₁₀X₁₁X₁₂X₁₃SX₁₄X₁₅LSAEFTT;
```

-continued wherein
X$_1$ is Ala, Arg, Asn, Asp, Glu, Gln, Gly, His, Ile, Leu, Lys, Phe, Pro, Ser, Thr, Trp, Tyr or Val;
X$_2$ is Ala, Arg, Asn, Asp, Glu, Gln, Gly, His, Ile, Leu, Lys, Phe, Pro, Ser, Thr, Trp, Tyr or Val;
X$_3$ Ala, Arg, Asn, Asp, Glu, Gln, Gly, His, Ile, Leu, Lys, Phe, Pro, Ser, Thr, Trp, Tyr or Val;
X$_4$ is Ala, Arg, Asn, Asp, Glu, Gln, Gly, His, Ile, Leu, Lys, Phe, Pro, Ser, Thr, Trp, Tyr or Val;
X$_5$ is Ala, Arg, Asn, Asp, Glu, Gln, Gly, His, Ile, Leu, Lys, Phe, Pro, Ser, Thr, Trp, Tyr or Val;
X$_6$ is Ala, Arg, Asn, Asp, Glu, Gln, Gly, His, Ile, Leu, Lys, Phe, Pro, Ser, Thr, Trp, Tyr or Val;
X$_7$ is Phe, Ile, Leu, Val or Tyr;
X$_8$ is Asp, Glu or Thr;
X$_9$ is Ala, Arg, Asn, Asp, Glu, Gln, Gly, His, Ile, Leu, Lys, Phe, Pro, Ser, Thr, Trp, Tyr or Val;
X$_{10}$ is Ala, Arg, Asn, Asp, Glu, Gln, Gly, His, Ile, Leu, Lys, Phe, Pro, Ser, Thr, Trp, Tyr or Val;
X$_{11}$ is Ala, Arg, Asn, Asp, Glu, Gln, Gly, His, Ile, Leu, Lys, Phe, Pro, Ser, Thr, Trp, Tyr or Val;
X$_{12}$ is Ala, Arg, Asn, Asp, Glu, Gln, Gly, His, Ile, Leu, Lys, Phe, Pro, Ser, Thr, Trp, Tyr or Val;
X$_{13}$ is Ala, Arg, Asn, Asp, Glu, Gln, Gly, His, Ile, Leu, Lys, Phe, Pro, Ser, Thr, Trp, Tyr or Val;
X$_{14}$ is Ala, Arg, Asn, Asp, Glu, Gln, Gly, His, Ile, Leu, Lys, Phe, Pro, Ser, Thr, Trp, Tyr or Val;
and
X$_{15}$ is Ala, Arg, Asn, Asp, Glu, Gln, Gly, His, Ile, Leu, Lys, Phe, Pro, Ser, Thr, Trp, Tyr or Val.

SEQ ID No. 4 = Stabilized Tencon

LPAPKNLVVSRVTEDSARLSWTAPDAAFDSFLIQYQESEKVGEAIVLTVPGSERSY
DLTGLKPGTEYTVSIYGVKGGHRSNPLSAIFTT

SEQ ID No. 5 = TCL7 (FG and BC loops)

LPAPKNLVVSRVTEDSARLSWX$_1$X$_2$X$_3$X$_4$X$_5$X$_6$X$_7$X$_8$X$_9$FDSFLIQYQESEKVGEAIVLT
VPGSERSYDLTGLKPGTEYTVSIYGVX$_{10}$X$_{11}$X$_{12}$X$_{13}$X$_{14}$X$_{15}$X$_{16}$X$_{17}$X$_{18}$X$_{19}$SNPLSAIFTT;
wherein
X$_1$, X$_2$, X$_3$, X$_4$, X$_5$, X$_6$, X$_{10}$, X$_{11}$, X$_{12}$, X$_{13}$, X$_{14}$, X$_{15}$ and X$_{16}$ are
A, D, E, F, G, H, I, K, L, N, P, Q, R, S, T, V, W or Y;
and
X$_7$, X$_8$, X$_9$, X$_{17}$, X$_{18}$ and X$_{19}$, are A, D, E, F, G, H, I, K, L, N, P, Q, R, S, T, V, W, Y or deleted SEQ ID No. 6 = TCL9 (FG loop)

LPAPKNLVVSRVTEDSARLSWTAPDAAFDSFLIQYQESEKVGEAIVLTVPGSERSY
DLTGLKPGTEYTVSIYGVX$_1$X$_2$X$_3$X$_4$X$_5$X$_6$X$_7$X$_8$X$_9$X$_{10}$X$_{11}$X$_{12}$SNPLSAIFTT;
wherein
X$_1$, X$_2$, X$_3$, X$_4$, X$_5$, X$_6$ and X$_7$, is A, D, E, F, G, H, I, K, L, N, P, Q, R, S, T, V, W or Y;
and
X$_8$, X$_9$, X$_{10}$, X$_{11}$ and X$_{12}$ is A, D, E, F, G, H, I, K, L, N, P, Q, R, S, T, V, W, Y or deleted.

TCL14 library (SEQ ID NO: 7):

LPAPKNLVVSRVTEDSARLSWTAPDAAFDSFX$_1$IX$_2$YX$_3$EX$_4$X$_5$X$_6$X$_7$GEAIVLTVPGS
ERSYDLTGLKPGTEYX$_8$VX$_9$IX$_{10}$GVKGGX$_{11}$X$_{12}$SX$_{13}$PLSAIFTT;
wherein
X$_1$, X$_2$, X$_3$, X$_4$, X$_5$, X$_6$, X$_7$, X$_8$, X$_9$, X$_{10}$, X$_{11}$, X$_{12}$ and X$_{13}$ are A, D, E, F, G, H, I, K, L, N, P, Q, R, S, T, V, W, Y, C or M.

TCL24 Library (SEQ ID NO: 8)

LPAPKNLVVSRVTEDSARLSWTAPDAAFDSFX$_1$IX$_2$YX$_3$EX$_4$X$_5$X$_6$X$_7$GEAIX$_8$LX$_9$VPG
SERSYDLTGLKPGTEYX$_{10}$VX$_{11}$IX$_{12}$GVKGGX$_{13}$X$_{14}$SX$_{15}$PLX$_{16}$AX$_{17}$FTT;
wherein
X$_1$, X$_2$, X$_3$, X$_4$, X$_5$, X$_6$, X$_{10}$, X$_{11}$, X$_{12}$, X$_{13}$, X$_{14}$, X$_{15}$, X$_{16}$ and X$_{17}$ are A, D, E, F, G, H, I, K, L, N, P, Q, R, S, T, V, Y or W.

SEQ ID No. 9 = Sloning-FOR

GTGACACGGCGGTTAGAAC

-continued

SEQ ID No. 10 = Sloning-REV

GCCTTTGGGAAGCTTCTAAG

SEQ ID No. 11 = POP2250

CGGCGGTTAGAACGCGGCTACAATTAATAC

SEQ ID No. 12 = DigLigRev

CATGATTACGCCAAGCTCAGAA

SEQ ID No. 13 = BC9

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTGAAGTTACCGAAGACTCTCTGCGTCTGTCTTGGNNNNNNNNNNNNNNN
NNNNNNNNNNNNTTYGACTCTTTCCTGATCCAGTACCAGGAATCTGAAAAAGT
TGGTGAAGCGATCAACCTGACCGTTCCGGGTTCTGAACGTTCTTACGACCTGA
CCGGTCTGAAACCGGGTACCGAATACACCGTTTCTATCTACGGTGTTCTTAGA
AGCTTCCCAAAGGC

SEQ ID No. 14 = BC8

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTGAAGTTACCGAAGACTCTCTGCGTCTGTCTTGGNNNNNNNNNNNNNNN
NNNNNNNNTTYGACTCTTTCCTGATCCAGTACCAGGAATCTGAAAAAGTTGG
TGAAGCGATCAACCTGACCGTTCCGGGTTCTGAACGTTCTTACGACCTGACCG
GTCTGAAACCGGGTACCGAATACACCGTTTCTATCTACGGTGTTCTTAGAAGC
TTCCCAAAGGC

SEQ ID No. 15 = BC7

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTGAAGTTACCGAAGACTCTCTGCGTCTGTCTTGGNNNNNNNNNNNNNNN
NNNNNNTTYGACTCTTTCCTGATCCAGTACCAGGAATCTGAAAAAGTTGGTGA
AGCGATCAACCTGACCGTTCCGGGTTCTGAACGTTCTTACGACCTGACCGGTC
TGAAACCGGGTACCGAATACACCGTTTCTATCTACGGTGTTCTTAGAAGCTTCC
CAAAGGC

SEQ ID No. 16 = BC6

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTGAAGTTACCGAAGACTCTCTGCGTCTGTCTTGGNNNNNNNNNNNNNNN
NNNNTTYGACTCTTTCCTGATCCAGTACCAGGAATCTGAAAAAGTTGGTGAAGC
GATCAACCTGACCGTTCCGGGTTCTGAACGTTCTTACGACCTGACCGGTCTGA
AACCGGGTACCGAATACACCGTTTCTATCTACGGTGTTCTTAGAAGCTTCCCA
AAGGC

SEQ ID No. 17 = 130mer-L17A

CGGCGGTTAGAACGCGGCTACAATTAATACATAACCCCATCCCCCTGTTGACA
ATTAATCATCGGCTCGTATAATGTGTGGAATTGTGAGCGGATAACAATTTCAC
ACAGGAAACAGGATCTACCATGCTG

SEQ ID No. 18 = POP222ext

CGG CGG TTA GAA CGC GGC TAC AAT TAA TAC

SEQ ID No. 19 = LS1114

CCA AGA CAG ACG GCA GAG TC TTC GGT AAC GCG AGA AAC AAC CAG
GTT TTT CGG CGC CGG CAG CAT GGT AGA TCC TGT TTC

SEQ ID No. 20 = LS1115

CCG AAG ACT CTG CCC GTC TGT CTT GG

SEQ ID No. 21 = LS1117

CAG TGG TCT CAC GGA TTC CTG GTA CTG GAT CAG GAA AGA GTC GAA

| SEQ ID No. 22 = SDG10 |
| --- |

CATGCGGTCTCTTCCGAAAAAGTTGGTGAAGCGATCGTCCTGACCGTTCCGGG
T

| SEQ ID No. 23 = SDG24 |
| --- |

GGTGGTGAAGATCGCAGACAGCGGGTTAG

| SEQ ID No. 24 = POP2222 |
| --- |

CGGCGGTTAGAACGCGGCTAC

| SEQ ID No. 25 = SDG28 |
| --- |

AAGATCAGTTGCGGCCGCTAGACTAGAACCGCTGCCACCGCCGGTGGTGAAG
ATCGCAGAC

| SEQ ID No. 26 = FG12 |
| --- |

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTCGCGTTACCGAAGACTCTGCGCGTCTGTCTTGGACCGCGCCGGACGCG
GCGTTCGACTCTTTCCTGATCCAGTACCAGGAATCTGAAAAAGTTGGTGAAGC
GATCGTGCTGACCGTTCCGGGTTCTGAACGTTCTTACGACCTGACCGGTCTGA
AACCGGGTACCGAATACACCGTTTCTATCTACGGTGTTNNNNNNNNNNNNNNN
NNNNNNNNNNNNNNNNNNNNTCTAACCCGCTGTCTGCGATCTTCACCACC
GGCGGTCACCATCACCATCACCATGGCAGCGGTTCTAGTCTAGCGGCCGCAAC
TGATCTTGGC

| SEQ ID No. 27 = FG11 |
| --- |

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTCGCGTTACCGAAGACTCTGCGCGTCTGTCTTGGACCGCGCCGGACGCG
GCGTTCGACTCTTTCCTGATCCAGTACCAGGAATCTGAAAAAGTTGGTGAAGC
GATCGTGCTGACCGTTCCGGGTTCTGAACGTTCTTACGACCTGACCGGTCTGA
AACCGGGTACCGAATACACCGTTTCTATCTACGGTGTTNNNNNNNNNNNNNNN
NNNNNNNNNNNNNNNNNNNTCTAACCCGCTGTCTGCGATCTTCACCACCGGC
GGTCACCATCACCATCACCATGGCAGCGGTTCTAGTCTAGCGGCCGCAACTGA
TCTTGGC

| SEQ ID No. 28 = FG10 |
| --- |

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTCGCGTTACCGAAGACTCTGCGCGTCTGTCTTGGACCGCGCCGGACGCG
GCGTTCGACTCTTTCCTGATCCAGTACCAGGAATCTGAAAAAGTTGGTGAAGC
GATCGTGCTGACCGTTCCGGGTTCTGAACGTTCTTACGACCTGACCGGTCTGA
AACCGGGTACCGAATACACCGTTTCTATCTACGGTGTTNNNNNNNNNNNNNNN
NNNNNNNNNNNNNNNNNTCTAACCCGCTGTCTGCGATCTTCACCACCGGCGGTC
ACCATCACCATCACCATGGCAGCGGTTCTAGTCTAGCGGCCGCAACTGATCTT
GGC

| SEQ ID No. 29 = FG9 |
| --- |

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTCGCGTTACCGAAGACTCTGCGCGTCTGTCTTGGACCGCGCCGGACGCG
GCGTTCGACTCTTTCCTGATCCAGTACCAGGAATCTGAAAAAGTTGGTGAAGC
GATCGTGCTGACCGTTCCGGGTTCTGAACGTTCTTACGACCTGACCGGTCTGA
AACCGGGTACCGAATACACCGTTTCTATCTACGGTGTTNNNNNNNNNNNNNNN
NNNNNNNNNNNNNTCTAACCCGCTGTCTGCGATCTTCACCACCGGCGGTCACC
ATCACCATCACCATGGCAGCGGTTCTAGTCTAGCGGCCGCAACTGATCTTGGC

| SEQ ID No. 30 = FG8 |
| --- |

GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTCGCGTTACCGAAGACTCTGCGCGTCTGTCTTGGACCGCGCCGGACGCG
GCGTTCGACTCTTTCCTGATCCAGTACCAGGAATCTGAAAAAGTTGGTGAAGC
GATCGTGCTGACCGTTCCGGGTTCTGAACGTTCTTACGACCTGACCGGTCTGA
AACCGGGTACCGAATACACCGTTTCTATCTACGGTGTTNNNNNNNNNNNNNNN

-continued

```
NNNNNNNNNNTCTAACCCGCTGTCTGCGATCTTCACCACCGGCGGTCACCATC
ACCATCACCATGGCAGCGGTTCTAGTCTAGCGGCCGCAACTGATCTTGGC
```

SEQ ID No. 31 = FG7

```
GTGACACGGCGGTTAGAACGCGGCTACAATTAATACATAACCCCATCCCCCTG
TTGACAATTAATCATCGGCTCGTATAATGTGTGGAATTGTGAGCGGATAACAA
TTTCACACAGGAAACAGGATCTACCATGCTGCCGGCGCCGAAAAACCTGGTTG
TTTCTCGCGTTACCGAAGACTCTGCGCGTCTGTCTTGGACCGCGCCGGACGCG
GCGTTCGACTCTTTCCTGATCCAGTACCAGGAATCTGAAAAAGTTGGTGAAGC
GATCGTGCTGACCGTTCCGGGTTCTGAACGTTCTTACGACCTGACCGGTCTGA
AACCGGGTACCGAATACACCGTTTCTATCTACGGTGTTNNNNNNNNNNNNNN
NNNNNNNTCTAACCCGCTGTCTGCGATCTTCACCACCGGCGGTCACCATCACC
ATCACCATGGCAGCGGTTCTAGTCTAGCGGCCGCAACTGATCTTGGC
```

SEQ ID NO: 32 = human mature PD-L1

```
FTVTVPKDLYVVEYGSNMTIECKFPVEKQLDLAALIVYWEMEDKNIIQFVHGEED
LKVQHSSYRQRARLLKDQLSLGNAALQITDVKLQDAGVYRCMISYGGADYKRIT
VKVNAPYNKINQRILVVDPVTSEHELTCQAEGYPKAEVIWTSSDHQVLSGKTTTT
NSKREEKLFNVTSTLRINTTTNEIFYCTFRRLDPEENHTAELVIPELPLAHPPNER
```

SEQ ID NO: 33 = human mature PD-1

```
PGWFLDSPDRPWNPPTFSPALLVVTEGDNATFTCSFSNTSESFVLNWYRMSPSNQT
DKLAAFPEDRSQPGQDCRFRVTQLPNGRDFHMSVVRARRNDSGTYLCGAISLAPK
AQIKESLRAELRVTERRAEVPTAHPSPSPRPAGQFQTLVVGVVGGLLGSLVLLVW
VLAVICSRAARGTIGARRTGQPLKEDPSAVPVFSVDYGELDFQWREKTPEPPVPCV
PEQTEYATIVFPSGMGTSSPARRGSADGPRSAQPLRPE DGHCSWPL
```

| Clone | SEQ ID NO: | AA Sequence |
|---|---|---|
| ISOP121HR5P1G9 | 34 | LPAPKNLVVSRVTEDSARLSWTAPDAAFDSFPINYGERATKGEAINLYVPGSERSYDLTGLKPGTEYWVLIGGVKGGLKSSPLWAWFTT |
| ISOP121BR5P1F7 | 35 | LPAPKNLVVSRVTEDSARLSWHDATWQYFDSFLIQYQESEKVGEAIVLIVPGSERSYDLTGLKPGTEYTVSIYGVFHRKHIDFVSNPLSAIFTT |
| ISOP121BR5P1A6 | 36 | LPAPKNLVVSRVTEDSARLSWASWLVAFFDSFLIQYQESEKVGEAIVLIVPGSERSYDLTGLKPGTEYTVSIYGVYQRHASAFVSNPLSAIFTT |
| ISOP121BR5P1C5 | 37 | LPAPKNLVVSRVTEDSARLSWFRLRIVQTFDSFLIQYQESEKVGEAIVLIVPGSERSYDLTGLKPGTEYTVSIYGVITVVELLQQSNPLSAIFTT |
| ISOP121BR5P1D7 | 38 | LPAPKNLGCFSRYRRLSRLSWETPYPSLSNFDSFLIQYQESEKVGEAIVLIVPGSERSYDLTGLKPGTEYTVSIYGVLKLSAAWWPSNPLSAIFTT |
| ISOP121BR5P1C6 | 39 | LPAPKNLVVSRVTEDSARLSWRKQEQYFDSFLIQYQESEKVGEAIVLTVPGSERSYDLTGLKPGTEYTVSIYGVYSRPKAEFTSNPLSAIFTT |
| ISOP121AR5P1G6 | 40 | LPAPKNLVVSRVTEDSARLSWHATFGDPFDSFLIQYQESEKVGEAIVLTVPGSERSYDLTGLKPGTEYIVSIYGVRHYTVYDSNPLSAIFTT |
| ISOP121BR5P1B7 | 41 | LPAPKNLVVSRITEDSARLSWKWEEGFFDSFLIQYQESEKVGEAIVLTVPGSERSYDLTGLKPGTEYTVSIYGVYQRHASAFVSNPLSAIFTT |
| ISOP121FR5P1G1 | 42 | LPAPKNLVVSRVTEDSARLSWTAPDAAFDSFWIHYTEAPVHGEAIVLTVPGSERSYDLTGLKPGTEYTVVIWGVKGGTWSSPLSAIFTT |
| ISOP121GR5P1B4 | 43 | LPAPKNLIVSRVTEDSARLSWTAPDAAFDSFPINYGERATKGEAINLYVPGSERSYDLTGLKPGTEYWVLIGGVKGGLKSSPLWAWFTT |
| ISOP121BR5P1G2 | 44 | LPAPKNLVVSRVTEDSARLSWADELHHANHFDSFLIQYQESEKVGEAIVLTVPGSERSYDLTGLKPGTEYTVSIYGVYDRHYEIHFYSNPLSAIFTT |

| | | |
|---|---|---|
| ISOP121HR5P1H2 | 45 | LPAPKNLVVSRVTEDSARLSWTAPDAAFDSFDIYYLEYDYSGEA IVLTVPGSERSYDLTGLKPGTEYDVLIIGVKGGSLSTPLSAIFTT |
| ISOP121FR5P1G11 | 46 | LPAPKNLVVSRVTEDSARLSWTAPDAAFDSFSIWYLEIVAHGE AIVLTVPGSERSYDLTGLKPGTEYEVIIHGVKGCGPSGPLSAIFTT |
| ISOP121AR5P1E7 | 47 | LPAPKNLVVSRVTEDSARLSWHVYHEIDYFDSFLIQYQESEKVG EAIVLTVPGSERSYDLTGLKPGTEYIVSIYGVYQRKVEFYSNPLS AIFTT |
| ISOP121GR5P1F6 | 48 | LPAPKNLVVSRVTEDSARLSWTAPDAAFDSFDIRYHEYTWPGE AIVLLVPGSERSYDLTGLKPGTEYGVYINGVKGGFRSKPLFAWF TTGG |
| ISOP121BR5P1E9 | 49 | LPAPKNLVVSRVTEDSARLSWDSYRDYFDSFLIQYQESEKVGEA IVLTVPGSERSYDLTGLKPGTEYTVSIYGVYSRKHVVFVQSNPLS AIFTT |
| ISOP121AR5P1F2 | 50 | LPAPKNLVISRVTEDSARLSWGWSELIATHFDSFLIQYQESEKV GEAIVLTVPGSERSYDLTGLKPGTEYTVSIYGVYNRKVNFYSNPL SAIFTT |
| ISOP121AR5P1F7 | 51 | LPAPKNLVVSRVTEDSARLSWQEHWDTSSNFDSFLIQYQESEK VGEAIVLTVPGSERSYDLTGLKPGTEYTISIYGVYNRKVLFYSNPL SAIFTT |
| ISOP121BR5P1H6 | 52 | LPAPKNLVVSRVTEDSARLSWGYIDVSYFDSFLIQYQESEKVGE AIVLTVPGSERSYDLTGLKPGTEYTVSIYGVYSRPKAEFTSNPLSA IFTT |
| ISOP121GR5P1A2 | 53 | LPAPKNLVVSRVTEDSARLSWTAPDAAFDSFKIQYIERYIPGEAI QLNVPGSERSYDLTGLKPGTEYSVIIPGVKGGRNSFPLWAWFT T |
| ISOP121BR5P1D3 | 54 | LPAPKNLVVSRVTEDSARLSWYEDNTERFDSFLIQYQESEKVGE AIVLTVPGSERSYDLTGLKPGTEYTVSIYGVYIRVQVLWFSNPLS AIFTT |
| ISOP121AR5P1F9 | 55 | LPAPKNLVVSRVTEDSARLSWGWSELIATHFDSFLIQYQESEKV GEAIVLTVPGSERSYDLTGLKPGTEYTVSIYGVYNRKVNFYSNPL SAIFTT |
| ISOP121AR5P1H5 | 56 | LPAPKNLVVSRVTEDSARLSWEDAVKHIWFDSFLIQYQESEKV GEAIVLTVPGSERSYDLTGLKPGTEYTVSIYGVWIASVWRSNPL SAIFTT |
| ISOP121AR5P1G10 | 57 | LPAPKNLVVSRVTEDSARLSWEWLEHFDSFLIQYQESEKVGEAI VLTVPGSERSYDLTGLKPGTEYTVSIYGVYQRKVEFHSNPLSAIF TTT |
| ISOP121AR5P1F3 | 58 | LPAPKNLVVSRVTEDSARLSWPFNNYSEHFDSFLIQYQESEKVG EAIVLTVPGSERSYDLTGLKPGTEYTVSIYGVYERKTAFYSNPLSA IFTT |
| ISOP121BR5P1E2 | 59 | LPAPKNLVVSRVTEDSARLSWWFPLEWFDSFLIQYQESEKVGE AIVLTVPGSERSYDLTGLKPGTEYTVSIYGVYTREHKSVWASNP LSAIFTT |
| ISOP121BR5P1D1 | 60 | LPAPKNLVVSRVTEDSARLSWKWGGEFFDSFLIQYQESEKVGE AIVLTVPGSERSYDLTGLKPGTEYTVSIYGVYQRNWHHWYSNP LSAIFTT |
| ISOP121BR5P1C9 | 61 | LPAPKNLVVSRVTEDSARLSWIWPDKHEFFDSFLIQYQESEKVG EAIVLTVPGSERSYDLTGLKPGTEYTVSIYGVYDRKYANWSSNP LSAIFTT |
| ISOP121GR5P1G11 | 62 | LPAPKNLVVSRVTEDSARLSWTAPDAAFDSFQINYHEYGQNG EAIQLIVPGSERSYDLTGLKPGTEYGVWIWGVKGGIRSKPLWA FFTT |
| ISOP121BR5P1A7 | 63 | LPAPKNLVVSRVTEDSARLSWTTAFHNEYFDSFLIQYQESEKVG EAIVLTVPGSERSYDLTGLKPGTEYTVSIYGVYSRPKAEFTSNPLS AIFTT |
| ISOP121BR5P1C3 | 64 | LPAPKNLVVSRVTEDSARLSWASARDYFDSFLIQYQESEKVGEA IVLTVPGSERSYDLTGLKPGTEYTVSIYGVLAIAQITHWFSNPLS AIFTT |

| | | |
|---|---|---|
| ISOP121AR5P1D11 | 65 | LPAPKNLVVSRVTEDSARLSWEWLEHFDSFLIQYQESEKVGEAI VLTVPGSERSYDLTGLKPGTEYTVSIYGVYQRKVEFHSNPLSAIF TT |
| ISOP121ER5P1E7 | 66 | LPAPKNLVVSRVTEDSARLSWTAPDAAFDSFTIGYTETPPRGEA IVLTVPGSERSYDLTGLKPGTKYYVSILGVKGGLGSWPLSAIFTT |
| ISOP121GR5P1G7 | 67 | LPAPKNLVVSRVTEDSARLSWTAPDAAFDSFHIRYHEYDKNGE AIQLYVPGSERSYDLTGLKPGTEYGVYIHGVKGGGRSKPLWAH FTT |
| ISOP121AR5P1A8 | 68 | LPAPKNLVVSRVTEDSARLSWGLEWAYQFFDSFLIQYQESEKV GEAIVLTVPGSERSYDLTGLKPGTEYTVSIYGVYLRAIEFYSNPLS AIFTT |
| ISOP121BR5P1E7 | 69 | LPAPKNLVVSRVTEDSARLSWRKQEQYFDSFLIQYQESEKVGE AIVLTVPGSERSYDLTGLKPGTEYTVSIYGVKKWPSTTTTSNPLS AIFTT |
| ISOP121FR5P1H8 | 70 | LPAPKNLVVSRVTEDSARLSWTAPDAAFDSFVIYYSEQHFYGE AIVLTVPGSERSYDLTGLKPGTEYVVKIYGVKGGETSKPLSAIFTT |
| ISOP121GR5P1D2 | 71 | LPAPKNLVVSRVTEDSARLSWTAPDAAFDSFHILYQERAQSGE AIGLVVPGSERSYDLTGLKPATEYSVQIFGVKGGKLSNPLWAW FTT |
| ISOP121AR5P1H2 | 72 | LPAPKNLVVSRVTEDSARLSWVIDEFIPLFDSFLIQYQESEKVGE AIVLTVPGSERSYDLTGLKPGTEYTVSIYGVLAKNIGISNPL- SAIFT T |
| ISOP121GR5P1F10 | 73 | LPAPKNLVVSRVTEDSARLSWTAPDAAFDSFFIDYVERATVGE AIALNVPGSKRSYALTGLKPGTEYFVKIRGVKGGLKSKPLWAW FTT |
| ISOP121BR5P1A2 | 74 | LPAPKNLVVSRVTEDSARLSWRFSQEWFDSFLIQYQESEKVGE AIVLTVPGSERSYDLTGLKPGTEYTVSIYGVYARGIHKWLSNPLS AIFTT |
| ISOP121GR5P1F7 | 75 | LPAPKNLVVSRVTEDSARLSWTAPDAAFDSFGINYVERASEGE AIDLGVPGSERSYDLTGLKPGTEYFVKIFGVKGGIPSVPLWAWF TT |
| ISOP121AR5P1B8 | 76 | LPAPKNLVISRVTEDSARLSWDKRTQFAFDSFLIQYQESEKVGE AIVLTVPGSERSYDLTGLKPGTEYTVSIYGVPTWSGRTQSNPLS AIFTT |
| ISOP121GR5P1D7 | 77 | LPAPKNLVVSRVTEDSARLSWTAPDAAFDSFKIWYQERSIVGE AIFLLVPGSERSYDLTGLKPGTEYIVQIFGVKGGPYSNPLWAPFT T |
| ISOP121BR5P1G3 | 78 | LPAPKNLVVSRVTEDSARLSWKQRTSFHFDSFLIQYQESEKVGE AIVLTVPGSERSYDLTGLKPGTEYTVSIYGVPFWQQWQPESNP LSAIFTT |
| ISOP121AR5P1C5 | 79 | LPAPKNLVVSRVTEDSARLSWKRSDDEWFDSFLIQYQESEKVG EAIILTVPGSERSYDLTGLKPGTEYTVSIYGVYQRAALWFSNPLS AIFTT |
| ISOP121FR5P1H9 | 80 | LPAPKNLVVSRVTEDSARLSWTAPDAAFDSFSILYGETAPIGEAI VLTVPGSERSYDLTGLKPGTEYVVYIQGVKGGNYSQPLSAIFTT |
| ISOP121AR5P1A10 | 81 | LPAPKNLVVSRVTEDSARLSWPDWSNSEYFDSFLIQYQESEKV GEAIVLTVPGSERSYDLTGLKPGTEYIVSIYGVYARHRLFVSNPL SAIFTT |
| ISOP121HR5P1F2 | 82 | LPAPKNLVVSRVTEDSARLSWTAPDAAFDSFTILYGETYSGGEA IVLTVPGSERSYDLTGLKPGTEYVVYIFGVKGGKWSRPLSAIFTT |
| ISOP121AR5P1H1 | 83 | LPAPKNLVVSRVTEDSARLSWKQATKFVFDSFLIQYQESEKVGE AIVLTVPGSERSYDLTGLKPGTEYTVSIYGVPDWFVLESNPLSAI FTT |
| ISOP121BR5P1D10 | 84 | LPAPKNLVVSRVTEDSARLSWGKKSHFFDSFLIQYQESEKVGEA IVLTVPGSERSYDLTGLKPGTEYTVSIYGVYTRGQCEWESNQLS AIFFTT |
| ISOP121BR5P1F10 | 85 | LPAPKNLVVSRVTEDSARLSWPLNLEYFDSFLIQYQESEKVGEAI VLTVPGSERSYDLTGLKPGTEYTVSIYGVYGRYGGPFVSNPLSAI FTT |

-continued

| | | |
|---|---|---|
| ISOP121BR5P1D11 | 86 | LPAPKNLVVSRVTEDSARLSWFNADEEYFDSFLIQYQESEKVGE AIVLTVPGSERSYDLTGLKPGTEYTVSIYGVYVRAVRFVSSNPLS AIFTT |
| ISOP121AR5P1E11 | 87 | LPAPKNLVVSRVTEDSARLSWSVQTSFVFDSFLIQYQESEKVGE AIVLTVPGSERSYDLTGLKPGTEYTVSIYGVPLWHGFDSNPLSAI FTT |
| ISOP121BR5P1D6 | 88 | LPAPKNLVVSRVTEDSARLSWKQGTSFHFDSFLIQYQESEKVGE AIVLTVPGSERSYDLTGLKPGTEYTVSIYGVQLLANDIISSNPL- SAI FTT |
| ISOP121BR5P1B5 | 89 | LPAPKNLVVSRVTEDSARLSWRKQEQYFDSFLIQYQESEKVGE AIVLTVPGSERSYDLTGLKPGTEYTVSIYGVYQRGYHNWFSNPL SAIFTT |
| ISOP194ER9P1G3 | 90 | LPAPKNLIVSRVTEDSARLSWTAPDAAFDSFRIAYYETMVSGEA IVLTVPGSERSYDLTGLKPGTEYAVIIKGVKGGKPSWPLSAIFTT |
| ISOP194AR9P1F2 | 91 | LPAPKNLVISRVTEDSARLSWELEHFDSFLIQYQESEKVGEAI VLTVPGSERSYDLTGLKPGTEYTVSIYGVYNRKVNFYSNPLSAIF TT |
| ISOP194AR9P1H10 | 92 | LPAPKNLVISRVTEDSARLSWPAHYHSAFFDSFLIQYQESEKVG EAIVLTVPGSERSYDLTGLKPGTEYIVSIYGVYQRKVEFHSNPLS AIFTT |
| ISOP194BR9P1H4 | 93 | LPAPKNLVVSRVTEDSACLSWTTAFHNEYFDSFLIQYQESEKVG EAIVLTVPGSERSYDLTGLKPGTEYTVSIYGVYSRPKAEFTSNPLS AIFTT |
| ISOP194AR9P1D8 | 94 | LPAPKNLVVSRVTEDSARLSWDTWNDFFDSFLIQYQESEKVGE AIVLTVPGSERSYDLTGLKPGTEYTVSIYGVYQRKVIWLSNPLSA IFTT |
| ISOP194BR9P1D1 | 95 | LPAPKNLVVSRVTEDSARLSWEHSLLNDQWFDSFLIQYQESEK VGEAIVLTVPGSERSYDLTGLKPGTEYTVSIYGVYQRGRALWYS NPLSAIFTT |
| ISOP194AR9P1E8 | 96 | LPAPKNLVVSRVTEDSARLSWEWLEHFDSFLIQYQESEKVGEAI VLTIPGSERSYDLTGLKPGTEYTVSIYGVYQRKVEFHSNPLSAIFT T |
| ISOP194AR9P1E9 | 97 | LPAPKNLVVSRVTEDSARLSWEWLEHFDSFLIQYQESEKVGEAI VLTVPGSERSYDLTGLKPGTEYTVSIYGVYQRKVNFYSNPLSAIF TT |
| ISOP194AR9P1H9 | 98 | LPAPKNLVVSRVTEDSARLSWEWLEHFDSFQIQYQESEKVGEA IVLTVPGSERSYDLTGLKPGTEYIVSIYGVYQRKVEFHSNPLSAIF TT |
| ISOP194BR9P1A9 | 99 | LPAPKNLVVSRVTEDSARLSWFNADEEYFDSFLIQYQESEKVGE AIVLTVPGSERSYDLTGLKPGTEYTVSIYGVYDRKVKFVQSNPLS AIFTT |
| ISOP194BR9P1A5 | 100 | LPAPKNLVVSRVTEDSARLSWFNADEEYFDSFLIQYQESEKVGE AIVLTVPGSERSYDLTGLKPGTEYTVSIYGVYQRGYHNWFSNPL SAIFTT |
| ISOP194BR9P1F7 | 101 | LPAPKNLVVSRVTEDSARLSWFNADEEYFDSFLIQYQESEKVGE AIVLTVPGSERSYDLTGLKPGTEYTVSIYGVYTRGRYEWRESNPL SAIFTT |
| ISOP194AR9P1G7 | 102 | LPAPKNLVVSRVTEDSARLSWGDDFNSEYFDSFLIQYQESEKV GEAIVLTVPGSERSYDLTGLKPGTEYTVSIYGVYTRAVVFTSNPL SAIFTT |
| ISOP194AR9P1E3 | 103 | LPAPKNLVVSRVTEDSARLSWKRSDDEWFDSFLIQYQESEKVG EAIVLTVPGSERSYDLTGLKPGTEYTVSIYGVYQRAALWFSNPLS AIFTT |
| ISOP194AR9P1C5 | 104 | LPAPKNLVVSRVTEDSARLSWLRDFNGRAFFDSFLIQYQESEKV GEAIVLTVPGSERSYDPTGLKPGTEYTVSIYGVFITWIHVRSNPL SAIFTT |
| ISOP194AR9P1H3 | 105 | LPAPKNLVVSRVTEDSARLSWNASWISHNFFDSFLIQYQESEK VGEAIVLTVPGSERSYDLTGLKPGTEYTVSIYGVYERKTAFYSNP LSAIFTT |

| | | |
|---|---|---|
| ISOP194GR9P1E9 | 106 | LPAPKNLVVSRVTEDSARLSWTAPDAAFDSFHIRYHEYDKNGE AIQLYVPGSERSYDLTGLKPGTEYGVFIWGVKGGLKSKPLWAW FTT |
| ISOP194HR9P1B10 | 107 | LPAPKNLVVSRVTEDSARLSWTAPDAAFDSFPIRYYERANGEAI VLTVPGSERSYDLTGLKPGTEYIVWIYGVKGGGRSGPLSAIFTT |
| ISOP194ER9P1A11 | 108 | LPAPKNLVVSRVTEDSARLSWTAPDAAFDSFRIAYYETMVSGE AIVLTVPGSERSYDLTGLKPGTEYAVIIKGVKGGKPSWPLSAIFT T |
| ISOP194ER9P1A3 | 109 | LPAPKNLVVSRVTEDSARLSWTAPDAAFDSFRIAYYETMVSGE AIVLTVPGSERSYDLTGLKPGTEYAVIIKGVKGGMVSWPLSAIFT T |
| ISOP194ER9P1H9 | 110 | LPAPKNLVVSRVTEDSARLSWTAPDAAFDSFRIAYYETMVSGE AIVLTVPGSERSYDLTGPKPGTEYAVIIKGVKGGKPSWPLSAIFT T |
| ISOP194HR9P1B2 | 111 | LPAPKNLVVSRVTEDSARLSWTAPDAAFDSFSILYGELIGDGEAI VLTVPGSERSYDLTGLKPGSEYTVYIFGVKGGRYSRPLSAIFTT |
| ISOP194HR9P1D11 | 112 | LPAPKNLVVSRVTEDSARLSWTAPDAAFDSFSILYGELIGDGEAI VLTVPGSERSYDLTGLKPGTEYTVYIFGVKGGRYSRPLSAIFTT |
| ISOP194GR9P1F6 | 113 | LPAPKNLVVSRVTEDSARLSWTAPDAAFDSFWIDYWERLSEGE AIALRVPGSERSYDLTGLKPGTEYYVWIVGVKGGKFSQPLRAW FTT |
| ISOP194GR9P1F9 | 114 | LPAPKNLVVSRVTEDSARLSWTAPDAAFDSFWIFYNERWQNG EAIRLIVPGSERSYDLTGLKPGTEYSVIIPGVKGGRNSFPLWAWF TT |
| ISOP194GR9P1C11 | 115 | LPAPKNLVVSRVTEDSARLSWTAPDAAFDSFWIFYNERWQNG EAIRLTVPGSERSYDLTGLKPGTEYWVLIGGVKGGLKSSPLWA WFTT |
| ISOP194ER9P1E6 | 116 | LPAPKNLVVSRVTEDSARLSWTAPDAAFDSFWIKYYEKRNPGE AIVLTVPGSERSYDLTGLKPGTEYLVIISGVKGGSRSVPLSAIFTT |
| ISOP194BR9P1G9 | 117 | LPAPKNLVVSRVTEDSARLSWTTAFHNEYFDSFLIQYQESEKVG EAIVLTVPGSERSYDLTGLKPGTEYTVSIYGVYIRVQVLWFSNPL SAIFTT |
| ISOP194BR9P1E4 | 118 | LPAPKNLVVSRVTEDSARLSWTTAFHNEYFDSFLIQYQESEKVG EAIVLTVPGSERSYDLTGLKPGTEYTVSIYGVYQRGYHNWFSNP LSAIFTT |
| ISOP194AR9P1H1 | 119 | LPAPKNLVVSRVTEDSARLSWWRVLGHSHFFDSFLIQYQESEK VGEAIVLTVPGSERSYDLTGLKPGTEYTVSIYGVYNRKVNFYSNP LSAIFTT |
| ISOP194BR9P1D10 | 120 | LPAPKNLVVSRVTEDSARLSWYEDNTERFDSFLIQYQESEKVVE AIVLTVPGSERSYDLTGLKPGTEYTVSIYGVYIRVQVLWFSNPLS AIFTT |
| ISOP194BR9P1C8 | 121 | LPAPKNLVVSRVTEDSARLSWYFAGELWFDSFLIQYQESEKVG EAIVLTVPGSERSYDLTGLKPGTEYTVSIYGVYQRGYHNWFSNP LSAIFTT |
| ISOP194AR9P1C10 | 122 | LPAPKNLVVSRVTEDSARPSWEWLEHFDSFLIQYQESEKVGEAI VLTVPGSERSYDLTGLKPGTEYTVSIYGVYNRKVNFYSNPLSAIF TT |
| ISOP194AR9P1D11 | 123 | LPAPKNLVVSRVTEDSGRLSWQHHISFFDSFLIQYQESEKVGEA IVLTVPGSERSYDLTGLKPGTEYTVSIYGVYNRKVNFYSNPLSAIF TT |
| ISOP194AR9P1C3 | 124 | LPAPKNLVVSRVTQNSARLSWEWLEHFDSFLIHYQESEKVGEA IVLTVPGSERSYDLTGLKPGTEYIVSIYGVYQRKVEFHSNPLSAIF TT |
| 3rd FN3 domain of tenascin C (TN3 | 125 | DAPSQIEVKDVTDTTALITWFKPLAEIDGIELTYGIKDVP GDRTTIDLTEDENQYSIGNLKPDTEYEVSLISRR GDMSSNPAKETFTT |
| Fibcon | 126 | LDAPTDLQVTNVTDTSITVSWTPPSATITGYRITYTPSNG PGEPKELTVPPSSTSVTITGLTPGVEYVVSLYAL KDNQESPPLVGTQTT |

| | | |
|---|---|---|
| 10th FN3 domain of fibronectin | 127 | VSDVPRDLEVVAATPTSLLISWDAPAVTVRYYRITYGET GGNSPVQEFTVPGSKSTATISGLKPGVDYTITVY AVTGRGDSPASSKPISINYRT |
| Linker | 128 | GSGS |
| Linker | 129 | GGGSGGGS |
| Linker | 130 | GGGGSGGGGSGGGGSGGGGSGGGGS |
| Linker | 131 | APAP |
| Linker | 132 | APAPAPAPAP |
| Linker | 133 | APAPAPAPAPAPAPAPAP |
| Linker | 134 | APAPAPAPAPAPAPAPAPAPAPAPAPAPAPAP |
| Linker | 135 | EAAAKEAAAKEAAAKEAAAKEAAAKAAA |
| Albumin variant | 136 | DAHKSEVAHRFKDLGEENFKALVLIAFAQYLQQSPFED HVKLVNEVTEFAKTCVADESAENCDKSLHTLFG DKLCTVATLRETYGEMADCCAKQEPERNECFL QHKDDNPNLPRLVRPEVDVMCTAFHDNEETFL KKYLYEIARRHPYFYAPELLFFAKRYKAAFTEC CQAADKAACLLPKLDELRDEGKASSAKQRLKC ASLQKFGERAFKAWAVARLSQRFPKAEFAEVSK LVTDLTKVHTECCHGDLLECADDRADLAKYICE NQDSISSKLKECCEKPLLEKSHCIAEVENDEMPA DLPSLAADFVESKDVCKNYAEAKDVFLGMFLY EYARRHPDYSVVLLLRLAKTYETTLEKCCAAAD PHECYAKVFDEFKPLVEEPQNLIKQNCELFEQLG EYKFQNALLVRYTKKVPQVSTPTLVEVSRNLGK VGSKCCKHPEAKRMPCAEDYLSVVLNQLCVLH EKTPVSDRVTKCCTESLVNRRPCFSALEVDETY VPKEFNAETFTFHADICTLSEKERQIKKQTALVE LVKHKPKATKEQLKAVMDDFAAFVEKCCKAD DKETCFAEEGKKLVAASQAALGL |

What is claimed:

1. A protein comprising an amino acid sequence selected from the group consisting of SEQ ID NOs: 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, and 124.

2. The protein of claim 1, wherein the protein has at least one substitution at a residue selected from the group consisting of 11, 14, 17, 37, 46, 73, and 86 corresponding to SEQ ID NO: 4.

3. The protein of claim 1, wherein the protein is conjugated to a heterologous molecule.

4. The protein of claim 3, wherein the heterologous molecule is a detectable label or a cytotoxic agent, or both.

5. The protein of claim 4, wherein the detectable label is a radioactive isotope, magnetic beads, metallic beads, colloidal particles, a fluorescent dye, an electron-dense reagent, an enzyme, biotin, digoxigenin, or hapten.

6. The protein of claim 4, wherein the detectable label is auristatin, monomethyl auristatin phenylalanine, dolostatin, chemotherapeutic agent, a drug, a growth inhibitory agent, a toxin, or a radioactive isotope.

7. The protein of claim 1, further comprising a methionine at the N-terminus of the protein.

8. The protein of claim 1, wherein the protein is coupled to a half-life extending moiety.

9. The protein of claim 8, wherein the half-life extending moiety is an albumin binding molecule, a polyethylene glygol (PEG), albumin, albumin variant, or at least a portion of an Fc region of an immunoglobulin.

10. A composition comprising the protein of claim 1 and a pharmaceutically acceptable carrier.

11. A kit comprising the protein of claim 1.

12. The protein of claim 1, wherein the amino acid sequence is selected from the group consisting of SEQ ID NOs: 34, 35, 36, 37, 38, 39, 40, 41, 42, 43, 44, 45, 46, 47, 48, and 49.

13. The protein of claim 1, wherein the amino acid sequence is selected from the group consisting of SEQ ID NOs: 50, 51, 52, 53, 54, 55, 56, 57, 58, 59, 60, 61, 62, 63, and 64.

14. The protein of claim 1, wherein the amino acid sequence is selected from the group consisting of SEQ ID NOs: 65, 66, 67, 68, 69, 70, 71, 72, 73, 74, 75, 76, 77, 78, and 79.

15. The protein of claim 1, wherein the amino acid sequence is selected from the group consisting of SEQ ID NOs: 80, 81, 82, 83, 84, 85, 86, 87, 88, 89, 90, 91, 92, 93, and 94.

16. The protein of claim 1, wherein the amino acid sequence is selected from the group consisting of SEQ ID NOs: 95, 96, 97, 98, 99, 100, 101, 102, 103, 104, 105, 106, 107, 108, and 109.

17. The protein of claim 1, wherein the amino acid sequence is selected from the group consisting of SEQ ID NOs: 110, 111, 112, 113, 114, 115, 116, 117, 118, 119, 120, 121, 122, 123, and 124.

* * * * *